(12) United States Patent
Kitamura et al.

(10) Patent No.: US 11,844,229 B2
(45) Date of Patent: Dec. 12, 2023

(54) ELECTROLUMINESCENT ELEMENT, AND LIGHT EMITTING DEVICE, DISPLAY DEVICE AND LIGHTING DEVICE EACH USING ORGANIC ELECTROLUMINESCENT ELEMENT

(71) Applicant: UDC Ireland Limited, Dublin (IE)

(72) Inventors: Tetsu Kitamura, Kanagawa (JP); Koji Takaku, Kanagawa (JP); Wataru Sotoyama, Kanagawa (JP); Yasunori Yonekuta, Kanagawa (JP); Toshihiro Ise, Kanagawa (JP); Saki Takada, Kanagawa (JP); Toru Watanabe, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 455 days.

(21) Appl. No.: 16/790,316

(22) Filed: Feb. 13, 2020

(65) Prior Publication Data

US 2020/0203648 A1 Jun. 25, 2020

Related U.S. Application Data

(63) Continuation of application No. 14/124,851, filed as application No. PCT/JP2012/064456 on Jun. 5, 2012, now abandoned.

(30) Foreign Application Priority Data

Jun. 16, 2011 (JP) ................................ 2011-134147

(51) Int. Cl.
*H10K 50/00* (2023.01)
*C07D 251/14* (2006.01)
(Continued)

(52) U.S. Cl.
CPC ............ *H10K 50/00* (2023.02); *C07D 251/14* (2013.01); *C09K 11/06* (2013.01); *H05B 33/10* (2013.01);
(Continued)

(58) Field of Classification Search
CPC .................. C07D 251/14; C09K 11/06; C09K 11/1007; C09K 2211/1011; C09K 2211/1014;
(Continued)

(56) References Cited

U.S. PATENT DOCUMENTS

2004/0058195 A1* 3/2004 Kita ..................... H10K 85/656
252/301.16
2004/0076853 A1 4/2004 Jarikov
(Continued)

FOREIGN PATENT DOCUMENTS

EP 1808912 7/2007
JP 2002324678 A 11/2002
(Continued)

OTHER PUBLICATIONS

Oh et al., Organic Electronics, vol. 10, (2009), pp. 163-169. (Year: 2009).*
(Continued)

*Primary Examiner* — Dawn L Garrett
(74) *Attorney, Agent, or Firm* — Riverside Law LLP

(57) ABSTRACT

An organic electroluminescent element which has a substrate, a pair of electrodes disposed on this substrate and composed of an anode and a cathode, and at least one organic layer disposed between these electrodes and including a light-emitting layer, and in which a compound expressed by General Formula 1-1 is contained in at least one layer of the aforementioned light-emitting layer(s) exhibits high luminous efficiency, excellent blue color
(Continued)

purity, and little change in chromaticity accompanying drive deterioration. ($R^1$ to $R^{10}$ [each] represent a hydrogen atom or a substituent, and at least one of $R^1$ to $R^{10}$ is a substituent expressed by General Formula 1-2; however, a pyrene skeleton is never contained in $R^1$ to $R^{10}$; the asterisk indicates the bonding position with a pyrene ring; $X^1$ to $X^5$ [each] represent a carbon atom or a nitrogen atom, and at least one of $X^1$ to $X^5$ is a nitrogen atom; $R^{11}$ to $R^{15}$ [each] represent a hydrogen atom or a substituent, and at least one of $R^{11}$ to $R^{15}$ is an alkyl group or a silyl group; however, if $X^1$ to $X^5$ represent nitrogen atoms, there is no $R^{11}$ to $R^{15}$ bonded on these nitrogen atoms.)

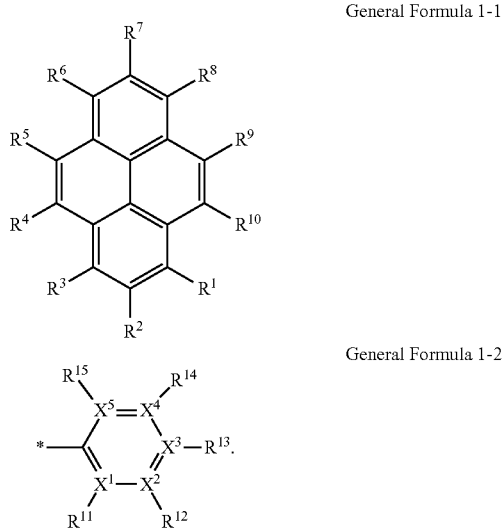

General Formula 1-1

General Formula 1-2

16 Claims, 2 Drawing Sheets

(51) Int. Cl.
| | |
|---|---|
| H10K 85/40 | (2023.01) |
| H10K 85/60 | (2023.01) |
| H10K 50/11 | (2023.01) |
| H10K 85/30 | (2023.01) |
| H10K 101/10 | (2023.01) |
| C09K 11/06 | (2006.01) |
| H05B 33/10 | (2006.01) |

(52) U.S. Cl.
CPC .......... *H10K 85/40* (2023.02); *H10K 85/622* (2023.02); *H10K 85/654* (2023.02); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *H10K 50/11* (2023.02); *H10K 85/324* (2023.02); *H10K 85/611* (2023.02); *H10K 85/631* (2023.02); *H10K 85/636* (2023.02); *H10K 85/6572* (2023.02); *H10K 2101/10* (2023.02)

(58) Field of Classification Search
CPC .... C09K 2211/1029; C09K 2211/1044; C09K 2211/1059; C09K 2211/1007; H01L 51/0051; H01L 51/0054; H01L 51/0059; H01L 51/0061; H01L 51/0067; H01L 51/0072; H01L 51/0081; H01L 51/0094; H01L 51/50; H01L 51/5012; H01L 51/5016; H05B 33/10; H10K 50/00; H10K 85/40; H10K 85/622; H10K 85/654; H10K 50/11; H10K 85/324; H10K 85/611; H10K 85/631; H10K 85/636; H10K 85/6572; H10K 2101/10
See application file for complete search history.

(56) References Cited

U.S. PATENT DOCUMENTS

| | | | |
|---|---|---|---|
| 2005/0238910 | A1 | 10/2005 | Ionkin |
| 2007/0114917 | A1* | 5/2007 | Funahashi ............... C07F 7/081 564/426 |
| 2007/0155981 | A1 | 7/2007 | Shin |
| 2007/0167626 | A1 | 7/2007 | Kim |
| 2007/0205715 | A1 | 9/2007 | Saitoh |
| 2008/0075973 | A1 | 3/2008 | Kim |
| 2009/0236975 | A1* | 9/2009 | Ito ......................... C07F 7/0805 313/504 |
| 2011/0240983 | A1 | 10/2011 | Sekiguchi |
| 2015/0263290 | A1 | 9/2015 | Cho |

FOREIGN PATENT DOCUMENTS

| | | |
|---|---|---|
| JP | 2004091444 | 3/2004 |
| JP | 2007131723 | 5/2007 |
| JP | 2008162911 | 7/2008 |
| JP | 2010138121 | 6/2010 |
| JP | 2011014886 | 8/2012 |
| KR | 20120029258 | 3/2012 |
| WO | 2005123634 | 12/2005 |

OTHER PUBLICATIONS

Figueira-Duarte et al., Chem. Rev., vol. 111, (2011), pp. 7260-7314. (Year: 2011).*
Yeh CC, Lee MT, Chen HH, Chen CH. 17.3: High-Performance Blue OLEDs Based on a Sterically Hindered Pyrene Host Material. InSID Symposium Digest of Technical Papers May 2004 (vol. 35, No. 1, pp. 788-791). Oxford, UK: Blackwell Publishing Ltd. (Year: 2004).*
Murphy, C.J. and Post, H.W., 1962. Studies in Organosilicon Chemistry. XLIII. An Investigation of Silicon-Containing s-Triazines. The Journal of Organic Chemistry, 27(4), pp. 1486-1488. (Year: 1962).*
Dyes and Pigments, 26(4), pp. 247-255, date: 1994.
Justus Liebigs Annalen der Chemie, (1962), 652, pp. 192-203.
Machine translation for JP 2007-31723 A (publication date: May 2007).
Office Action dated Nov. 13, 2019 for U.S. Appl. No. 14/124,851 (pp. 1-19).
Organometallics, (2006), 25, pp. 1461-1471.

* cited by examiner

ELECTROLUMINESCENT ELEMENT, AND LIGHT EMITTING DEVICE, DISPLAY DEVICE AND LIGHTING DEVICE EACH USING ORGANIC ELECTROLUMINESCENT ELEMENT

CROSS REFERENCE TO RELATED APPLICATIONS

The present application is a continuation of U.S. patent application Ser. No. 14/124,851, filed Feb. 26, 2014, which is a 35 U.S.C. § 371 national phase application from, and claiming priority to, International Application No. PCT/JP2012/064456, filed Jun. 5, 2012, which claims priority to Japanese Patent Application No. 2011-134147, filed Jun. 16, 2011, all of which applications are incorporated by reference herein in their entireties.

TECHNICAL FIELD

The present invention relates to an organic electroluminescent element and a material for use in an organic electroluminescent element. Furthermore, the present invention also relates to a light-emitting device, display device, or lighting device which uses the aforementioned organic electroluminescent element.

BACKGROUND ART

Organic electroluminescent elements (hereinafter also referred to as "elements" or "organic EL elements") emit light at a high brightness and at a low drive voltage and have therefore been the subject of active research and development. An organic electroluminescent element has an organic layer between a pair of electrodes. Electrons injected from the cathode and holes injected from the anode are rebonded at the organic layer, and the energy of the excitons thus produced is utilized to emit light. Organic electroluminescent elements can be provided as elements having a variety of emission wavelengths, and they are expected to find use in a wide range of applications because they have high response speed and are relatively thin and lightweight. In particular, the development of an organic electroluminescent element with high blue color purity and high luminous efficiency is important in applications to full-color displays and so on, and various research and development results have been reported up to now.

For example, Patent Document 1 describes an organic electroluminescent element that uses a condensed polycyclic aromatic compound containing widespread triazine groups. Working examples of organic electroluminescent elements that use compounds in which substituted or unsubstituted triazine groups are substituted in a pyrene skeleton are cited in this [document], and it is indicated that blue light emission was realized with good luminous efficiency and that a long service life was achieved. In particular, only compounds described as example compounds in Patent Document 1 are ones with a pyrene skeleton in which the substituents belonging to triazine groups are substituted or unsubstituted phenyl groups.

Moreover, Patent Document 2 also describes an organic electroluminescent element that uses compounds in which substituted or unsubstituted nitrogen-containing heterocyclic groups are substituted in a pyrene skeleton. It is indicated in Patent Document 2 as well that blue light emission was realized with good luminous efficiency and that a high brightness was achieved. In particular, in Patent Document 2, virtually all of the example compounds are those in which the nitrogen-containing heterocyclic groups are unsubstituted, with the only example compounds in which the nitrogen-containing heterocyclic groups have substituents being compounds having fluorine atoms or phenyl groups as substituents.

Patent Document 3 describes pyrene compounds in which nitrogen-containing aromatic heterocycles are substituted, but there are no concrete examples of compounds having alkyl groups or silyl groups in the nitrogen-containing aromatic heterocycles.

RELATED ART DOCUMENTS

Patent Documents

Patent Document 1: Japanese Laid-Open Patent Application 2010-138121
Patent Document 2: Japanese Laid-Open Patent Application 2011-14886
Patent Document 3: Japanese Laid-Open Patent Application 2007-131723

SUMMARY OF THE INVENTION

Problems to be Solved by the Invention

However, investigation by the present inventors has revealed that there is still room for improvement in the luminous efficiency of the organic electroluminescent elements described in the aforementioned Patent Documents 1 and 2. Furthermore, it also became clear that the purity of the blue color of these organic electroluminescent elements cannot be considered to be adequate, and that higher blue color purity must be realized. Moreover, it was also revealed that when these organic electroluminescent elements are used continuously for an extended period of time, drive deterioration in which emission intensity decreases is accompanied by a change in chromaticity (hereinafter also referred to as "change in chromaticity after driving"). In addition, although the organic electroluminescent element in Patent Document 3 emits blue light, investigation by the present inventors has revealed that the compounds described in this document have low luminous efficiency and that chromaticity changes during drive, which are areas to be improved.

Means for Solving the Problems

In view of this, the present inventors conducted diligent investigation aimed at providing an organic electroluminescent element which had high luminous efficiency and excellent blue color purity and with which there was little change in chromaticity accompanying drive deterioration. As a result, they arrived at the present invention described below upon discovering that the aforementioned problems could be solved by using a pyrene derivative having a specific structure.

(1) An organic electroluminescent element having a substrate, a pair of electrodes disposed on this substrate and composed of an anode and a cathode, and at least one organic layer disposed between these electrodes and including a light-emitting layer, wherein a compound expressed by General Formula 1-1[1] below is contained in at least one layer of the aforementioned light-emitting layer(s):

[First Chemical Formula]

General Formula 1-1

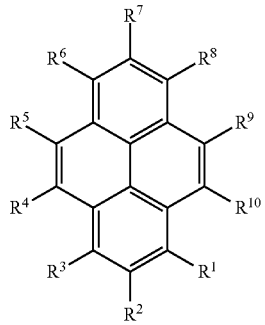

(In General Formula 1-1, $R^1$ to $R^{10}$ represent each independently a hydrogen atom or a substituent, and at least one of $R^1$ to $R^{10}$ is a substituent expressed by General Formula 1-2 below; however, a pyrene skeleton is never contained in $R^1$ to $R^{10}$.)

[1] Translator's note: In the Japanese original document, the labeling number for each of the general formulas is indicated in parentheses, but we have omitted the parentheses in the translation to avoid confusion with other parenthetical notations.

[Second Chemical Formula]

General Formula 1-2

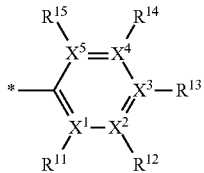

(In General Formula 1-2, the asterisk indicates the bonding position with a pyrene ring; $X^1$ to $X^5$ represent each independently a carbon atom or a nitrogen atom, and at least one of $X^1$ to $X^5$ is a nitrogen atom; $R^{11}$ to $R^{15}$ represent each independently a hydrogen atom or a substituent, and at least one of $R^{11}$ to $R^{15}$ represents an alkyl group or a silyl group; however, if $X^1$ to $X^5$ represent nitrogen atoms, there is no $R^{11}$ to $R^{15}$ bonded on these nitrogen atoms.)

(2) The organic electroluminescent element according to (1), wherein $R^1$ to $R^{10}$ in General Formula 1-1 above do not jointly form a ring.

(3) The organic electroluminescent element according to (1) or (2), wherein the compound expressed by General Formula 1-1 above is expressed by General Formula 2 below:

[Third Chemical Formula]

General Formula 2

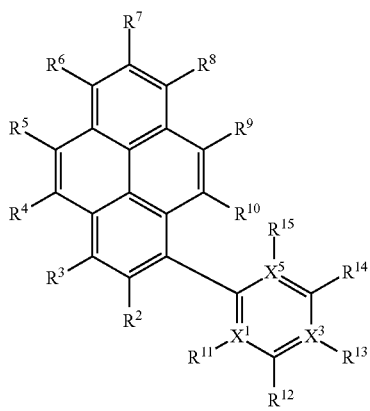

(In General Formula 2, $R^2$ to $R^{10}$ represent each independently a hydrogen atom or a substituent; $X^1$, $X^3$, and $X^5$ represent each independently a carbon atom or a nitrogen atom, and at least one of $X^1$, $X^3$, and $X^5$ is a nitrogen atom; $R^{11}$ to $R^{15}$ represent each independently a hydrogen atom or a substituent, and at least one of $R^{11}$ to $R^{15}$ represents an alkyl group or a silyl group, but if $X^1$, $X^3$, and $X^5$ represent nitrogen atoms, there is no $R^{11}$, $R^{13}$, or $R^{15}$ bonded on these nitrogen atoms; however, a pyrene skeleton is never contained in $R^2$ to $R^{15}$, and even when $R^{11}$ to $R^{15}$ jointly form a ring, a pyrene skeleton is never formed.)

(4) The organic electroluminescent element according to any one of (1) to (3), wherein $R^{12}$ and/or $R^{14}$ in General Formula 1-1 [sic][2] above is an alkyl group or a silyl group.

[2] Translator's note: apparent error in the original; "General Formula 1-1" should be "General Formula 1-2" (same below).

(5) The organic electroluminescent element according to any one of (1) to (3), wherein both $R^{12}$ and $R^{14}$ in General Formula 1-1 [sic] above are an alkyl group or a silyl group.

(6) The organic electroluminescent element according to any one of (1) to (5), wherein the compound expressed by General Formula 1-1 above is expressed by any of General Formulas 3-1 to 3-3 below:

[Fourth Chemical Formula]

General Formula 3-1

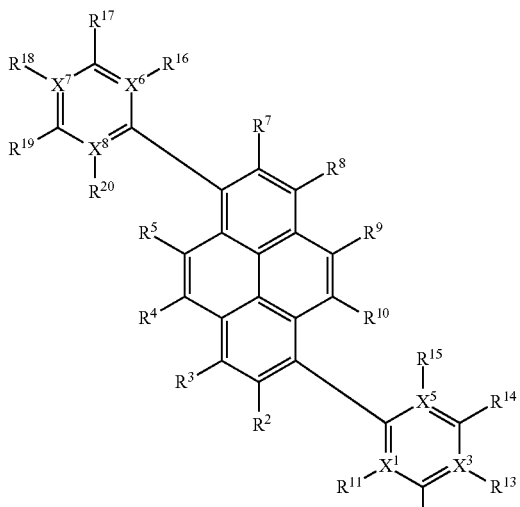

General Formula 3-2

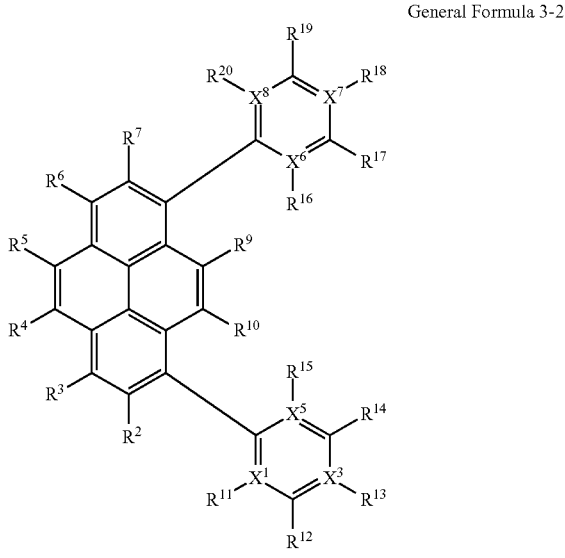

General Formula 3-3

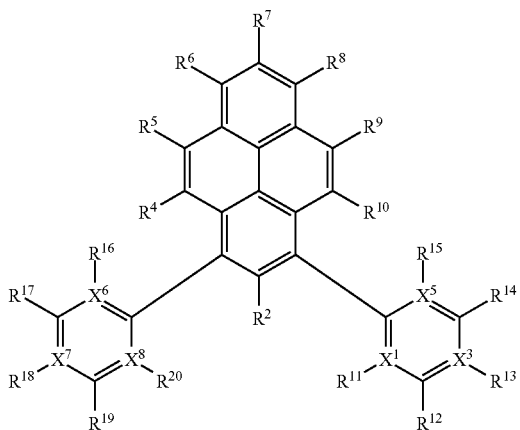

(In General Formulas 3-1 to 3-3, $R^2$ to $R^{10}$ represent each independently a hydrogen atom or a substituent; $X^1$, $X^3$, and $X^5$ represent each independently a carbon atom or a nitrogen atom, and at least one of $X^1$, $X^3$, and $X^5$ is a nitrogen atom; $R^{11}$ to $R^{15}$ represent each independently a hydrogen atom or a substituent, and at least one of $R^{11}$ to $R^{15}$ represents an alkyl group or a silyl group; at least one of $X^6$ to $X^8$ is a nitrogen atom; $R^{16}$ to $R^{20}$ represent each independently a hydrogen atom or a substituent, and at least one of $R^{16}$ to $R^{20}$ represents an alkyl group or a silyl group, but if $X^1$, $X^3$, $X^5$, and $X^6$ to $X^8$ represent nitrogen atoms, there is no $R^{11}$, $R^{13}$, $R^{15}$, $R^{16}$, $R^{18}$, or $R^{20}$ bonded on these nitrogen atoms; however, a pyrene skeleton is never contained in $R^2$ to $R^{20}$, and even when $R^{11}$ to $R^{15}$ jointly form a ring, or even when $R^{16}$ to $R^{20}$ jointly form a ring, a pyrene skeleton is never formed.)

(7) The organic electroluminescent element according to (6), wherein $R^{11}$ to $R^{20}$ in General Formulas 3-1 to 3-3 above represent each independently a hydrogen atom, an alkyl group, or a silyl group.

(8) The organic electroluminescent element according to (6) or (7), wherein at least two of $X^1$, $X^3$, and $X^5$ or at least two of $X^6$ to $X^8$ in General Formulas 3-1 to 3-3 above are nitrogen atoms.

(9) The organic electroluminescent element according to any one of (1) to (8), wherein at least one of $R^2$, $R^3$, $R^4$, $R^5$, $R^7$, $R^9$, and $R^{10}$ in General Formula 1-1 above, General Formula 2 above, and General Formulas 3-1 to 3-3 above is a substituent.

(10) The organic electroluminescent element according to any one of (1) to (8), wherein at least one of $R^2$, $R^3$, $R^4$, $R^5$, $R^7$, $R^9$, and $R^{10}$ in General Formula 1-1 above, General Formula 2 above, and General Formulas 3-1 to 3-3 above is a substituent from among an alkyl group, a silyl group, an amino group, a fluorine atom, and a phenyl group or pyridyl group that has been substituted with at least one of these groups.

(11) The organic electroluminescent element according to any one of (1) to (10), wherein at least one of $R^2$ to $R^{10}$ in General Formula 1-1 above, General Formula 2 above, and General Formulas 3-1 to 3-3 above is an ortho-alkyl-substituted phenyl group.

(12) The organic electroluminescent element according to (11), wherein the aforementioned ortho-alkyl-substituted phenyl group is an o-tolyl group, a 2,6-xylyl group, or a mesityl group.

(13) The organic electroluminescent element according to any one of (1) to (12), wherein $R^2$, $R^3$, $R^4$, $R^5$, $R^7$, $R^9$, and $R^{10}$ in General Formula 1-1 above, General Formula 2 above, and General Formulas 3-1 to 3-3 above are [each] an alkyl group, a silyl group, an amino group, a fluorine atom, a phenyl group or pyridyl group that has been substituted with at least one of these groups, or a hydrogen atom.

(14) The organic electroluminescent element according to any one of (1) to (13), wherein the molecular weight of the compound expressed by General Formula 1-1 above is 1000 or less.

(15) The organic electroluminescent element according to any one of (1) to (14), wherein the compound expressed by General Formula 1-1 above is a light-emitting material.

(16) The organic electroluminescent element according to any one of (1) to (15), wherein the aforementioned light-emitting layer includes an anthracene-based host material.

(17) A light-emitting device which makes use of the organic electroluminescent element according to any one of (1) to (16).

(18) A display device which makes use of the organic electroluminescent element according to any one of (1) to (16).

(19) A lighting device which makes use of the organic electroluminescent element according to any one of (1) to (16).

(20) A material for an organic electroluminescent element composed of a compound expressed by General Formula 1-1 below:

[Fifth Chemical Formula]

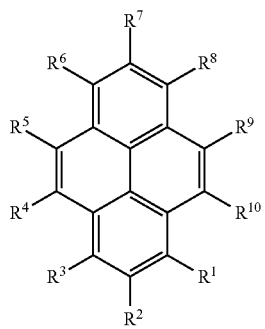

General Formula 1-1

(In General Formula 1-1, $R^1$ to $R^{10}$ represent each independently a hydrogen atom or a substituent, and at least one of $R^1$ to $R^{10}$ is a substituent expressed by General Formula 1-2 below; however, a pyrene skeleton is never contained in $R^1$ to $R^{10}$.)

[Sixth Chemical Formula]

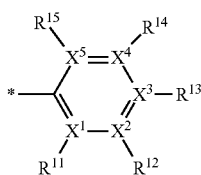

General Formula 1-2

(In General Formula 1-2, the asterisk indicates the bonding position with a pyrene ring; $X^1$ to $X^5$ represent each independently a carbon atom or a nitrogen atom, and at least one of $X^1$ to $X^5$ is a nitrogen atom; $R^{11}$ to $R^{15}$ represent each independently a hydrogen atom or a substituent, and at least one of $R^{11}$ to $R^{15}$ represents an alkyl group or a silyl group; however, if $X^1$ to $X^5$ represent nitrogen atoms, there is no $R^{11}$ to $R^{15}$ bonded on these nitrogen atoms.)

(21) The material for an organic electroluminescent element according to (20), wherein $R^1$ to $R^{10}$ in General Formula 1-1 above do not jointly form a ring.

(22) The material for an organic electroluminescent element according to (20) or (21), wherein the compound expressed by General Formula 1-1 above is expressed by General Formula 2 below:

[Seventh Chemical Formula]

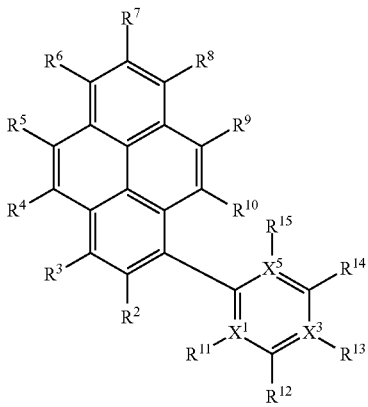

General Formula 2

(In General Formula 2, $R^2$ to $R^{10}$ represent each independently a hydrogen atom or a substituent; $X^1$, $X^3$, and $X^5$ represent each independently a carbon atom or a nitrogen atom, and at least one of $X^1$, $X^3$, and $X^5$ is a nitrogen atom; $R^{11}$ to $R^{15}$ represent each independently a hydrogen atom or a substituent, and at least one of $R^{11}$ to $R^{15}$ represents an alkyl group or a silyl group, but if $X^1$, $X^3$, and $X^5$ represent nitrogen atoms, there is no $R^{11}$, $R^{13}$, or $R^{15}$ bonded on these nitrogen atoms; however, a pyrene skeleton is never contained in $R^2$ to $R^{15}$, and even when $R^{11}$ to $R^{15}$ jointly form a ring, a pyrene skeleton is never formed.)

(23) The material for an organic electroluminescent element according to any one of (20) to (22), wherein $R^{12}$ and/or $R^{14}$ in General Formula 1-1 [sic][3] above is an alkyl group or a silyl group.

[3] Translator's note: apparent error in the original; "General Formula 1-1" should be "General Formula 1-2" (same below).

(24) The material for an organic electroluminescent element according to any one of (20) to (22), wherein both $R^{12}$ and $R^{14}$ in General Formula 1-1 [sic] above are an alkyl group or a silyl group.

(25) The material for an organic electroluminescent element according to any one of (20) to (24), wherein the compound expressed by General Formula 1-1 above is expressed by any of General Formulas 3-1 to 3-3 below:

[Eighth Chemical Formula]

General Formula 3-1

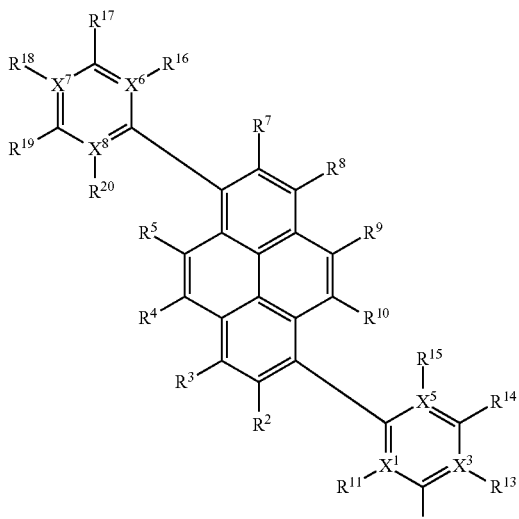

General Formula 3-2

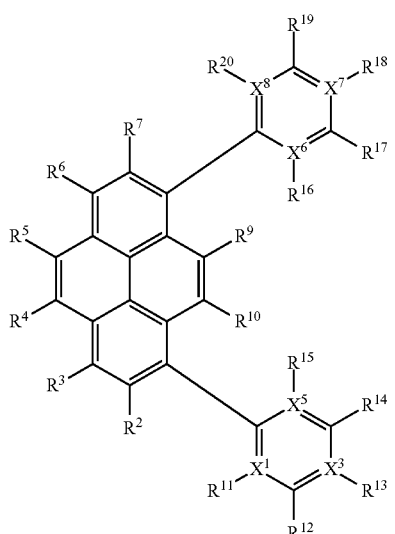

General Formula 3-3

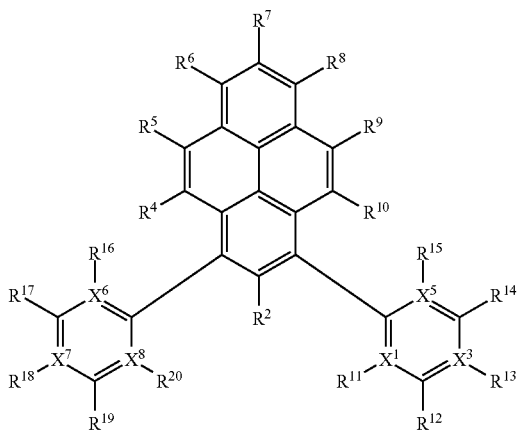

(In General Formulas 3-1 to 3-3, $R^2$ to $R^{10}$ represent each independently a hydrogen atom or a substituent; $X^1$, $X^3$, and $X^5$ represent each independently a carbon atom or a nitrogen atom, and at least one of $X^1$, $X^3$, and $X^5$ is a nitrogen atom; $R^{11}$ to $R^{15}$ represent each independently a hydrogen atom or a substituent, and at least one of $R^{11}$ to $R^{15}$ represents an alkyl group or a silyl group; at least one of $X^6$ to $X^8$ is a nitrogen atom; $R^{16}$ to $R^{20}$ represent each independently a hydrogen atom or a substituent, and at least one of $R^{16}$ to $R^{20}$ represents an alkyl group or a silyl group, but if $X^1$, $X^3$, $X^5$, and $X^6$ to $X^8$ represent nitrogen atoms, there is no $R^{11}$, $R^{13}$, $R^{15}$, $R^{16}$, $R^{18}$, or $R^{20}$ bonded on these nitrogen atoms; however, a pyrene skeleton is never contained in $R^2$ to $R^{20}$, and even when $R^{11}$ to $R^{15}$ jointly form a ring, or even when $R^{16}$ to $R^{20}$ jointly form a ring, a pyrene skeleton is never formed.)

(26) The material for an organic electroluminescent element according to (25), wherein $R^{11}$ to $R^{20}$ in General Formulas 3-1 to 3-3 above represent each independently a hydrogen atom, an alkyl group, or a silyl group.

(27) The material for an organic electroluminescent element according to (25) or (26), wherein at least two of $X^1$, $X^3$, and $X^5$ or at least two of $X^6$ to $X^8$ in General Formulas 3-1 to 3-3 above are nitrogen atoms.

(28) The material for an organic electroluminescent element according to any one of (20) to (27), wherein at least one of $R^2$, $R^3$, $R^4$, $R^5$, $R^7$, $R^9$, and $R^{10}$ in General Formula 1-1 above, General Formula 2 above, and General Formulas 3-1 to 3-3 above is a substituent.

(29) The material for an organic electroluminescent element according to any one of (20) to (28), wherein at least one of $R^2$, $R^3$, $R^4$, $R^5$, $R^7$, $R^9$, and $R^{10}$ in General Formula 1-1 above, General Formula 2 above, and General Formulas 3-1 to 3-3 above is a substituent from among an alkyl group, a silyl group, an amino group, a fluorine atom, and a phenyl group or pyridyl group that has been substituted with at least one of these groups.

(30) The material for an organic electroluminescent element according to any one of (20) to (29), wherein at least one of $R^2$ to $R^{10}$ in General Formula 1-1 above, General Formula 2 above, and General Formulas 3-1 to 3-3 above is an ortho-alkyl-substituted phenyl group.

(31) The material for an organic electroluminescent element according to (30), wherein the aforementioned ortho-alkyl-substituted phenyl group is an o-tolyl group, a 2,6-xylyl group, or a mesityl group.

(32) The material for an organic electroluminescent element according to any one of (20) to (31), wherein $R^2$, $R^3$, $R^4$, $R^5$, $R^7$, $R^9$, and $R^{10}$ in General Formula 1-1 above, General Formula 2 above, and General Formulas 3-1 to 3-3 above are [each] an alkyl group, a silyl group, an amino group, a fluorine atom, a phenyl group or pyridyl group that has been substituted with at least one of these groups, or a hydrogen atom.

(33) The material for an organic electroluminescent element according to any one of (20) to (32), wherein the molecular weight of the compound expressed by General Formula 1-1 above is 1000 or less.

(34) The material for an organic electroluminescent element according to any one of (20) to (33), wherein the compound expressed by General Formula 1-1 above is a light-emitting material.

Effects of the Invention

The organic electroluminescent element of the present invention has the advantageous effect of exhibiting high luminous efficiency, excellent blue color purity, and little change in chromaticity accompanying drive deterioration. Furthermore, the use of the compound of the present invention makes it possible to easily manufacture such a superior organic electroluminescent element. Moreover, the light-emitting device, display device, and lighting device of the present invention have the advantageous effect of low power consumption, excellent blue color purity, and resistance to change in chromaticity over extended usage.

DETAILED DESCRIPTION OF EMBODIMENTS

Figure 1:
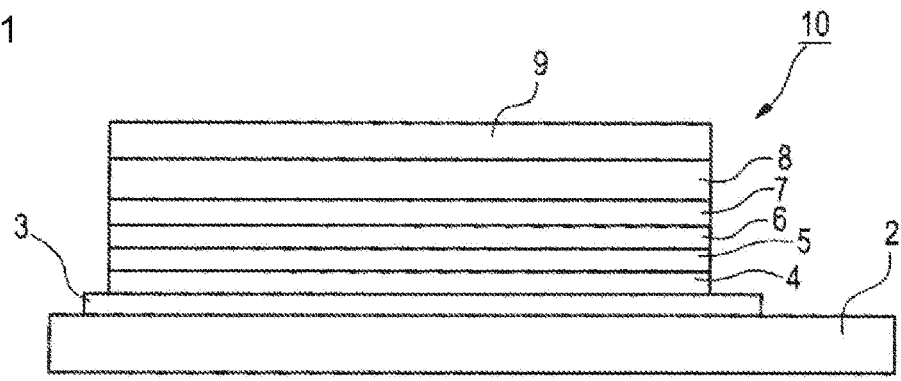
FIG. 1 is a schematic diagram illustrating one example of the configuration of the organic electroluminescent element according to the present invention.

The content of the present invention will be described in detail below. The description of the constituent elements mentioned below may be based on typical embodiments and concrete examples of the present invention, but the present invention is in no way limited to such embodiments or concrete examples. Note that the range of numerical values expressed with the use of [the phrase] "from . . . to . . . " in this Specification means a range which is such that the numerical values given are included as the minimum value and maximum value, respectively.

Material for Organic Electroluminescent Element Expressed by General Formula 1-1

The organic electroluminescent element of the present invention is characterized in that a material for an organic electroluminescent element expressed by General Formula 1-1 below is contained in the light-emitting layer(s) of the organic layer(s) constituting the organic electroluminescent element:

[Ninth Chemical Formula]

General Formula 1-1

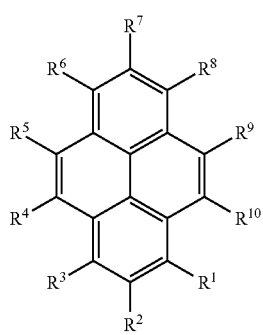

(In General Formula 1-1, $R^1$ to $R^{10}$ represent each independently a hydrogen atom or a substituent, and at least one of $R^1$ to $R^{10}$ is a substituent expressed by General Formula 1-2 below; however, a pyrene skeleton is never contained in $R^1$ to $R^{10}$.)

[Tenth Chemical Formula]

General Formula 1-2

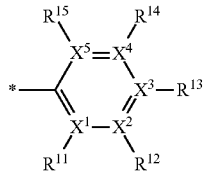

(In General Formula 1-2, the asterisk indicates the bonding position with a pyrene ring; $X^1$ to $X^5$ represent each independently a carbon atom or a nitrogen atom, and at least one of $X^1$ to $X^5$ is a nitrogen atom; $R^{11}$ to $R^{15}$ represent each independently a hydrogen atom or a substituent, and at least one of $R^{11}$ to $R^{15}$ represents an alkyl group or a silyl group; however, if $X^1$ to $X^5$ represent nitrogen atoms, there is no $R^{11}$ to $R^{15}$ bonded on these nitrogen atoms.)

As a result of a compound expressed by General Formula 1-1 being contained in the light-emitting layer(s) of the organic layer(s), the organic electroluminescent element of the present invention has the characteristic feature of the emission spectrum becoming sharp and the purity of the blue color becoming favorable. Shortening the emission wavelength is also known to be effective in improving the purity of the blue color. However, if the emission wavelength of the light-emitting material is shortened, the $S_1$ (lowest excited singlet energy level) of the light-emitting material becomes large, so the difference between the $S_1$ of the light-emitting material and the $S_1$ of the host material becomes small, or the $S_1$ of the host material becomes larger than the $S_1$ of the light-emitting material. This also causes problems in that the luminous efficiency is decreased and also that auxiliary light emissions from the host material are mixed in, decreasing the purity of the blue color. In contrast, if the compound expressed by General Formula 1-1 is used in accordance with the present invention, it is possible to make the spectrum sharp and to improve the purity of the blue color while realizing a high luminous efficiency.

Although no particular theory holds sway, such sharpening of the emission spectrum of the compound expressed by General Formula 1-1 can be achieved [as follows: namely,] a nitrogen-containing aromatic heterocyclic group is first introduced into a pyrene ring, thereby the bias in charges within the molecule makes the structural changes between the ground state and the excited state smaller, so the emission spectrum can be made sharper in comparison to compounds in which an aryl-substituted group is introduced into a pyrene ring. Examples of such compounds with a nitrogen-containing aromatic heterocyclic group being introduced into a pyrene ring are given in Japanese Laid-Open Patent Application 2010-138121 or the like, but in the present invention, by additionally introducing at least one alkyl group or silyl group into a nitrogen-containing heterocycle that has been substituted into a pyrene ring, it is possible to control the n-conjugated electron system within the molecule to an appropriate range, so the structural changes between the ground state and the excited state are made even smaller, and this is thought to cause [the sharpening of the emission spectrum].

It is preferable from the standpoint of improving color purity that the compounds expressed by General Formula 1-1 and used as the material for organic electroluminescent elements of the present invention further possess an aggregation-suppressing effect. However, the present invention is in no way limited to the magnitude of such an aggregation-suppressing effect. Pyrene-based compounds have the property that longer-wavelength aggregate emission (excimer emission) occurs more readily than monomer emission, so aggregate emission may also lead to a decrease in color purity. The compounds expressed by General Formula 1-1 of the present invention are thought to effectively suppress aggregation between pyrene rings without reducing color purity as a result of $R^{11}$ to $R^{15}$ having at least one alkyl group or silyl group. Therefore, the compounds expressed by General Formula 1-1 of the present invention have a higher aggregation-suppressing effect and also higher color purity than the conventional compounds that simply have nitrogen-containing heterocyclic groups as substituents and that do not have any alkyl groups or silyl groups.

In addition, by having at least one alkyl group or silyl group in the nitrogen-containing heterocyclic groups, the chemical stability of the compound is improved, and changes in chromaticity after driving occur less readily without reducing the color purity.

Note that a preferred mode of the present invention is a case in which, besides $R^{11}$ to $R^{15}$, which three-dimensionally stick out from the nitrogen-containing heterocycle in General Formula 1-1 above, at least one of $R^2$, $R^3$, $R^4$, $R^5$, $R^7$, $R^9$, and $R^{10}$ is a substituent from among an alkyl group, a silyl group, an amino group, a fluorine atom, or a phenyl group or pyridyl group that has been substituted with at least one of these groups, so aggregation between pyrene-based compounds occurs even less readily. Furthermore, as will be described later, it is more preferable if three or more locations of $R^1$ to $R^{10}$ of the pyrene ring in General Formula 1-1 above are substituents of specific structures that contribute to the suppression of aggregates because aggregation between pyrene-based compounds occurs even less readily.

Moreover, if a compound expressed by General Formula 1-1 is used, the probability of transition between the excited state and the base state (the vibrator intensity) also becomes higher, and the luminous efficiency can be made higher in comparison to compounds in which an aryl substituent is introduced into the pyrene ring.

Meanwhile, as was described above, when a conventional pyrene-based compound is used to produce an organic electroluminescent element, continued use over an extended period of time leads to a drop in emission intensity, and this drive deterioration ends up resulting in a change in chromaticity. Conceivable causes of such a change in chromaticity accompanying drive deterioration include a change in the emission location (and the attendant optical interference) due to a change in the element charge balance, the formation of aggregates between pyrene rings due to heat generation or the like accompanying drive, the production of light-emitting components due to deterioration of the chemical reaction of the host material or the light-emitting material through element drive, and so forth. Accordingly, in order to prevent the change in chromaticity that accompanies drive deterioration, it is necessary to provide a material in which all these things are less likely to occur. The compound expressed by General Formula 1-1 in the present invention is stable with respect to holes (oxidation) and electrons (reduction), has good charge injection and transport properties, is resistant to the formation of aggregates between pyrene rings, and is also resistant to deterioration of the chemical reaction due to element drive. Therefore, the change in chromaticity that accompanies drive deterioration is also less likely to occur. In addition, the compound expressed by General Formula 1-1 of the present invention is resistant to the formation of aggregates between pyrene rings, so it is also possible to form a light-emitting layer by itself without using any host material.

The compound expressed by General Formula 1-1 will be described in detail below.

In the present invention, a hydrogen atom in the description of General Formula 1-1 above also includes an isotope [of hydrogen] (such as a deuterium atom), and atoms further constituting a substituent also encompass isotopes thereof.

In the present invention, when the term "substituent" is used, that substituent may be further substituted. For example, when "alkyl group" is referred to in the present invention, it encompasses alkyl groups that have been substituted with a fluorine atom (such as a trifluoromethyl group), alkyl groups that have been substituted with an aryl group (such as a triphenylmethyl group), and so forth, and when the term "$C_1$ to $C_6$ alkyl group" is used, this indicates that the carbon number is from 1 to 6 for the entire group, including one that has been substituted.

In General Formula 1-1, $R^1$ to $R^{10}$ represent each independently a hydrogen atom or a substituent, and at least one of $R^1$ to $R^{10}$ is a substituent expressed by General Formula 1-2 above. However, a pyrene skeleton is never included in $R^1$ to $R^{10}$.

Examples of substituents represented by $R^1$ to $R^{10}$ in General Formula 1-1 include [the substituents in] the Substituent Group A below:

<<Substituent Group A>>

Examples [of Substituent Group A] include alkyl groups (preferably with a carbon number of 1 to 30, more preferably with a carbon number of 1 to 20, and especially preferably with a carbon number of 1 to 10, such as a methyl, ethyl, isopropyl, t-butyl, n-octyl, n-decyl, n-hexadecyl, cyclopropyl, cyclopentyl, and cyclohexyl); alkenyl groups (preferably with a carbon number of 2 to 30, more preferably with a carbon number of 2 to 20, and especially preferably with a carbon number of 2 to 10, such as a vinyl, allyl, 2-butenyl, and 3-pentenyl); alkynyl groups (preferably with a carbon number of 2 to 30, more preferably with a carbon number of 2 to 20, and especially preferably with a carbon number of 2 to 10, such as propargyl and 3-pentynyl); aryl groups (preferably with a carbon number of 6 to 30, more preferably with a carbon number of 6 to 20, and especially preferably with a carbon number of 6 to 12, such as phenyl, p-methylphenyl, naphthyl, and anthranil); amino groups (preferably with a carbon number of 0 to 30, more preferably with a carbon number of 0 to 20, and especially preferably with a carbon number of 0 to 10, such as amino, methylamino, dimethylamino, diethylamino, dibenzylamino, diphenylamino, and ditolylamino); alkoxy groups (preferably with a carbon number of 1 to 30, more preferably with a carbon number of 1 to 20, and especially preferably with a carbon number of 1 to 10, such as methoxy, ethoxy, butoxy, and 2-ethylhexyloxy); aryloxy groups (preferably with a carbon number of 6 to 30, more preferably with a carbon number of 6 to 20, and especially preferably with a carbon number of 6 to 12, such as phenyloxy, 1-naphthyloxy, and 2-naphthyloxy); heterocyclic oxy groups (preferably with a carbon number of 1 to 30, more preferably with a carbon number of 1 to 20, and especially preferably with a carbon number of 1 to 12, such as pyridyloxy, pyrazyloxy, pyrimidyloxy, and quinolyloxy); acyl groups (preferably with a carbon number of 2 to 30, more preferably with a carbon number of 2 to 20, and especially preferably with a carbon number of 2 to 12, such as acetyl, benzoyl, formyl, and pivaloyl); alkoxycarbonyl groups (preferably with a carbon number of 2 to 30, more preferably with a carbon number of 2 to 20, and especially preferably with a carbon number of 2 to 12, such as methoxycarbonyl and ethoxycarbonyl); aryloxycarbonyl groups (preferably with a carbon number of 7 to 30, more preferably with a carbon number of 7 to 20, and especially preferably with a carbon number of 7 to 12, such as phenyloxycarbonyl); acyloxy groups (preferably with a carbon number of 2 to 30, more preferably with a carbon number of 2 to 20, and especially preferably with a carbon number of 2 to 10, such as acetoxy and benzoyloxy); acylamino groups (preferably with a carbon number of 2 to 30, more preferably with a carbon number of 2 to 20, and especially preferably with a carbon number of 2 to 10, such as acetylamino and benzoylamino); alkoxycarbonylamino groups (preferably with a carbon number of 2 to 30, more preferably with a carbon number of 2 to 20, and especially preferably with a carbon number of 2 to 12, such as methoxycarbonylamino); aryloxycarbonylamino groups (preferably with a carbon number of 7 to 30, more preferably with a carbon number of 7 to 20, and especially preferably with a carbon number of 7 to 12, such as phenyloxycarbonylamino); sulfonyl amino groups (preferably with a carbon number of 1 to 30, more preferably with a carbon number of 1 to 20, and especially preferably with a carbon number of 1 to 12, such as methanesulfonyl amino and benzenesulfonyl amino); sulfamoyl groups (preferably with a carbon number of 0 to 30, more preferably with a carbon number of 0 to 20, and especially preferably with a carbon number of 0 to 12, such as sulfamoyl, methylsulfamoyl, dimethylsulfamoyl, and phenylsulfamoyl); carbamoyl groups (preferably with a carbon number of 1 to 30, more preferably with a carbon number of 1 to 20, and especially preferably with a carbon number of 1 to 12, such as carbamoyl, methylcarbamoyl, diethylcarbamoyl, and phenylcarbamoyl); alkylthio groups (preferably with a carbon number of 1 to 30, more preferably with a carbon number of 1 to 20, and especially preferably with a carbon number of 1 to 12, such as methylthio and ethylthio); arylthio groups (preferably with a carbon number of 6 to 30, more preferably with a carbon number of 6 to 20, and especially preferably with a carbon number of 6 to 12, such as phenylthio); heterocyclic thio groups (preferably with a carbon number of 1 to 30, more preferably with a carbon number of 1 to 20, and especially preferably with a carbon number of 1 to 12, such as pyridylthio, 2-benzimizolylthio, 2-benzoxazolylthio, and 2-benzothiazolylthio); sulfonyl groups (preferably with a carbon number of 1 to 30, more preferably with a carbon number of 1 to 20, and especially preferably with a carbon number of 1 to 12, such as mesyl and tosyl); sulfinyl groups (preferably with a carbon number of 1 to 30, more preferably with a carbon number of 1 to 20, and especially preferably with a carbon number of 1 to 12, such as methanesulfinyl and benzenesulfinyl); ureido groups (preferably with a carbon number of 1 to 30, more preferably with a carbon number of 1 to 20, and especially preferably with a carbon number of 1 to 12, such as ureido, methylureido, and phenylureido); phosphoric amide groups (preferably with a carbon number of 1 to 30, more preferably with a carbon number of 1 to 20, and especially preferably with a carbon number of 1 to 12, such as diethylphosphoramide and phenylphosphoramide); a hydroxy group; a mercapto group; halogen atoms (such as a fluorine atom, chlorine atom, bromine atom, and iodine atom); a cyano group; a sulfo group; a carboxyl group; a nitro group; a hydroxamic acid group; a sulfino group; a hydrazino group; an imino group; heterocyclic groups (also including aromatic heterocyclic groups, preferably with a carbon number of 1 to 30 and more preferably with a carbon number of 1 to 12, with examples of the hetero atom including a nitrogen atom, an oxygen atom, a sulfur atom, a phosphorus atom, a silicon atom, a selenium atom, and a tellurium atom, and with concrete examples including pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, azepinyl group, and silolyl group); silyl groups (preferably with a carbon number of 3 to 40, more preferably with a carbon number of 3 to 30, and especially preferably with a carbon number of 3 to 24, such as trimethylsilyl and triphenylsilyl); silyloxy groups (preferably with a carbon number of 3 to 40, more preferably with a carbon number of 3 to 30, and especially preferably with a carbon number of 3 to 24, such as trimethylsilyloxy and triphenylsilyloxy); and phosphoryl groups (such as a diphenylphosphoryl group and a dimethylphosphoryl group). These substituents may be further substituted, and examples of the further substituents include groups selected from the Substituent Group A described above. Furthermore, the substituents that have been substituted with substituents may be further substituted, and examples of the further substituents include groups selected from the Substituent Group A described above. Moreover, the substituents that have been substituted with substituents that have been substituted with substituents may be further substituted, and examples of the further substituents include groups selected from the aforementioned Substituent Group A.

The material for an organic electroluminescent element of the present invention is such that at least one of $R^2$, $R^3$, $R^4$, $R^5$, $R^7$, $R^9$, and $R^{10}$ is preferably a substituent. By having a substituent in [at least one of] these positions of a pyrene ring, aggregates between the compounds expressed by General Formula 1-1 above are less likely to be produced within the light-emitting layer(s), so the purity of the blue color can be enhanced.

The material for an organic electroluminescent element of the present invention is such that at least one of $R^2$, $R^3$, $R^4$, $R^5$, $R^7$, $R^9$, and $R^{10}$ is more preferably a substituent from among an alkyl group, a silyl group, an amino group, a fluorine atom, and a phenyl group or pyridyl group that has been substituted with at least one of these groups.

In addition, it is especially preferable for at least one of $R^4$, $R^5$, $R^9$, and $R^{10}$ to be a substituent from among an alkyl group, a silyl group, an amino group, a fluorine atom, and a phenyl group or pyridyl group that has been substituted with at least one of these groups.

The material for an organic electroluminescent element of the present invention is such that $R^2$, $R^3$, $R^4$, $R^5$, $R^7$, $R^9$, and $R^{10}$ are [each] preferably an alkyl group, a silyl group, an amino group, a fluorine atom, a phenyl group or pyridyl group that has been substituted with at least one of these groups, or a hydrogen atom. By having only these substituents with the specific structures substituted at these positions of the pyrene ring, the aggregates form less readily, and changes in the chromaticity after driving can be made less than in other pyrene ring compounds or the like in which unsubstituted phenyl groups are substituted at these position, for example.

Note that the material for an organic electroluminescent element of the present invention is such that $R^1$ to $R^{10}$ preferably do not jointly form a ring. However, as long as it does not go against the spirit of the present invention, two adjacent $R^1$ to $R^{10}$ [groups] may jointly faun a five- or six-membered ring. The five- or six-membered ring that is formed may be a cycloalkenyl ring, a benzene ring, or a heteroaryl ring. Examples of heteroaryl rings include those that contain one to three hetero atoms selected from a group comprising nitrogen atoms, oxygen atoms, and sulfur atoms in the atoms constituting the ring. In concrete terms, a pyridine ring, a pyrazine ring, a pyridazine ring, a pyrimidine ring, an imidazole ring, an oxazole ring, a thiazole ring, a pyrazole ring, a thiophene ring, a furan ring, and the like can be cited as examples. The five- or six-membered ring that is formed may have a substituent, and examples of substituents on a carbon atom include [those listed in] the aforementioned Substituent Group A, while examples of substituents on a nitrogen atom include [those listed in] the following Substituent Group B.

<Substituent Group B>>

[Examples of Substituent Group B include] alkyl groups (preferably with a carbon number of 1 to 30, more preferably with a carbon number of 1 to 20, and especially preferably with a carbon number of 1 to 10, such as methyl, ethyl, isopropyl, t-butyl, n-octyl, n-decyl, n-hexadecyl, cyclopropyl, cyclopentyl, and cyclohexyl); alkenyl groups (preferably with a carbon number of 2 to 30, more preferably with a carbon number of 2 to 20, and especially preferably with a carbon number of 2 to 10, such as vinyl, allyl, 2-butenyl, and 3-pentenyl); alkynyl groups (preferably with a carbon number of 2 to 30, more preferably with a carbon number of 2 to 20, and especially preferably with a carbon number of 2 to 10, such as propargyl and 3-pentynyl); aryl groups (preferably with a carbon number of 6 to 30, more preferably with a carbon number of 6 to 20, and especially preferably with a carbon number of 6 to 12, such as phenyl, p-methylphenyl, naphthyl, and anthranil); a cyano group; heterocyclic groups (also including aromatic heterocyclic groups, preferably with a carbon number of 1 to 30 and more preferably with a carbon number of 1 to 12, with examples of the hetero atom including a nitrogen atom, an oxygen atom, a sulfur atom, a phosphorus atom, a silicon atom, a selenium atom, and a tellurium atom, and with concrete examples including pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, azepinyl group, and silolyl group). These substituents may be further substituted, and examples of the further substituents include groups selected from the Substituent Group B described above. Furthermore, the substituents that have been substituted with substituents may be further substituted, and examples of the further substituents include groups selected from the Substituent Group B described above. Moreover, the substituents that have been substituted with substituents that have been substituted with substituents may be further substituted, and examples of the further substituents include groups selected from the aforementioned Substituent Group B.

In General Formula 1-1 above, at least one of $R^1$ to $R^{10}$ is a substituent expressed by General Formula 1-2 below:

[Eleventh Chemical Formula]

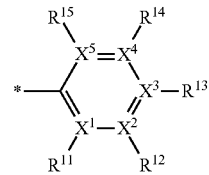

General Formula 1-2

In General Formula 1-2 above, the asterisk indicates the bonding position with a pyrene ring.

In General Formula 1-2 above, $X^1$ to $X^5$ represent each independently a carbon atom or a nitrogen atom, and at least one of $X^1$ to $X^5$ is a nitrogen atom. However, if $X^1$ to $X^5$ represent nitrogen atoms, there is no $R^{11}$ to $R^{15}$ bonded on these nitrogen atoms.

There are no particular restrictions on the position(s) of the nitrogen atom(s) in $X^1$ to $X^5$.

The number of nitrogen atoms in $X^1$ to $X^5$ is preferably from 1 to 3 from the standpoint of chemical stability of the compound and more preferably 2 or 3 from the standpoint of further enhancing the purity of the blue color.

When two or more of $X^1$ to $X^5$ in General Formula 1-2 above represent carbon atoms, the respective substituents belonging to two adjacent carbon atoms of these (corresponding ones of $R^{11}$ to $R^{15}$) preferably do not jointly form a five- or six-membered ring in the present invention, but they may jointly form a five- or six-membered ring. The five- or six-membered ring that is formed may be a cycloalkenyl ring, a benzene ring, or a heteroaryl ring. Examples of heteroaryl rings includes those that contain one to three hetero atoms selected from a group comprising nitrogen atoms, oxygen atoms, and sulfur atoms in the atoms constituting the ring. In concrete terms, a pyridine ring, a pyrazine ring, a pyridazine ring, a pyrimidine ring, an imidazole ring, an oxazole ring, a thiazole ring, a pyrazole ring, a thiophene ring, a furan ring, and the like can be cited as examples. The five- or six-membered ring that is formed may have a substituent, and examples of substituents on a carbon atom include [those listed in] the aforementioned Substituent Group A, while examples of substituents on a nitrogen atom include [those listed in] the aforementioned Substituent Group B. The five- or six-membered ring that is formed is preferably a benzene ring and more preferably an unsubstituted benzene ring.

In General Formula 1-2 above, $R^{11}$ to $R^{15}$ represent each independently a hydrogen atom or a substituent, and at least one of $R^{11}$ to $R^{15}$ represents an alkyl group or a silyl group. Furthermore, it is preferable if at least one of $R^{11}$ to $R^{15}$ represents an alkyl group.

The alkyl group represented by at least one of $R^{11}$ to $R^{15}$ is preferably an unsubstituted linear alkyl group, an unsubstituted branched alkyl group, an unsubstituted cycloalkyl group, or a perfluoroalkyl group, more preferably a $C_1$ to $C_6$ linear alkyl group, a $C_1$ to $C_6$ branched alkyl group, a $C_1$ to $C_6$ perfluoroalkyl group, and especially preferably a methyl group, an ethyl group, an isopropyl group, a t-butyl group, a t-amyl group, a neopentyl group, or a trifluoromethyl group, with a methyl group, an ethyl group, an isopropyl group, or a t-butyl group being even more especially favorable.

The silyl group represented by at least one of $R^{11}$ to $R^{15}$ is preferably an alkylsilyl group and more preferably a trialkylsilyl group. The alkyl groups of the aforementioned trialkylsilyl group are preferably each independently a methyl group, an ethyl group, and an isopropyl group, with a methyl group being more preferable. The silyl group represented by at least one of $R^{11}$ to $R^{15}$ is especially preferably a trimethylsilyl group.

$R^{11}$ to $R^{15}$ may have a substituent other than an alkyl group or a silyl group to the extent that does not go against the spirit of the present invention. Those listed in the aforementioned Substituent Group A can be cited as examples of substituents that $R^{11}$ to $R^{15}$ can take. The substituents that $R^{11}$ to $R^{15}$ can take are preferably substituents having a fluorine atom, an alkyl group, a silyl group, an aryl group, a cyano group, or an amino group. Concrete examples include an alkyl group, a perfluoroalkyl group, an aryl group, an alkoxy group, a fluorine atom, a cyano group, a diarylamino group, and a trialkylsilyl group. With the material for an organic electroluminescent element of the present invention, it is more preferable for $R^{11}$ to $R^{15}$ to represent each independently a hydrogen atom, an alkyl group, or a silyl group from the standpoint of further enhancing the purity of the blue color.

Nitrogen-containing aromatic heterocycles are such that the carbon atoms adjacent to the N atoms constituting the heterocycles are active sites for reactions, and it is preferable if the carbon atoms adjacent to the N atoms have substituents because the chemical stability is increased in oxidation/reduction and in the excited state. It is more preferable if there are substituents at the carbon atoms adjacent to the N atoms on both sides. In particular, by introducing alkyl groups or silyl groups to the carbon atoms adjacent to the N atoms on both sides, the chemical stability is increased in oxidation/reduction and in the excited state without reducing the color purity, and changes in the chromaticity after driving can be made smaller. Moreover, it is more stable if they are alkyl groups. From such standpoints, in General Formula 1-2 above in General Formula 1-1 above, it is preferable if at least one of $X^1$, $X^3$, and $X^5$ is a nitrogen atom and also both $X^2$ and $X^4$ are carbon atoms. In this case, it is preferable if at least one of $R^{12}$ and $R^{14}$ is an alkyl group or a silyl group, and it is more preferable if both of $R^{12}$ and $R^{14}$ are alkyl groups or silyl groups. In addition, it is more preferable for $R^{12}$ and $R^{14}$ to be alkyl groups rather than silyl groups.

The compound expressed by General Formula 1-1 above is preferably a compound in which at least three locations of $R^1$ to $R^{10}$ are substituted with an alkyl group, a silyl group, an amino group, a fluorine atom, an aryl group or nitrogen-containing heterocyclic group that has been substituted with at least one of these groups, or a substituent expressed by General Formula 1-2 above from the standpoint of being able to suppress aggregation between pyrene-based compounds. There are no restrictions on the number of ring members of this aryl group or this nitrogen-containing heterocyclic group, but from the standpoint of suppressing aggregation, the number of ring members is preferably somewhat small, with 5 to 12 ring members being preferable, and 6 to 10 being more preferable.

Furthermore, from the standpoint of being able to suppress aggregation of pyrene-based compounds with each other, the compound expressed by General Formula 1-1 above is preferably a compound in which at least three locations of $R^1$ to $R^{10}$ are substituted with an alkyl group, a silyl group, an amino group, a fluorine atom, a phenyl group or pyridyl group that has been substituted with at least one of these groups, or a substituent expressed by General Formula 1-2 above, more preferably a compound in which three to five locations of $R^1$ to $R^{10}$ are substituted with any of these substituents, especially preferably a compound in which three or four locations of $R^1$ to $R^{10}$ are substituted with any of these substituents, and yet more especially preferably a compound in which four locations of $R^1$ to $R^{10}$ are substituted with any of these substituents.

Of these, it is more preferable if the compound expressed by General Formula 1-1 above is such that at least one of $R^2$ to $R^{10}$ is an ortho-alkyl-substituted phenyl group from the standpoints of good chemical stability and a high aggregation suppression effect without lowering color purity. It is even more preferable if the aforementioned ortho-alkyl-substituted phenyl group is an o-tolyl group, a 2,6-xylyl group, or a mesityl group.

The compound expressed by General Formula 1-1 is preferably a compound expressed by General Formula 2 below:

[Twelfth Chemical Formula]

General Formula 2

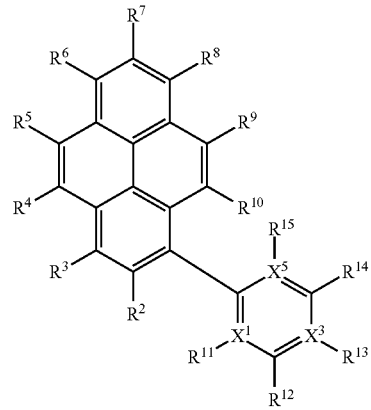

In General Formula 2, in General Formula 2, [sic] $R^2$ to $R^{10}$ represent each independently a hydrogen atom or a substituent. $X^1$, $X^3$, and $X^5$ represent each independently a carbon atom or a nitrogen atom, and at least one of $X^1$, $X^3$, and $X^5$ is a nitrogen atom. $R^{11}$ to $R^{15}$ represent each independently a hydrogen atom or a substituent, and at least one of $R^{11}$ to $R^{15}$ represents an alkyl group or a silyl group, but if $X^1$, $X^3$, and $X^5$ represent nitrogen atoms, there is no $R^{11}$, $R^{13}$, or $R^{15}$ bonded on these nitrogen atoms. However, a pyrene skeleton is never contained in $R^2$ to $R^{15}$, and even when $R^{11}$ to $R^{15}$ jointly form a ring, a pyrene skeleton is never formed.

The description and preferred ranges of $R^2$ to $R^{10}$ in General Formula 2 are the same as the description and preferred ranges of $R^1$ to $R^{10}$ in General Formula 1-1 above. The description and preferred ranges of $X^1$, $X^3$, and $X^5$ in General Formula 2 are the same as the description and preferred ranges of $X^1$ to $X^5$ in the description of General Formula 1-1 above. The description and preferred ranges of $R^{11}$ to $R^{15}$ in General Formula 2 are the same as the description and preferred ranges of $R^{11}$ to $R^{15}$ in General Formula 1-1 above.

The compound expressed by General Formula 1-1 above is preferably a compound expressed by any of General Formulas 3-1 to 3-3 below:

[Thirteenth Chemical Formula]

General Formula 3-1

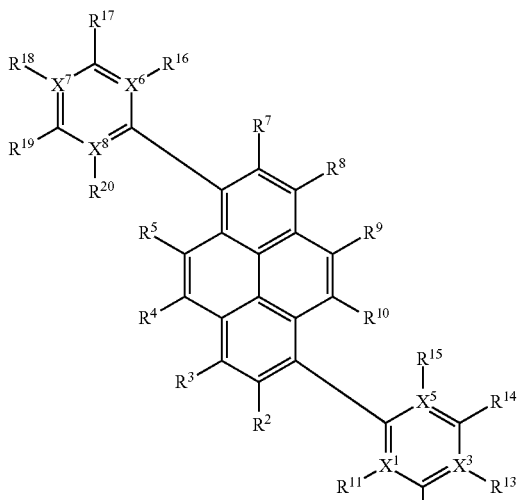

General Formula 3-2

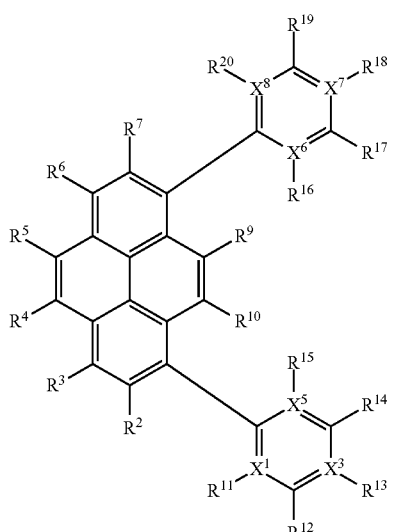

General Formula 3-3

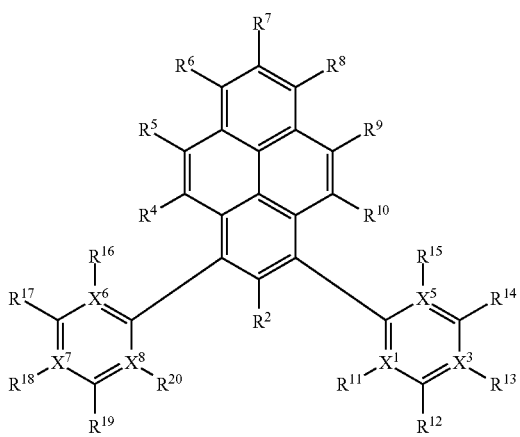

In General Formulas 3-1 to 3-3 above, $R^2$ to $R^{10}$ represent each independently a hydrogen atom or a substituent. $X^1$, $X^3$, and $X^5$ represent each independently a carbon atom or a nitrogen atom, and at least one of $X^1$, $X^3$, and $X^5$ is a nitrogen atom. $R^{11}$ to $R^{15}$ represent each independently a hydrogen atom or a substituent, and at least one of $R^{11}$ to $R^{15}$ represents an alkyl group or a silyl group. At least one of $X^6$ to $X^8$ is a nitrogen atom. $R^{16}$ to $R^{20}$ represent each independently a hydrogen atom or a substituent, and at least one of $R^{16}$ to $R^{20}$ represents an alkyl group or a silyl group, but if $X^1$, $X^3$, $X^5$, and $X^6$ to $X^8$ represent nitrogen atoms, there is no $R^{11}$, $R^{13}$, $R^{15}$, $R^{16}$, $R^{18}$, or $R^{20}$ bonded on these nitrogen atoms. However, a pyrene skeleton is never contained in $R^2$ to $R^{20}$, and even when $R^{11}$ to $R^{15}$ jointly form a ring, or even when $R^{16}$ to $R^{20}$ jointly form a ring, a pyrene skeleton is never formed.

The description and preferred ranges of $R^2$ to $R^5$ and $R^7$ to $R^{10}$ in General Formula 3-1 are the same as the description and preferred ranges of $R^1$ to $R^{10}$ in General Formula 1-1 above. The description of $X^1$, $X^3$, and $X^5$ to $X^8$ in General Formula 3-1 is the same as the description of $X^1$ to $X^5$ in the description of General Formula 1-1 above, and the preferred ranges thereof are also the same, except for the addition of the fact that at least two of $X^1$, $X^3$, and $X^5$ are nitrogen atoms. The description of $R^{11}$ to $R^{20}$ in General Formula 3-1 are the same as the description of $R^{11}$ to $R^{15}$ in General Formula 1-1 above, and the preferred ranges thereof are also the same, except for the addition of the fact that $R^{11}$ to $R^{20}$ represent each independently a hydrogen atom, an alkyl group, or a silyl group.

The description and preferred ranges of $R^2$ to $R^7$, $R^9$, and $R^{10}$ in General Formula 3-2 are the same as the description and preferred ranges of $R^1$ to $R^{10}$ in General Formula 1-1 above. The description and preferred ranges of $X^1$, $X^3$, and $X^5$ to $X^8$ in General Formula 3-2 are the same as the description and preferred ranges of $X^1$, $X^3$, and $X^5$ to $X^8$ in the description of General Formula 3-1 above. The description and preferred ranges of $R^{11}$ to $R^{20}$ in General Formula 3-2 are the same as the description and preferred ranges of $R^{11}$ to $R^{20}$ in the description of General Formula 3-1 above.

The description and preferred ranges of $R^2$ and $R^4$ to $R^{10}$ in General Formula 3-3 are the same as the description and preferred ranges of $R^1$ to $R^{10}$ in General Formula 1-1 above. The description and preferred ranges of $X^1$, $X^3$, and $X^5$ to $X^8$ in General Formula 3-3 are the same as the description and preferred ranges of $X^1$, $X^3$, and $X^5$ to $X^8$ in the description of General Formula 3-1 above. The description and preferred ranges of $R^{11}$ to $R^{20}$ in General Formula 3-3 are the same as the description and preferred ranges of $R^{11}$ to $R^{20}$ in the description of General Formula 3-1 above.

The compound expressed by General Formula 1-1 above is preferably a compound expressed by General Formula 3-1 above from among the compounds expressed by General Formulas 3-1 to 3-3 above.

When a compound expressed by General Formula 1-1 above is used as a light-emitting material, the maximum emission wavelength of the organic electroluminescent element is usually less than 455 nm. It is preferably at least 400 nm and less than 455 run, more preferably at least 420 nm and less than 455 nm, and even more preferably at least 430 nm and less than 455 nm, and from the standpoint of being able to obtain blue light emission with high color purity, it is most preferably at least 440 nm and less than 455 nm.

The compound expressed by General Formula 1-1 above preferably has a molecular weight of 1000 or lower, more preferably 900 or lower, especially preferably 850 or lower, and even more preferably 800 or lower. Lowering the molecular weight allows the sublimation temperature to be lowered, so pyrolysis of the compound in vapor deposition can be prevented. Furthermore, this makes it possible to shorten the vapor deposition time and to suppress energy required for vapor deposition. Here, with a material that has a high sublimation temperature, pyrolysis can occur during vapor deposition for an extended period of time, so the sublimation temperature is preferably not too high from the standpoint of vapor deposition suitability. The sublimation temperature of the compound expressed by General Formula 1-1 above (meaning the temperature lowering 10 wt % in this Specification) is preferably 300° C., more preferably 285° C. or lower, and even more preferably 270° or lower.

Concrete examples of the compound expressed by General Formula 1-1 above will be given below, but it should not be construed that the compounds expressed by General Formula 1-1 that can be used in the present invention are limited to or by these concrete examples:

[Fourteenth Chemical Formula]

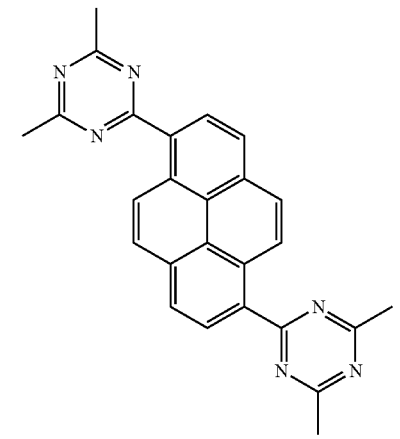

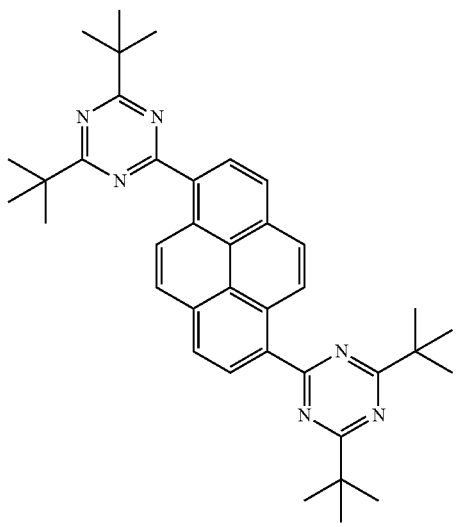

-continued

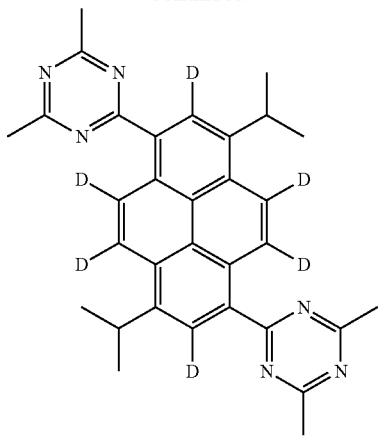

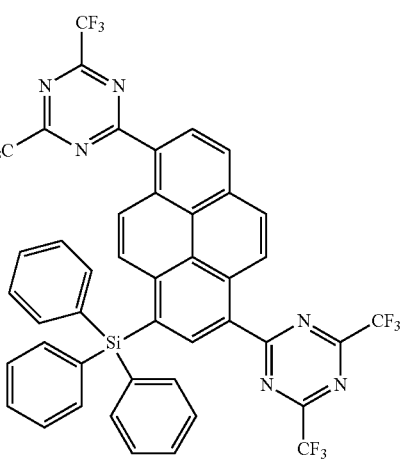

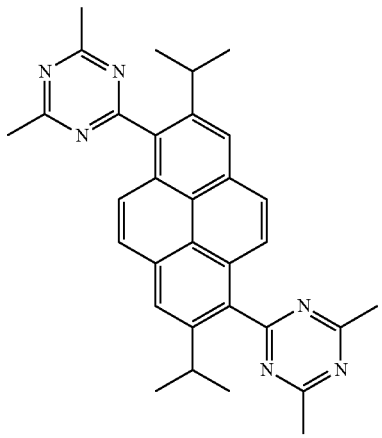

25
-continued
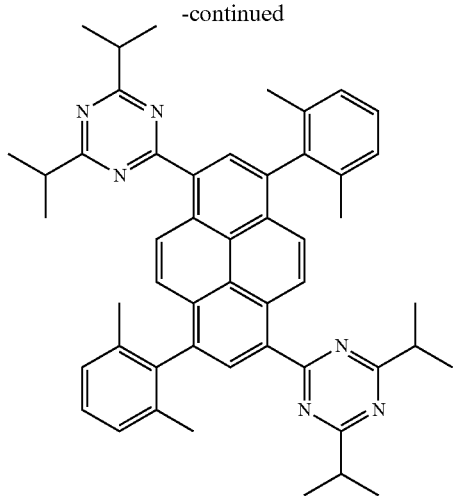
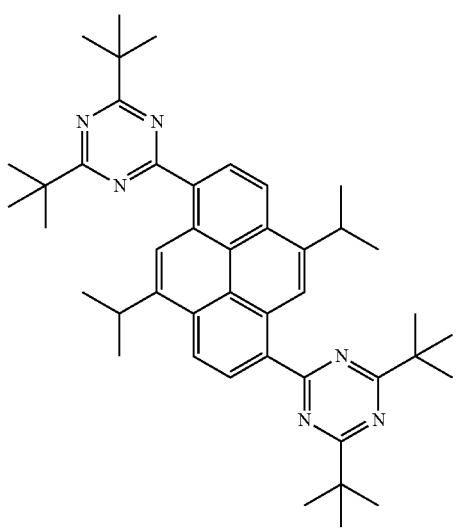
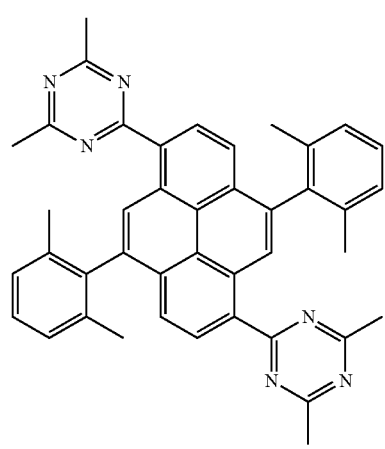
26
-continued
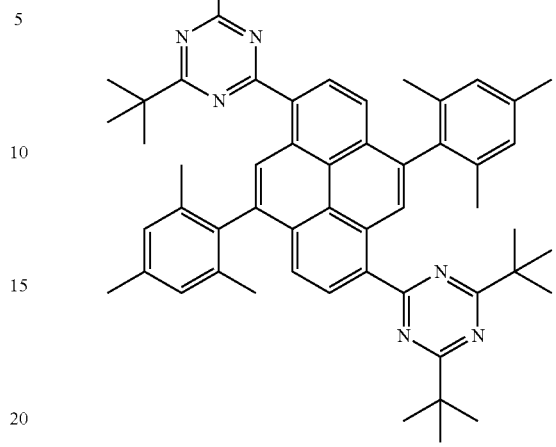
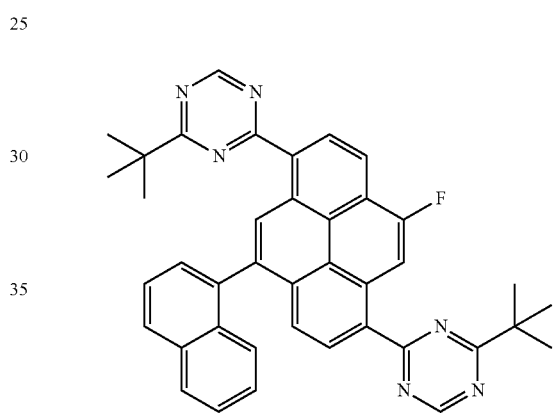
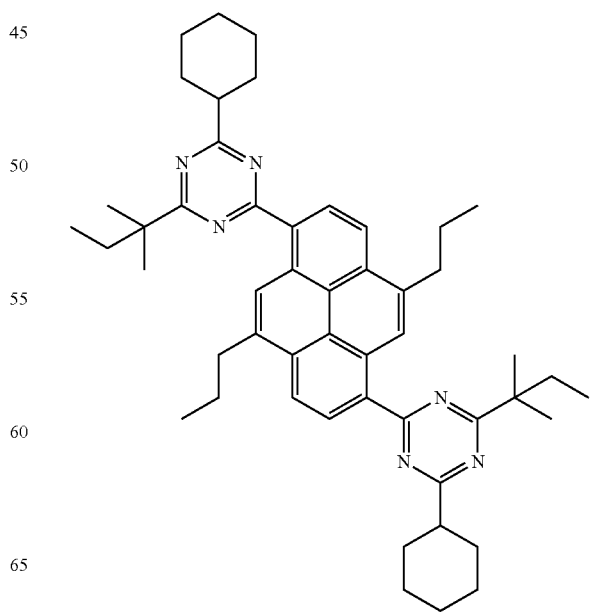

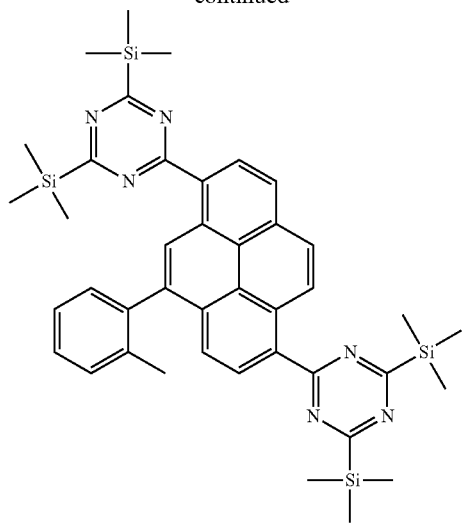
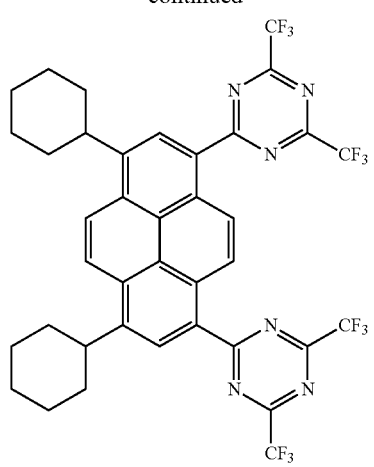
[Fifteenth Chemical Formula]
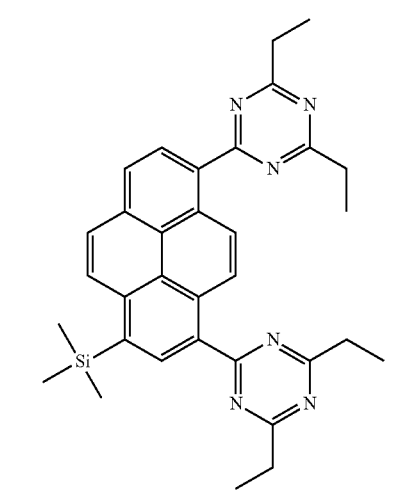
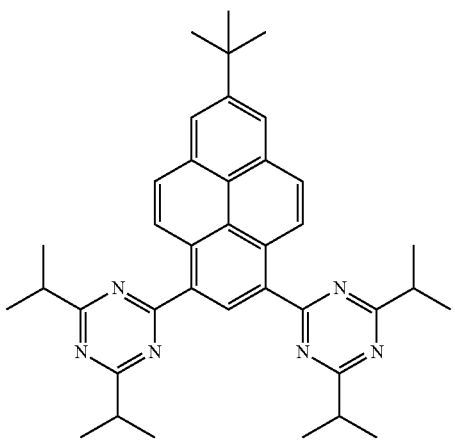
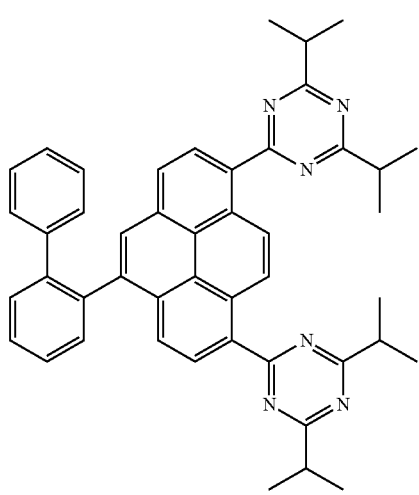
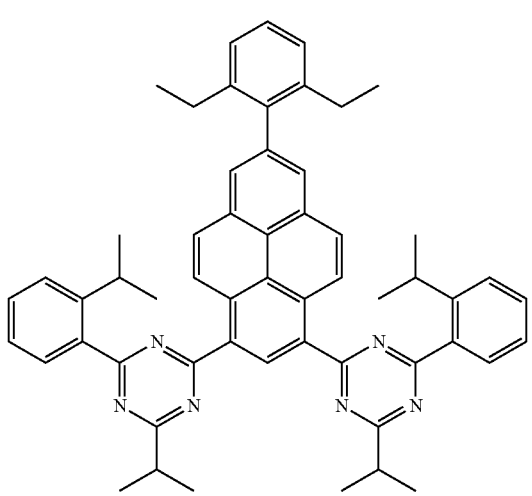

29
-continued
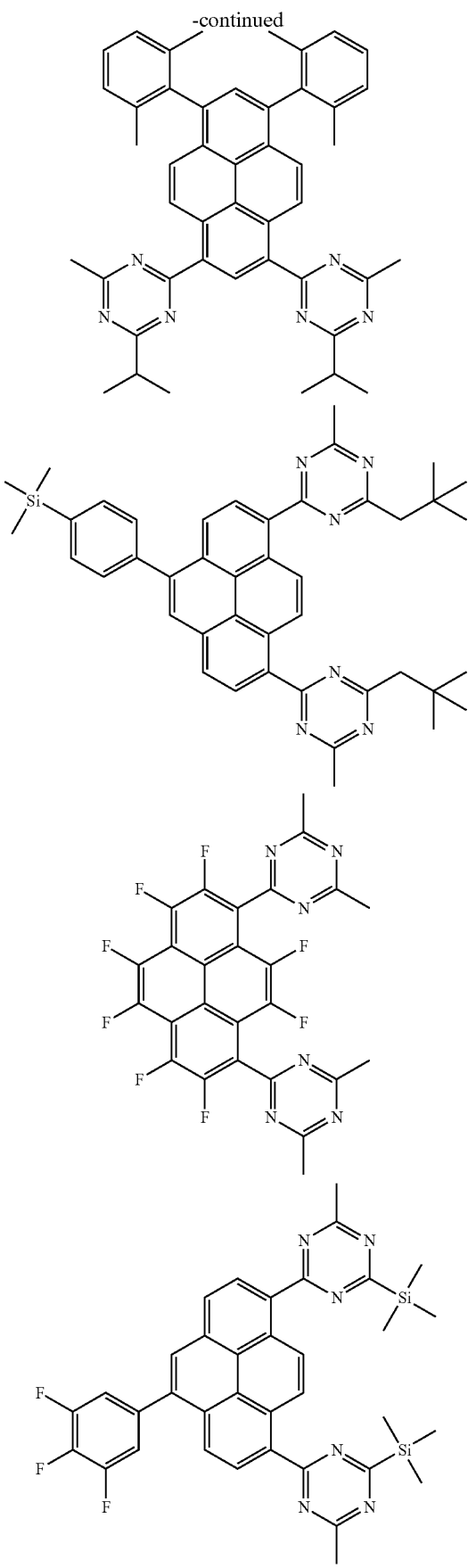
30
-continued
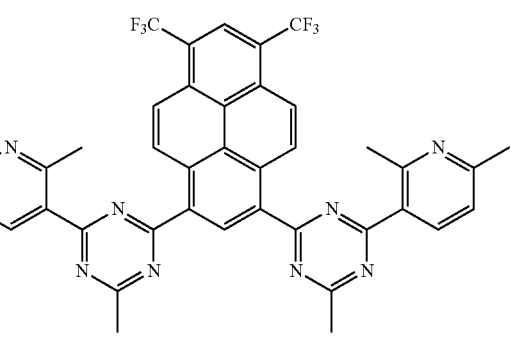
[Sixteenth Chemical Formula]

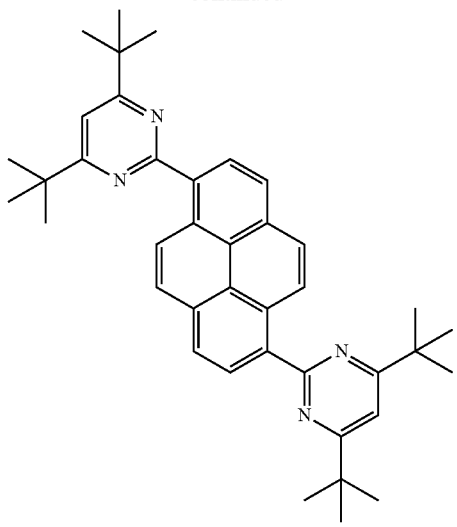
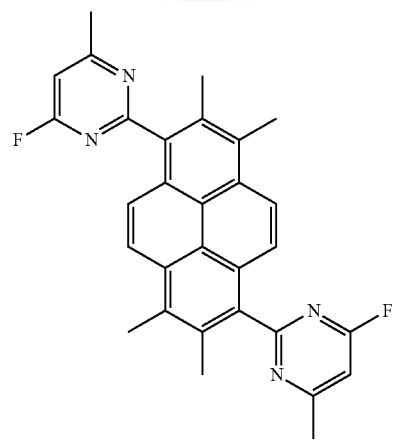
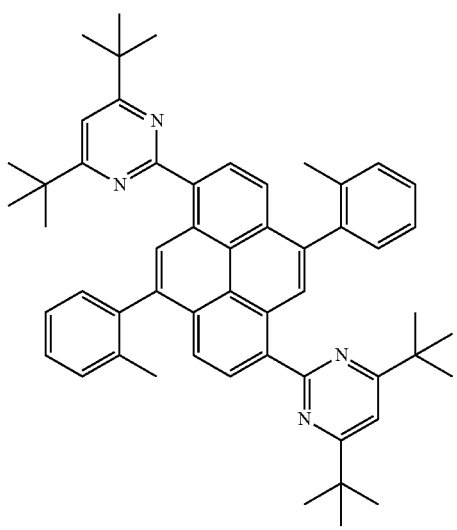
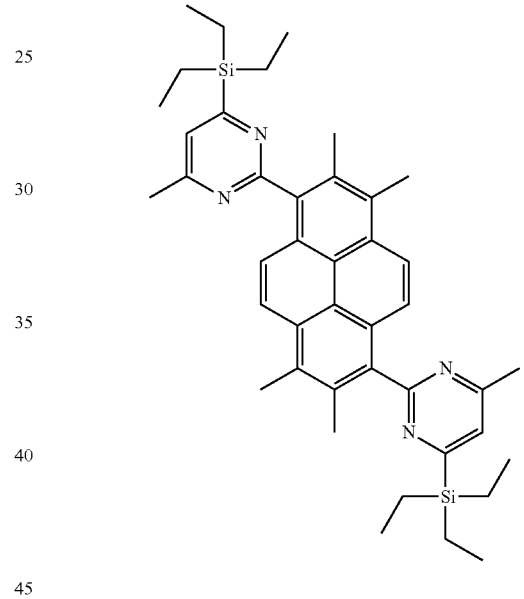
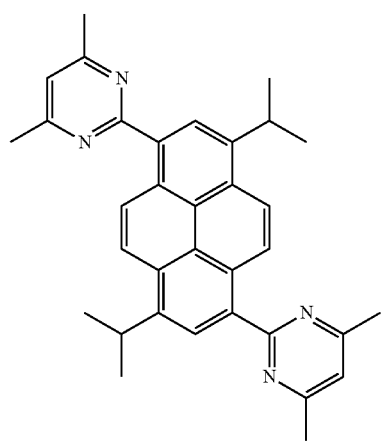
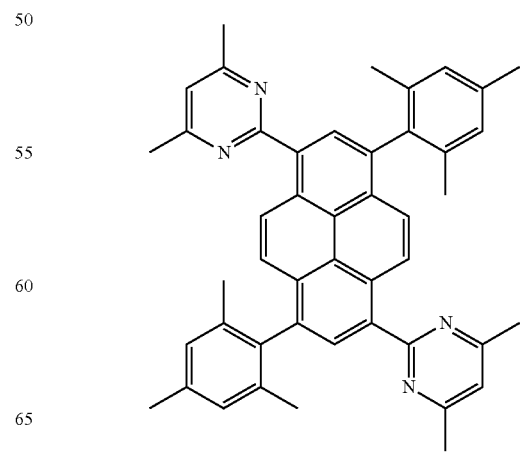

33
-continued
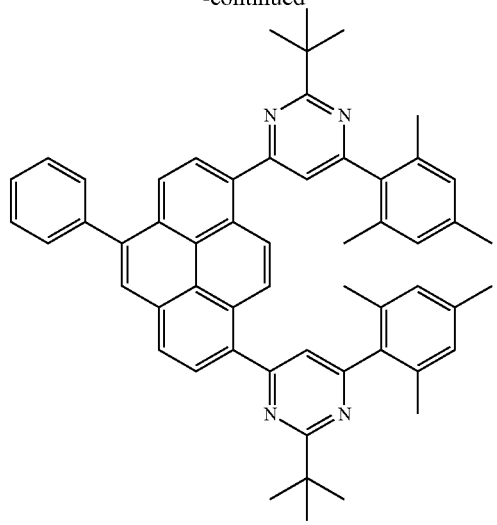
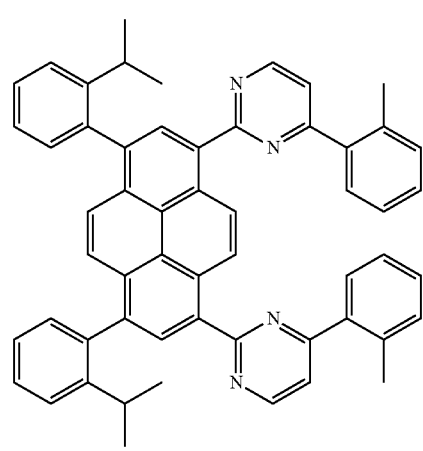
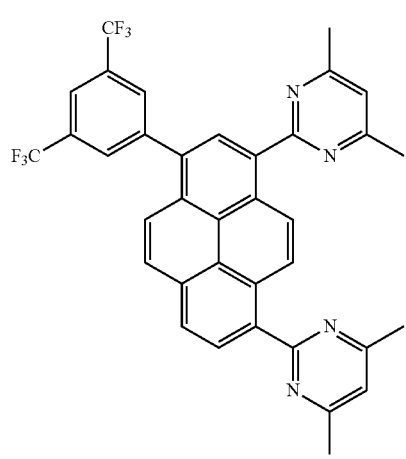
34
-continued
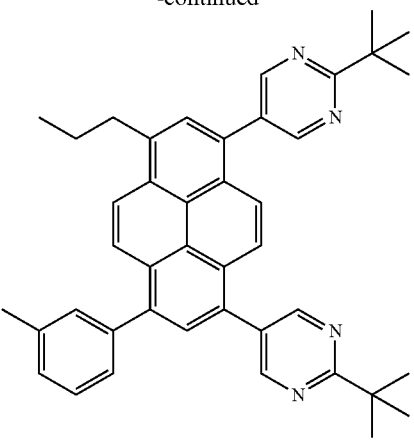
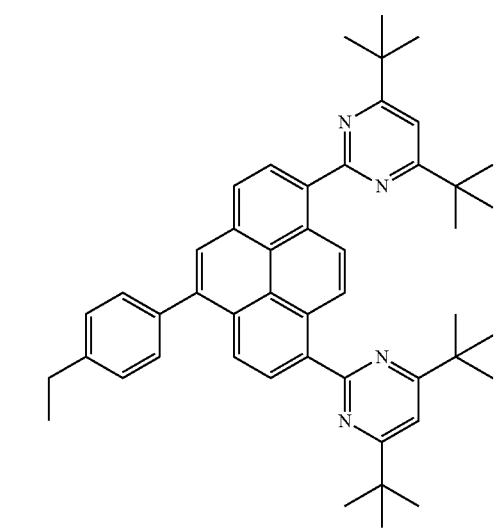
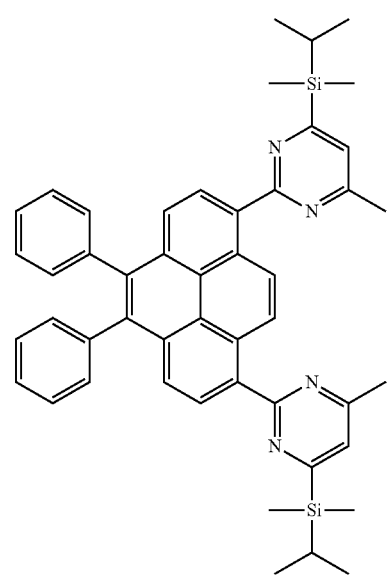

[Seventeenth Chemical Formula]
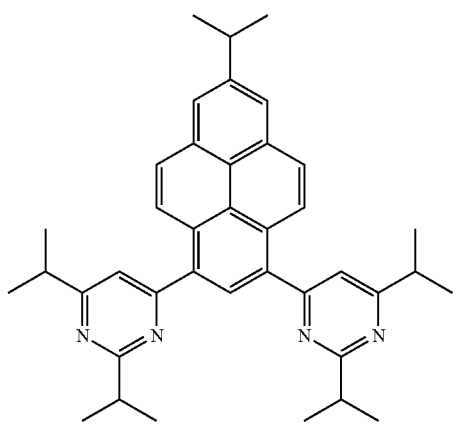
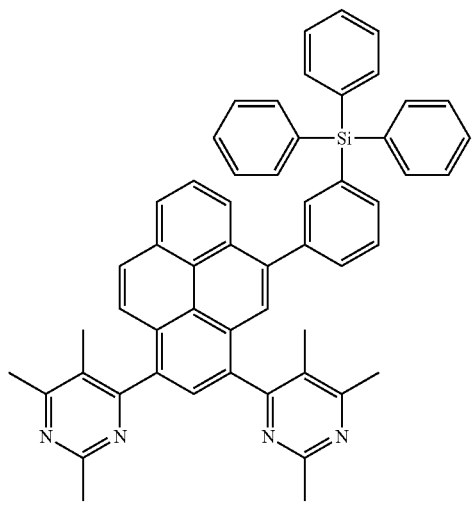
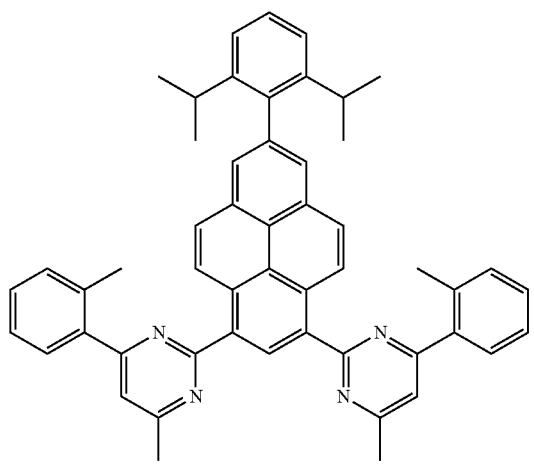
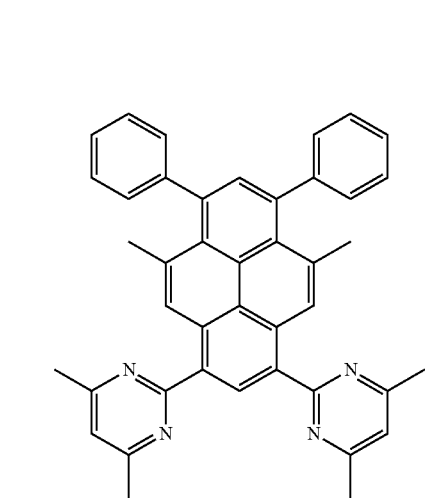
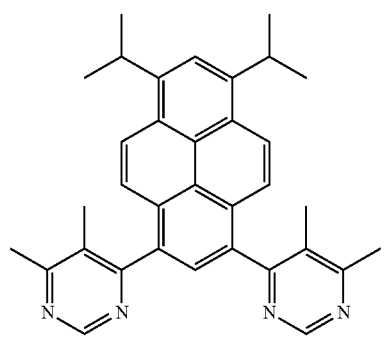
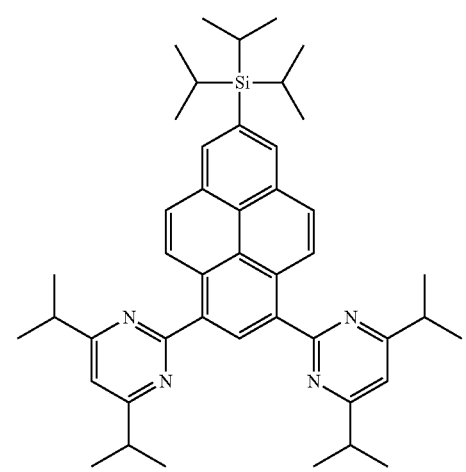

37
-continued
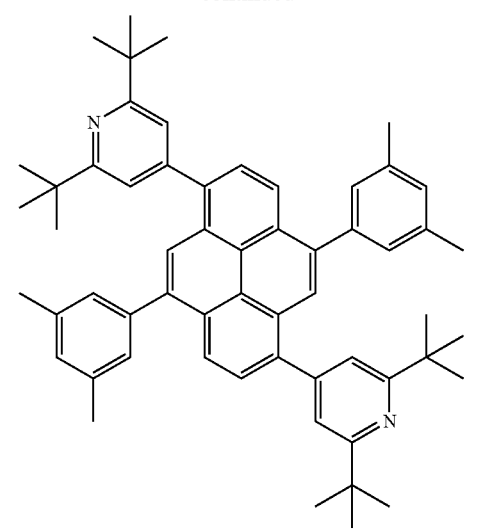
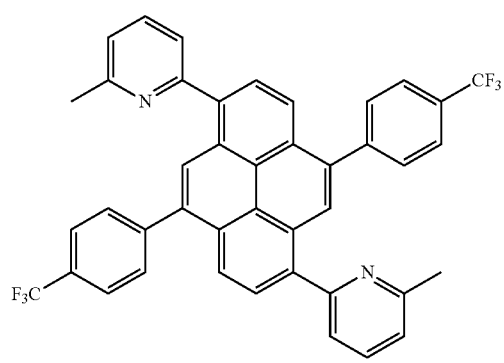
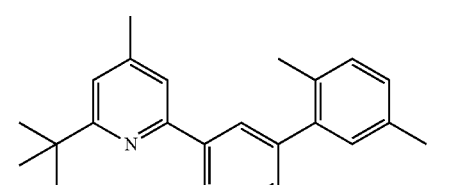
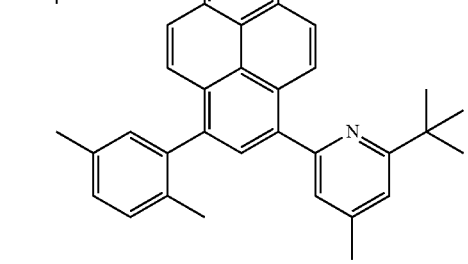
38
-continued
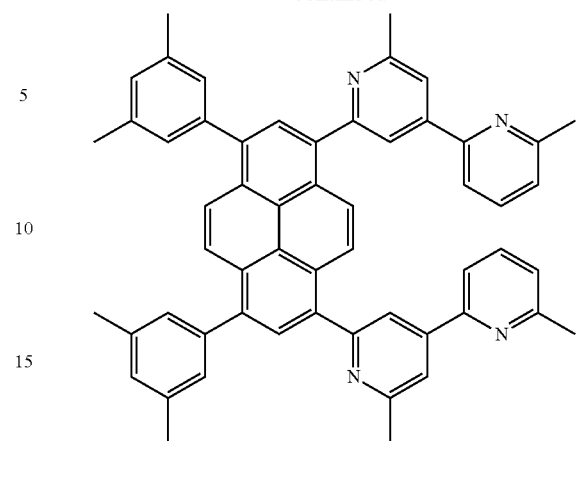
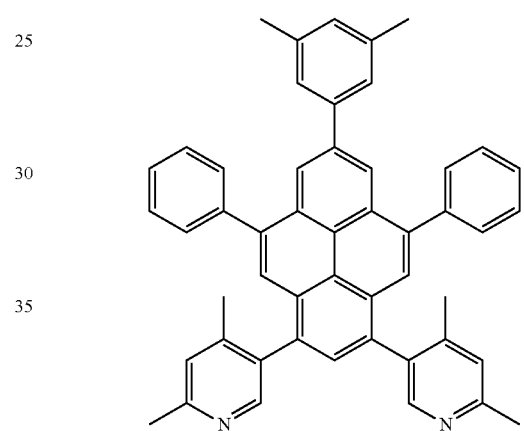
[Eighteenth Chemical Formula]
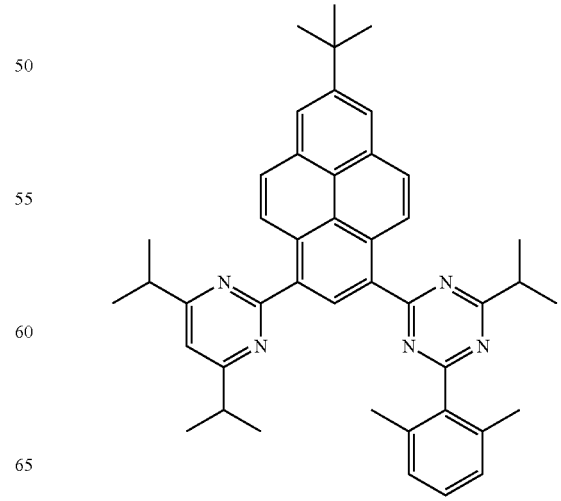

-continued
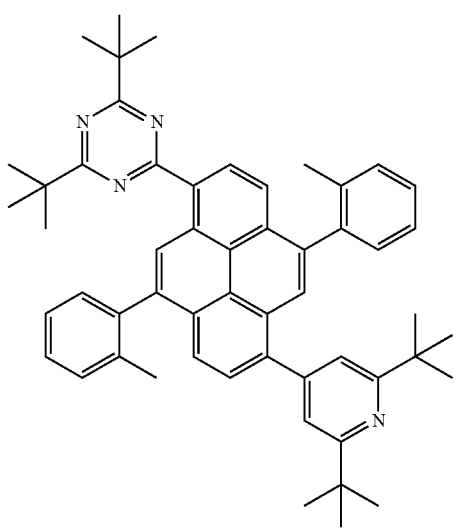
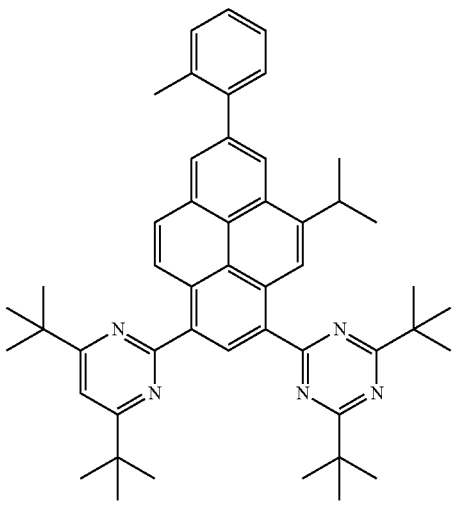
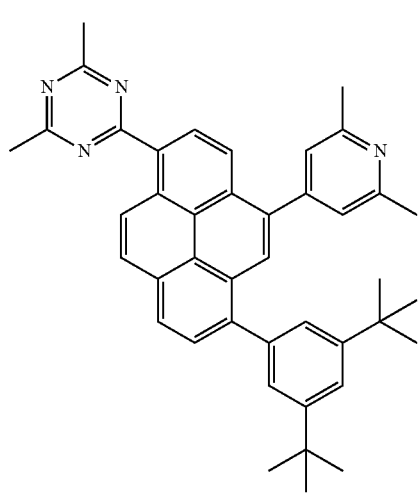
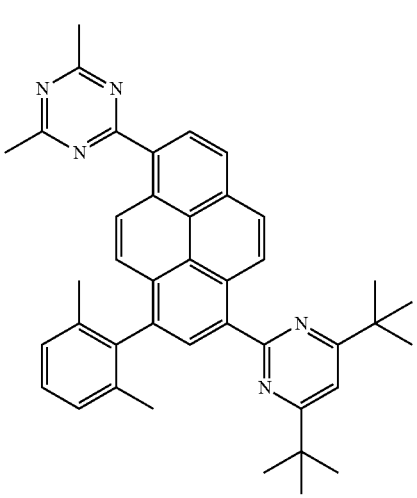
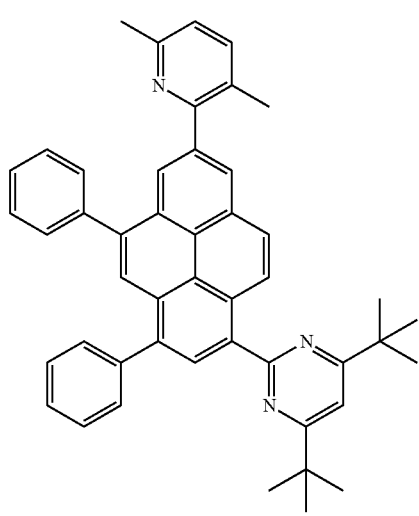
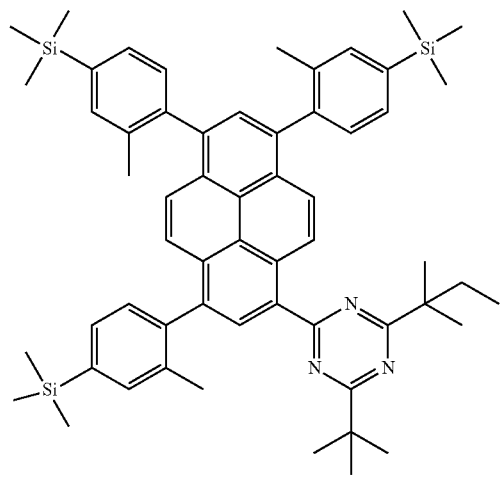

41
-continued
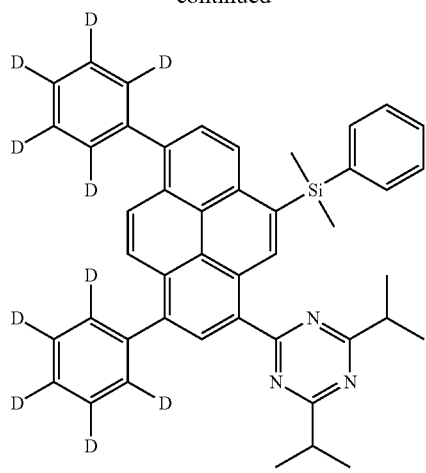
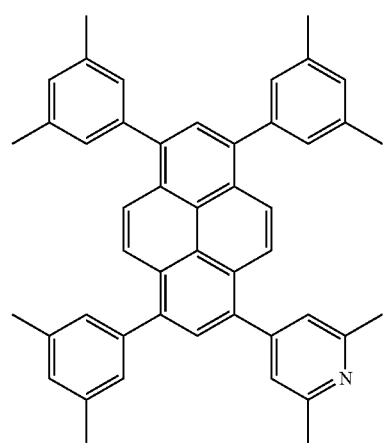
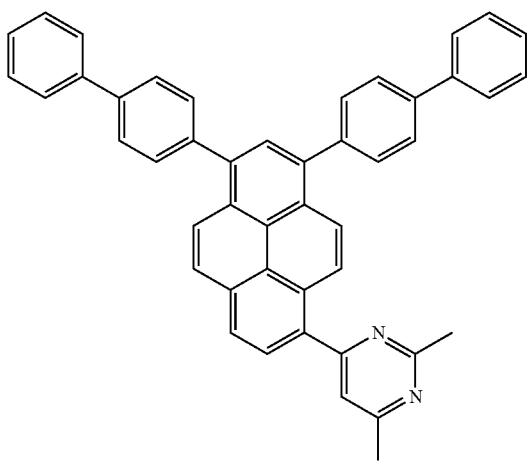
42
-continued
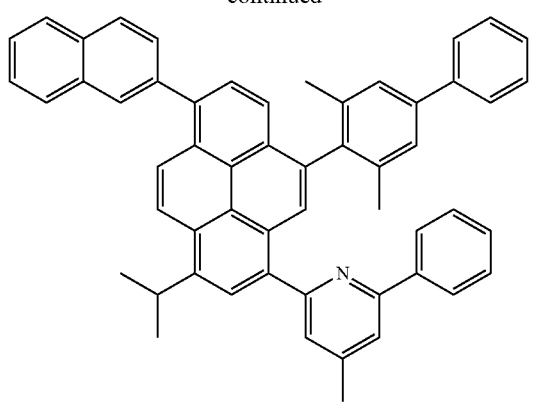
[Nineteenth Chemical Formula]
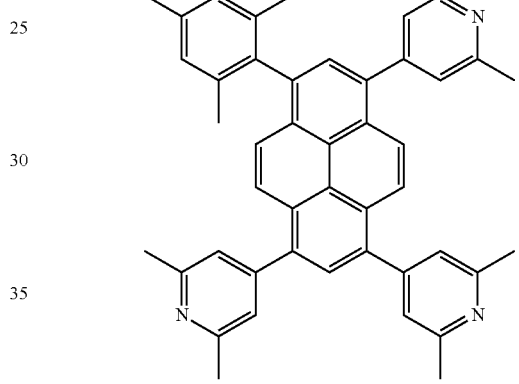
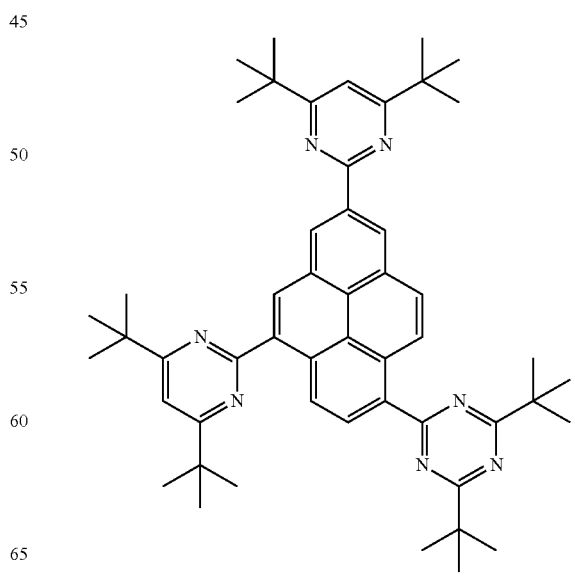

-continued
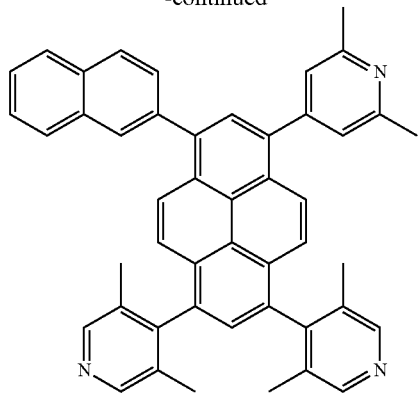
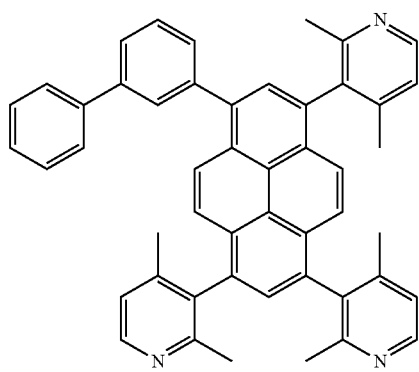
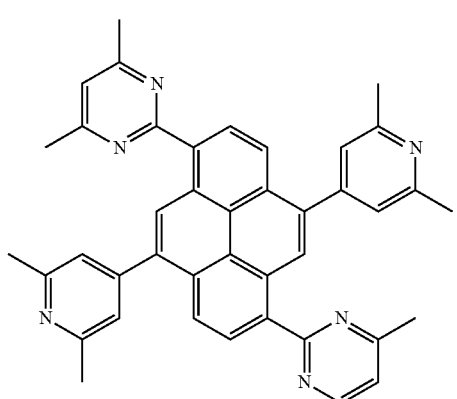
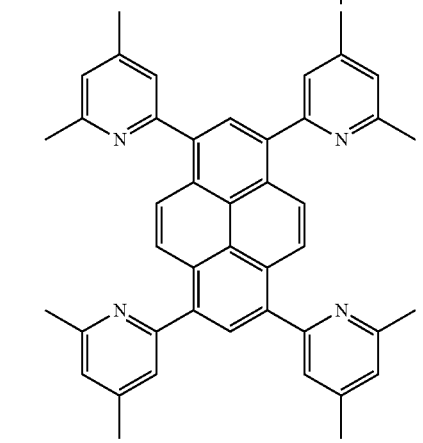
-continued
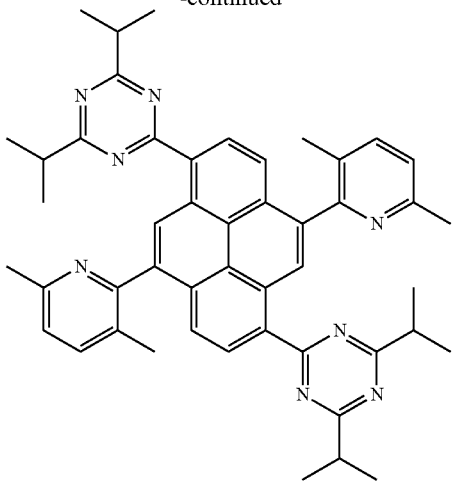
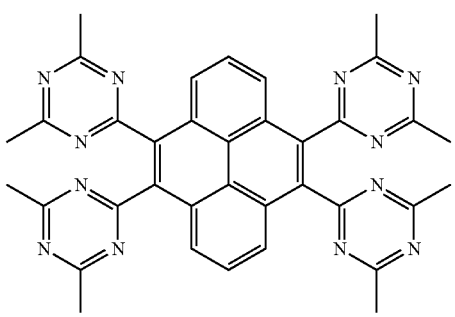
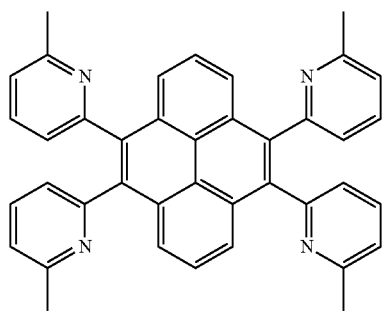
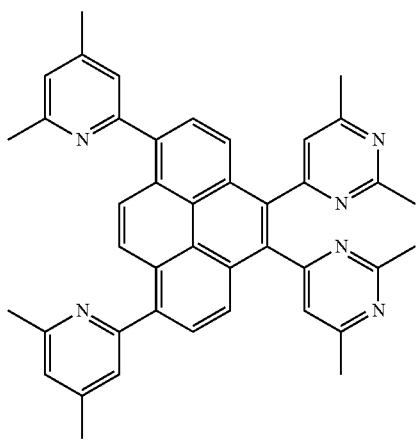

-continued
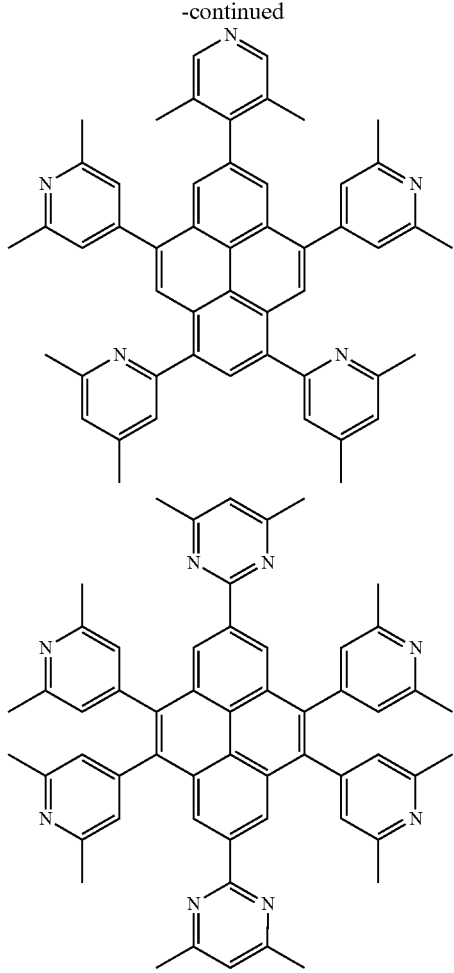
[Twentieth Chemical Formula]
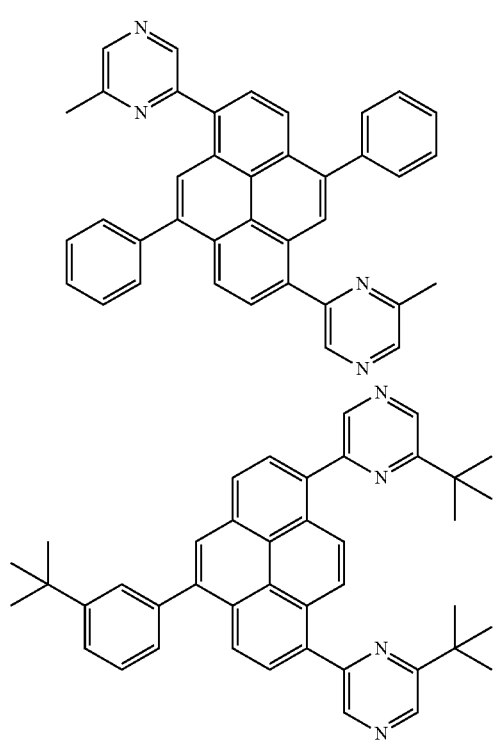
-continued
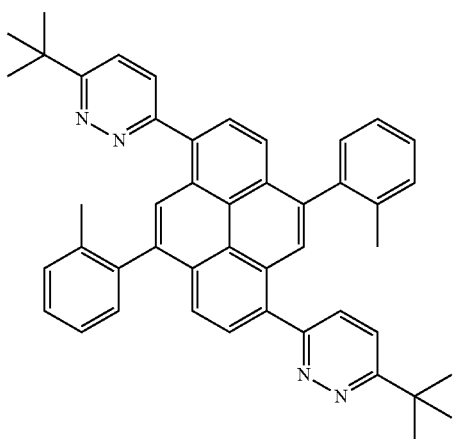
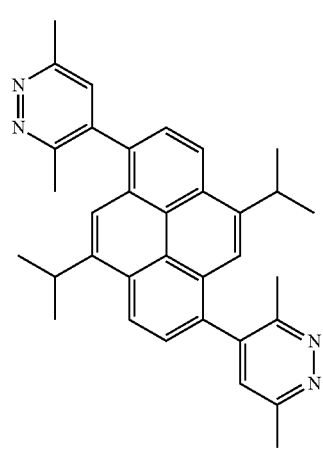

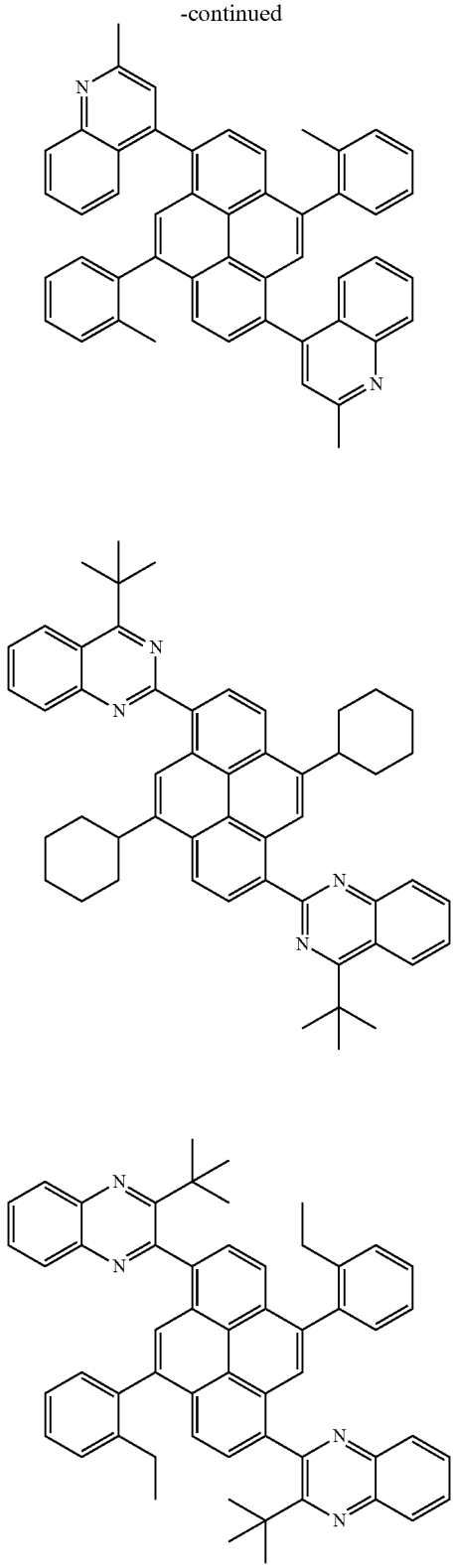

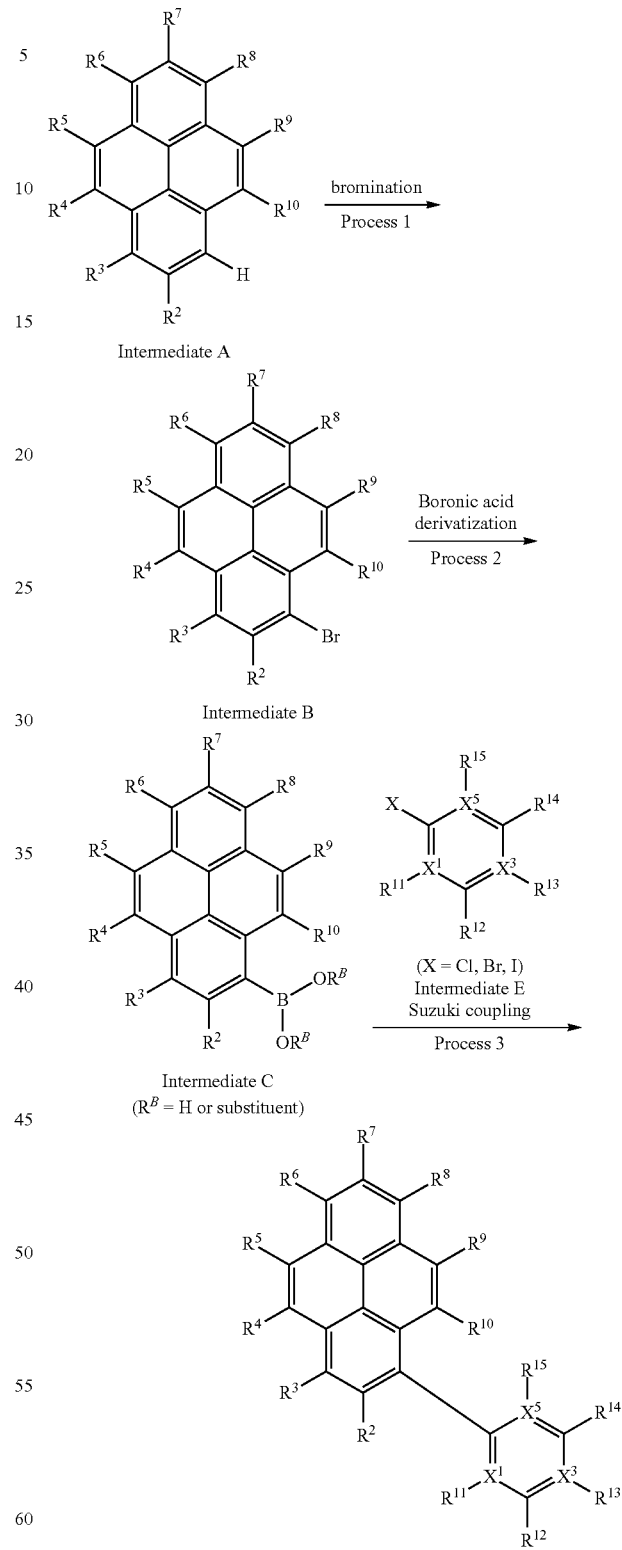

[Twenty-First Chemical Formula]

Intermediate A

Intermediate B

Intermediate C
($R^B$ = H or substituent)

(X = Cl, Br, I)
Intermediate E
Suzuki coupling
Process 3 target compound
Intermediate D

The compounds expressed by General Formula 1-1 above can be synthesized by the methods described in Japanese Laid-Open Patent Applications 2010-138121 and 2011-14886, WO 2010/113743, and the like, or by a combination of other publicly known reactions. Moreover, they can be synthesized by the following scheme, for example:

The synthetic intermediate A having a variety of substituents can be synthesized by a combination of publicly known reactions. For example, a compound having substituents at $R^2$ and $R^7$ can be synthesized by the methods described in Japanese Laid-Open Patent Applications 2008-101182 and 2008-127291 and the like. A compound having substituents at $R^3$, $R^6$, and $R^8$ can be synthesized by the methods described in Japanese Laid-Open Patent Applications 2006-176494, 2009-4351, and 2009-35516, WO 2005/108348, and the like. A compound having substituents at $R^4$, $R^5$, $R^9$, and $R^{10}$ can be synthesized by the methods described in Japanese Laid-Open Patent Application 2008-127291, Synthesis, 1989, pp. 356-359, and the like. Moreover, the synthetic intermediate E can be synthesized by the methods described in Angew. Chem. Int., Ed. 2008, 47, pp. 8246-8250, J. Org. Chem., 1965, 30, pp. 702-707, and the like. For the reaction conditions of the processes 1 to 3, reference can be made to Japanese Laid-Open Patent Applications 2010-138121 and 2011-14886, WO 2010/113743, and the like. In addition, $R^2$ to $R^{10}$ may be introduced at any of the stages of the synthetic intermediates A to D. After synthesis, it is preferable for purification by column chromatography, recrystallization, or the like to be performed, followed by sublimation purification. Sublimation purification not only allows organic impurities to be separated, but also allows inorganic salts, residual solvents, and the like to be effectively removed.

When a compound expressed by General Formula 1-1 above is used as a light-emitting material, the maximum emission wavelength thereof is preferably less than 455 nm, more preferably at least 400 nm and less than 455 nm, especially preferably at least 420 nm and less than 455 nm, even more preferably at least 430 nm and less than 455 nm, and most preferably at least 440 nm and less than 455 nm.

Organic Electroluminescent Element

The organic electroluminescent element of the present invention has a substrate, a pair of electrodes disposed on this substrate and including an anode and a cathode, and at least one organic layer disposed between these electrodes and including a light-emitting layer, and it is characterized in that a compound expressed by General Formula 1-1 above is contained in at least one layer of the aforementioned light-emitting layer(s).

There are no particular restrictions on the configuration of the organic electroluminescent element of the present invention. FIG. 1 shows one example of the configuration of the organic electroluminescent element of the present invention. The organic electroluminescent element 10 of FIG. 1 has, on a substrate 2, organic layers between a pair of electrodes (an anode 3 and a cathode 9).

The element configuration, substrate, cathode, and anode of the organic electroluminescent element are discussed in detail in Japanese Laid-Open Patent Application 2008-270736, for example, and what is discussed in this publication can be applied to the present invention.

Preferred modes of the organic electroluminescent element of the present invention will be described in detail below in the order of the substrate, electrodes, organic layers, protective layer, sealing container, drive method, emission wavelength, and applications.

<Substrate>

The organic electroluminescent element of the present invention has a substrate.

The substrate used in the present invention is preferably a substrate that will not scatter or attenuate light emitted from the organic layers. In the case of an organic material, one with excellent heat resistance, dimensional stability, solvent resistance, electrical insulation properties, and workability is preferable.

<Electrodes>

The organic electroluminescent element of the present invention has a pair of electrodes disposed on the aforementioned substrate and including an anode and a cathode.

For the quality of the light-emitting element, it is preferable for at least one of the electrodes constituting the pair of electrodes (the anode and/or cathode) to be transparent or semitransparent.

(Anode)

In general, there are no particular restrictions on the shape, structure, size, and so forth of the anode as long as it functions as an electrode that supplies holes to the organic layers, and one can be suitably selected from publicly known electrode materials depending on the purpose and application of the light-emitting element. As was described above, the anode is usually provided as a transparent anode.

(Cathode)

In general, there are no particular restrictions on the shape, structure, size, and so forth of the cathode as long as it functions as an electrode that injects electrons into the organic layers, and one can be suitably selected from publicly known electrode materials depending on the purpose and application of the light-emitting element.

<Organic Layers>

The organic electroluminescent element of the present invention has at least one organic layer that is disposed between the aforementioned electrodes and that includes a light-emitting layer, and is characterized in that a compound expressed by General Formula 1-1 above is contained in at least one layer of the aforementioned light-emitting layer(s).

There are no particular restrictions on the aforementioned organic layer(s), which can be suitably selected according to the purpose and application of the organic electroluminescent element, but [the organic layers] are preferably formed over the aforementioned transparent electrode or the aforementioned semi-transparent electrode. In this case, the organic layers are formed on the entire surface or one face of the aforementioned transparent electrode or the aforementioned semi-transparent electrode.

There are no particular restrictions on the shape, size, thickness, and so forth of the organic layers, which can be suitably selected according to the purpose.

The configuration of the organic layers, a method for forming the organic layers, preferred modes of various layers configuring the organic layers, and the materials used in the various layers in the organic electroluminescent element of the present invention will be described in order below.

(Configuration of Organic Layers)

In the organic electroluminescent element of the present invention, the aforementioned organic layers include a light-emitting layer. The aforementioned organic layers preferably include a charge transport layer. The aforementioned term "charge transport layer" refers to a layer in which charge movement occurs when voltage is applied to the organic electroluminescent element. Concrete examples include a hole injection layer, a hole transport layer, an electron blocking layer, a light-emitting layer, a hole blocking layer, an electron transport layer, or an electron injection layer. If the aforementioned charge transport layer is a hole injection layer, a hole transport layer, an electron blocking layer, or a light-emitting layer, it is possible to manufacture a low-cost and high-efficiency organic electroluminescent element.

The compound expressed by General Formula 1-1 above is contained in at least one layer of the light-emitting layer(s)

in the organic layer(s) disposed between the aforementioned electrodes of the organic electroluminescent element.

However, the compound expressed by General Formula 1-1 above may also be contained in other organic layer(s) of the organic electroluminescent element of the present invention to the extent that does not go against the spirit of the present invention. Examples of organic layers that may contain the compound expressed by General Formula 1-1 above other than the light-emitting layer include a hole injection layer, a hole transport layer, an electron transport layer, an electron injection layer, an exciton blocking layer, and a charge blocking layer (a hole blocking layer, an electron blocking layer, etc.), with an exciton blocking layer, a charge blocking layer, an electron transport layer, or an electron injection layer being preferable, and an exciton blocking layer, a charge blocking layer, or an electron transport layer being more preferable.

When the compound expressed by General Formula 1-1 above is contained in the light-emitting layer, the compound expressed by General Formula 1-1 is preferably contained in an amount of 0.1 to 100 wt %, more preferably 1 to 50 wt %, and even more preferably 2 to 20 wt %, with respect to the total weight of the light-emitting layer.

When the compound expressed by General Formula 1-1 above is contained in an organic layer other than the light-emitting layer, the compound expressed by General Formula 1-1 is preferably contained in an amount of 70 to 100 wt %, more preferably 85 to 100 wt %, and even more preferably 90 to 100 wt % with respect to the total weight of this organic layer.

(Organic Layer Formation Method)

Each of the organic layers of the organic electroluminescent element of the present invention can be favorably formed by vapor deposition, sputtering, or another such dry film formation method, or by transfer, printing, spin coating, bar coating, or another such wet film formation method (solution coating method) as well.

In the organic electroluminescent element of the present invention, the organic layers disposed between the aforementioned pair of electrodes preferably [include] at least one layer that is formed by vapor deposition of a composition containing the compound expressed by General Formula 1-1 above.

(Light-Emitting Layer)

When an electric field is applied, the light-emitting layer accepts holes from the anode, the hole injection layer, or the hole transport layer, accepts electrons from the cathode, the electron injection layer, or the electron transport layer, and has the function of emitting light by providing a site for the rebinding of holes and electrons. However, the aforementioned light-emitting layer in the present invention is not necessarily limited to emission of light by such a mechanism.

The aforementioned light-emitting layer in the organic electroluminescent element of the present invention may be configured solely from the aforementioned light-emitting material or may also be made up of a mixed layer of a host material and the aforementioned light-emitting material. With regard to the types of the aforementioned light-emitting material, there may be just one type or two or more types. The aforementioned host material is preferably a charge transport material. With regard to [the types of] the aforementioned host material, there may be just one type or two or more types, and examples include a mixed configuration of an electron transporting host material and a hole transporting host material. Furthermore, a material which does not have a charge transporting property and does not emit light may also be included in the aforementioned light-emitting layer.

Moreover, the light-emitting layer may be a single layer or a multilayer of two or more layers, and the same light-emitting material or host material may be included in each layer, or different materials may be included in each layer. When there are a plurality of light-emitting layers, each light-emitting layer may also emit light of a different color.

There are no particular restrictions on the thickness of the light-emitting layer, but in general, it is preferably from 2 to 500 nm, and from the standpoint of external quantum efficiency, it is more preferably from 3 to 200 nm and even more preferably from 5 to 100 nm.

A more preferred mode of the organic electroluminescent element of the present invention is that the aforementioned light-emitting layer contains a compound expressed by General Formula 1-1 above, and that the compound expressed by General Formula 1-1 above is used as the light-emitting material of the aforementioned light-emitting layer. Here, in this Specification, the host material refers to a compound that mainly handles the injection and transport of charges in the light-emitting layer, and also a compound that substantially does not emit light itself [The phrase] "substantially does not emit light" here means that the amount of light emitted from this compound that substantially does not emit light is preferably no more than 5% of the total amount of light emitted by the entire element, more preferably no more than 3%, and even more preferably no more than 1%. The compound expressed by General Formula 1-1 above may also be used as the host material of the light-emitting layer.

(Light-Emitting Material)

With the organic electroluminescent element of the present invention, a compound expressed by General Formula 1-1 above is preferably used as the light-emitting material, but even in this case as well, a light-emitting material other than the compound expressed by General Formula 1-1 above can be used in combination. In the organic electroluminescent element of the present invention, furthermore, another light-emitting material different from the compound expressed by General Formula 1-1 above is used in the light-emitting layer even when the compound expressed by General Formula 1-1 above is used as the host material of the light-emitting layer or when it is used for an organic layer other than the light-emitting layer.

The light-emitting material that can be used in the present invention may be a phosphorescent material, a fluorescent material, or the like. Moreover, the light-emitting layer in the present invention can contain two or more types of light-emitting material in order to improve color purity or expand the emission wavelength band.

The fluorescent materials and phosphorescent materials that can be used in the organic electroluminescent element of the present invention are discussed at length, for example, in paragraph numbers [0100] to [0164] of Japanese Laid-Open Patent Application 2008-270736 and paragraph numbers [0088] to [0090] of Japanese Laid-Open Patent Application 2007-266458, and what is discussed in these publications can be applied to the present invention.

Examples of phosphorescent materials that can be used in the present invention include the phosphorescent compounds or the like described in patent documents such as the Specification of U.S. Pat. No. 6,303,238, the Specification of U.S. Pat. No. 6,097,147, WO 00/57676, WO 00/70655, WO 01/08230, WO 01/39234, WO 01/41512, WO 02/02714, WO 02/15645, WO 02/44189, WO 05/19373, Japanese Laid-Open Patent Applications 2001-247859, 2002-302671, 2002-117978, 2003-133074, 2002-235076, 2003-123982, and 2002-170684, European Laid-Open Patent Application 1211257, and Japanese Laid-Open Patent Applications 2002-226495, 2002-234894, 2001-247859, 2001-298470, 2002-173674, 2002-203678, 2002-203679, 2004-357791, 2006-256999, 2007-19462, 2007-84635, and 2007-96259. Of these, examples of more preferable light-emitting materials include iridium complexes, platinum complexes, copper complexes, rhenium complexes, tungsten complexes, rhodium complexes, ruthenium complexes, palladium complexes, osmium complexes, europium complexes, terbium complexes, gadolinium complexes, dysprosium complexes, cerium complexes, and other such phosphorescent metal complex compounds. Especially preferable are iridium complexes, platinum complexes, and rhenium complexes, and of these, iridium complexes, platinum complexes, and rhenium complexes that include at least one coordination from among a metal-carbon bond, a metal-nitrogen bond, a metal-oxygen bond, and a metal-sulfur bond are preferred. In addition, from the standpoints of luminous efficiency, drive durability, chromaticity, and so forth, iridium complexes and platinum complexes are especially favorable, with iridium complexes being most favorable.

There are no particular restrictions on the type of fluorescent material that can be used in the present invention, but besides the compounds expressed by General Formula 1-1 above, examples include benzoxazole, benzimidazole, benzothiazole, styryl benzene, polyphenyl, diphenyl butadiene, tetraphenyl butadiene, naphthalimide, coumarin, pyran, perinone, oxadiazole, aldazine, pyralizine, cyclopentadiene, bis-styryl anthracene, quinacridone, pyrrolopyridine, thiadiazolopyridine, cyclopentadiene, styrylamine, condensed polycyclic aromatic compounds (such as anthracene, phenanthroline, pyrene, perylene, rubrene, and pentacene), a variety of metal complexes typified by metal complexes of 8-quinolinol, pyrromethene complexes, and rare earth complexes, polymer compounds such as polythiophene, polyphenylene, and polyphenylene vinylene, organosilanes, and derivatives of these.

Besides these, it is also possible to use the compounds described in [0082] of Japanese Laid-Open Patent Application 2010-111620 as the light-emitting material.

The light-emitting layer in the organic electroluminescent element of the present invention may be configured from only a light-emitting material or may be made up of a mixed layer of a host material and a light-emitting material. The type of the light-emitting material may be just one type or two or more types. The host material is preferably a charge transport material. There may be just one kind of host material, or two or more kinds may be used, and examples include a mixed configuration of an electron transporting host material and a hole transporting host material. Furthermore, a material which does not have a charge transporting property and does not emit light may be included in the light-emitting layer.

Moreover, the light-emitting layer may be a single layer or a multilayer of two or more layers, and the same light-emitting material or host material may be contained in each layer, or a different material may be contained in each layer. When there are a plurality of light-emitting layers, each of the light-emitting layers may also emit light of a different color.

(Host Material)

The host material is a compound that mainly handles the injection and transport of charges in the light-emitting layer and is also a compound that substantially does not emit light itself. [The phrase] "substantially does not emit light" here means that the amount of light emitted from this compound that substantially does not emit light is preferably no more than 5% of the total amount of light emitted by the entire element, more preferably no more than 3%, and even more preferably no more than 1%.

Besides the compounds expressed by General Formula 1-1 above, the following compounds are examples of host materials that can be used in the organic electroluminescent element of the present invention:

These examples include pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, condensed ring aromatic hydrocarbon compounds (such as fluorene, naphthalene, phenanthrene, and triphenylene), polysilane-based compounds, poly(N-vinylcarbazole), aniline-based copolymers, conductive macromolecular oligomers such as thiophene oligomers and polythiophene, organosilanes, carbon films, pyridine, pyrimidine, triazine, imidazole, pyrazole, triazole, oxazole, oxadiazole [sic][4], fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic acid anhydrides such as naphthalene [and] perylene, phthalocyanine, and a variety of metal complexes typified by metal complexes of an 8-quinolinol derivative, metal phthalocyanine, and metal complexes having benzoxazole or benzothiazole as a ligand, and derivatives of these (which may have a substituent or a condensed ring). Besides these, the compounds described in [0081] and [0083] of Japanese Laid-Open Patent Application 2010-111620 can also be used.

[4]Translator's note: "imidazole," "pyrazole," "triazole," "oxazole," and "oxadiazole" repeatedly appear in this list in the original.

Of these, carbazole, dibenzothiophene, dibenzofuran, arylamine, condensed ring aromatic hydrocarbon compounds, and metal complexes are preferable, with condensed ring aromatic hydrocarbon compounds being especially preferable because they are stable. Condensed ring aromatic hydrocarbon compounds are preferably naphthalene-based compounds, anthracene-based compounds, phenanthrene-based compounds, triphenylene-based compounds, and pyrene-based compounds, more preferably anthracene-based compounds and pyrene-based compounds, and especially preferably anthracene-based compounds. The compounds described in [0033] to [0064] of WO 2010/134350 are especially preferable as the anthracene-based compounds, and examples include compounds H-1 and H-2 (mentioned later).

The host material that can be used in the light-emitting layer of the organic electroluminescent element of the present invention may be either a hole transporting host material or an electron transporting host material.

In the light-emitting layer, from the standpoints of color purity, luminous efficiency, and drive durability, it is preferable for the lowest excited singlet energy ($S_1$ energy) of the aforementioned host material in a film state to be higher than the $S_1$ energy of the aforementioned light-emitting material. The $S_1$ of the host material is preferably higher than the $S_1$ of the light-emitting material by at least 0.1 eV, more preferably higher by at least 0.2 eV, and even more preferably higher by at least 0.3 eV.

If the $S_1$ of the host material in a film state is lower than the $S_1$ of the light-emitting material, emission of light is quenched, so the host material needs to have a higher $S_1$ than the light-emitting material. Moreover, even when the $S_1$ of the host material is higher than that of the light-emitting material, if the difference in the $S_1$ [values] between the two is small, reverse energy movement from the light-emitting material to the host material will occur in places, and this can lead to lower efficiency, a decrease in color purity, or a decrease in durability. Accordingly, the host material needs to have a sufficiently high $S_1$ as well as good chemical stability and carrier injection and transport properties.

In addition, there are no particular restrictions on the amount in which the host compound is contained in the light-emitting layer of the organic electroluminescent element of the present invention, but from the standpoints of luminous efficiency and drive voltage, it is preferably from 15 to 95 wt % with respect to the weight of all the compounds forming the light-emitting layer. If the light-emitting layer includes a plurality of types of host compound including a compound expressed by General Formula 1-1, then the compound expressed by General Formula 1-1 is preferably contained in the total host compound in an amount of at least 50 wt % and no more than 99 wt %.

(Other Layers)

The organic electroluminescent element of the present invention may have other layers besides the aforementioned light-emitting layer.

Examples of other organic layers other than the aforementioned light-emitting layer that may be included in the aforementioned organic layers include a hole injection layer, a hole transport layer, a blocking layer (hole blocking layer, exciton blocking layer, etc.), and an electron transport layer. The following are concrete examples of the layer configuration, but the present invention is in no way limited to these configurations:

- anode/hole transport layer/light-emitting layer/electron transport layer/cathode
- anode/hole transport layer/light-emitting layer/blocking layer/electron transport layer/cathode
- anode/hole transport layer/light-emitting layer/blocking layer/electron transport layer/electron injection layer/cathode
- anode/hole injection layer/hole transport layer/light-emitting layer/blocking layer/electron transport layer/cathode
- anode/hole injection layer/hole transport layer/light-emitting layer/electron transport layer/electron injection layer/cathode
- anode/hole injection layer/hole transport layer/light-emitting layer/blocking layer/electron transport layer/electron injection layer/cathode
- anode/hole injection layer/hole transport layer/blocking layer/light-emitting layer/blocking layer/electron transport layer/electron injection layer/cathode The organic electroluminescent element of the present invention preferably includes at least one organic layer preferably disposed between the aforementioned anode and the aforementioned light-emitting layer (A). From the anode side, a hole injection layer, a hole transport layer, and an electron blocking layer can be cited as examples of organic layers preferably disposed between the aforementioned anode and the aforementioned light-emitting layer of (A) above.

The organic electroluminescent element of the present invention preferably includes at least one organic layer preferably disposed between the aforementioned cathode and the aforementioned light-emitting layer (B). From the cathode side, an electron injection layer, an electron transport layer, and a hole blocking layer can be cited as examples of organic layers preferably disposed between the aforementioned cathode and the aforementioned light-emitting layer of (B) above.

In concrete terms, one example of a preferred mode of the organic electroluminescent element of the present invention is the mode described in FIG. 1, being a mode in which a hole injection layer 4, a hole transport layer 5, a light-emitting layer 6, a hole blocking layer 7, and an electron transport layer 8 are laminated in this order from the side of the anode 3 as the aforementioned organic layers.

These layers other than the aforementioned light-emitting layer that may be included in the organic electroluminescent element of the present invention will be described below.

(A) Organic Layers Preferably Disposed Between the Anode and the Aforementioned Light-Emitting Layer First, (A) organic layers preferably disposed between the aforementioned anode and the aforementioned light-emitting layer will be described.

(A-1) Hole Injection Layer and Hole Transport Layer

The hole injection layer and the hole transport layer are layers having the function of accepting holes from the anode or the anode side and transporting them to the cathode side.

The light-emitting element of the present invention preferably includes at least one organic layer between the light-emitting layer and the anode, and this organic layer preferably contains at least one type of compound from among the compounds expressed by General Formula Sa-1, General Formula Sb-1, and General Formula Sc-1 below:

[Twenty-Second Chemical Formula]

General Formula Sa-1

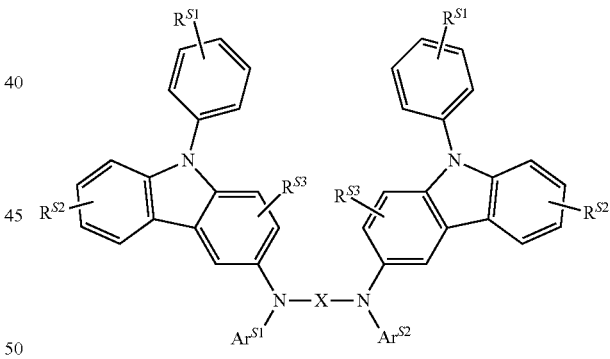

(In the formula, X represents a substituted or unsubstituted $C_1$ to $C_{30}$ alkylene group, a substituted or unsubstituted $C_2$ to $C_{30}$ alkenylene group, a substituted or unsubstituted $C_6$ to $C_{30}$ arylene group, a substituted or unsubstituted $C_2$ to $C_{30}$ heteroarylene group, or a substituted or unsubstituted $C_2$ to $C_{30}$ heterocycle. $R^{S1}$, $R^{S2}$, and $R^{S3}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S1}$, $R^{S2}$, and $R^{S3}$ [groups] may bond to each other to form a saturated or unsaturated carbon ring. $Ar^{S1}$ and $Ar^{S2}$ represent each independently a substituted or unsubstituted $C_6$ to $C_{30}$ aryl group or a substituted or unsubstituted $C_2$ to $C_{30}$ heteroaryl group.)

[Twenty-Third Chemical Formula]

General Formula Sb-1

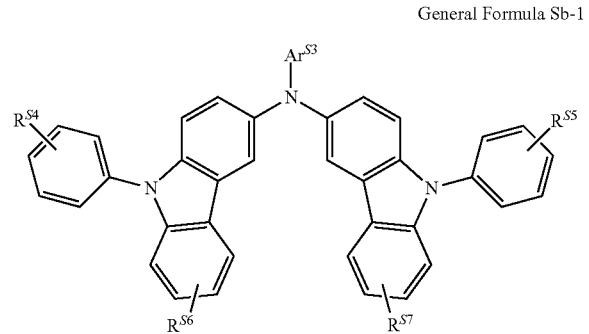

(In the formula, $R^{S4}$, $R^{S5}$, $R^{S6}$, and $R^{S7}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S4}$, $R^{S5}$, $R^{S6}$, and $R^{S7}$ [groups] may bond to each other to form a saturated or unsaturated carbon ring. $Ar^{S3}$ represents a substituted or unsubstituted $C_6$ to $C_{30}$ aryl group or a substituted or unsubstituted $C_2$ to $C_{30}$ heteroaryl group.)

[Twenty-Fourth Chemical Formula]

General Formula Sc-1

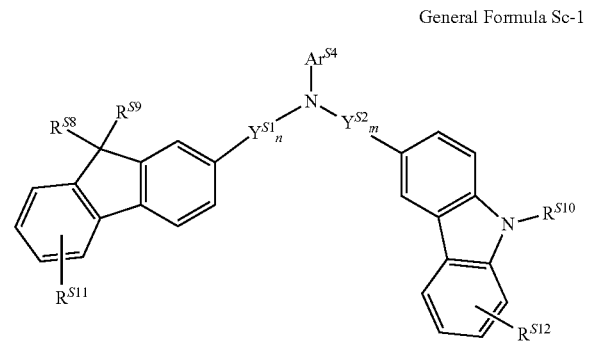

(In the formula, $R^{S8}$ and $R^{S9}$ represent each independently a hydrogen atom, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S10}$ represents a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S11}$ and $R^{S12}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S11}$ and $R^{S12}$ [groups] may bond to each other to form a saturated or unsaturated carbon ring. $Ar^{S4}$ represents a substituted or unsubstituted $C_6$ to $C_{30}$ aryl group or a substituted or unsubstituted $C_2$ to $C_{30}$ heteroaryl group. $Y^{S1}$ and $Y^{S2}$ represent each independently a substituted or unsubstituted $C_1$ to $C_{30}$ alkylene group or a substituted or unsubstituted $C_6$ to $C_{30}$ arylene group. n and m represent each independently an integer from 0 to 5.)

General Formula Sa-1 above will now be described.

In General Formula Sa-1 above, X represents a substituted or unsubstituted $C_1$ to $C_{30}$ alkylene group, a substituted or unsubstituted $C_2$ to $C_{30}$ alkenylene group, a substituted or unsubstituted $C_6$ to $C_{30}$ arylene group, a substituted or unsubstituted $C_2$ to $C_{30}$ heteroarylene group, or a substituted or unsubstituted $C_2$ to $C_{30}$ heterocycle. X is preferably a substituted or unsubstituted $C_6$ to $C_{30}$ arylene group, more preferably a substituted or unsubstituted phenylene, a substituted or unsubstituted biphenylene, and a substituted or unsubstituted naphthylene, and even more preferably a substituted or unsubstituted biphenylene.

$R^{S1}$, $R^{S2}$, and $R^{S3}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S1}$, $R^{S2}$, and $R^{S3}$ [groups] may bond to each other to form a saturated or unsaturated carbon ring. Examples of the aforementioned saturated or unsaturated carbon ring include naphthalene, azulene, anthracene, fluorene, and phenalene. $R^{S1}$, $R^{S2}$, and $R^{S3}$ are preferably a hydrogen atom, a substituted or unsubstituted $C_1$ to $C_{30}$ alkyl group, a substituted or unsubstituted $C_6$ to $C_{30}$ aryl group, a substituted or unsubstituted $C_5$ to $C_{30}$ condensed polycyclic group, and a cyano group, with a hydrogen atom being more preferable.

$Ar^{S1}$ and $Ar^{S2}$ represent each independently a substituted or unsubstituted $C_6$ to $C_{30}$ aryl group or a substituted or unsubstituted $C_2$ to $C_{30}$ heteroaryl group. $Ar^{S1}$ and $Ar^{S2}$ are preferably a substituted or unsubstituted phenyl group.

Next, General Formula Sb-1 above will be described.

In General Formula Sb-1 above, $R^{S4}$, $R^{S5}$, $R^{S6}$, and $R^{S7}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S4}$, $R^{S5}$, $R^{S6}$, and $R^{S7}$ [groups] may bond to each other to form a saturated or unsaturated carbon ring. Examples of the saturated or unsaturated carbon ring include naphthalene, azulene, anthracene, fluorene, and phenalene. $R^{S4}$, $R^{S5}$, $R^{S6}$, and $R^{S7}$ preferably a hydrogen atom, a substituted or unsubstituted $C_1$ to $C_{30}$ alkyl group, a substituted or unsubstituted $C_6$ to $C_{30}$ aryl group, a substituted or unsubstituted $C_5$ to $C_{30}$ condensed polycyclic group, and a cyano group, with a hydrogen atom being more preferable.

$Ar^{S3}$ represents a substituted or unsubstituted $C_6$ to $C_{30}$ aryl group or a substituted or unsubstituted $C_2$ to $C_{30}$ heteroaryl group. $Ar^{S3}$ is preferably a substituted or unsubstituted phenyl group.

Next, General Formula Sc-1 above will be described.

In General Formula Sc-1 above, $R^{S8}$ and $R^{S9}$ represent each independently a hydrogen atom, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S8}$ and $R^{S9}$ are preferably a substituted or unsubstituted $C_1$ to $C_{30}$ alkyl group and a substituted or unsubstituted $C_6$ to $C_{30}$ aryl group, with a methyl group and a phenyl group being more preferable. $R^{S10}$ represents a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S10}$ is preferably a substituted or unsubstituted $C_6$ to $C_{30}$ aryl group and more preferably a phenyl group. $R^{S11}$ and $R^{S12}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S11}$ and $R^{S12}$ [groups] may bond to each other to form a saturated or unsaturated carbon ring. Examples of the aforementioned saturated or unsaturated carbon ring include naphthalene, azulene, anthracene, fluorene, and phenalene. $R^{S11}$ and $R^{S12}$ are preferably a hydrogen atom, a substituted or unsubstituted $C_1$ to $C_{30}$ alkyl group, a substituted or unsubstituted $C_6$ to $C_{30}$ aryl group, a substituted or unsubstituted $C_5$ to $C_{30}$ condensed polycyclic group, and a cyano group, with a hydrogen atom being more preferable. $Ar^{S4}$ represents a substituted or unsubstituted $C_6$ to $C_{30}$ aryl group or a substituted or unsubstituted $C_2$ to $C_{30}$ heteroaryl group. $Y^{S1}$ and $Y^{S2}$ represent a substituted or unsubstituted $C_1$ to $C_{30}$ alkylene or a substituted or unsubstituted $C_6$ to $C_{30}$ arylene. $Y^{S1}$ and $Y^{S2}$ are preferably a substituted or unsubstituted $C_6$ to $C_{30}$ arylene, with a substituted or unsubstituted phenylene being more preferable. n is an integer from 0 to 5, preferably from 0 to 3, more preferably from 0 to 2, and even more preferably 0. m is an integer from 0 to 5, preferably from 0 to 3, more preferably from 0 to 2, and even more preferably 1.

General Formula Sa-1 above is preferably a compound expressed by General Formula Sa-2 below:

[Twenty-Fifth Chemical Formula]

General Formula Sa-2

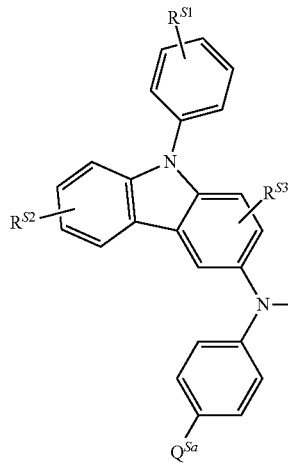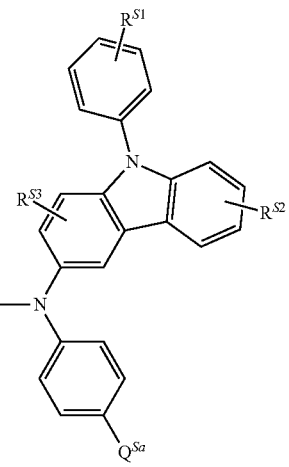

(In the formula, $R^{S1}$, $R^{S2}$, and $R^{S3}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S1}$, $R^{S2}$, and $R^{S3}$ [groups] may bond to each other to form a saturated or unsaturated carbon ring. $Q^{Sa}$ [groups] represent each independently a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group.)

General Formula Sa-2 above will now be described. $R^{S1}$, $R^{S2}$, and $R^{S3}$ are defined the same as those in General Formula Sa-1, and the preferred ranges are also the same. $Q^{Sa}$ [groups] represent each independently a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group. $Q^{Sa}$ is preferably a hydrogen atom, a cyano group, a fluorine atom, a substituted or unsubstituted $C_1$ to $C_{30}$ alkyl group, and a substituted or unsubstituted $C_6$ to $C_{30}$ aryl group, more preferably a hydrogen atom and a substituted or unsubstituted $C_1$ to $C_{30}$ alkyl group, and even more preferably a hydrogen atom.

General Formula Sb-1 above is preferably a compound expressed by General Formula Sb-2 below:

[Twenty-Sixth Chemical Formula]

General Formula Sb-2

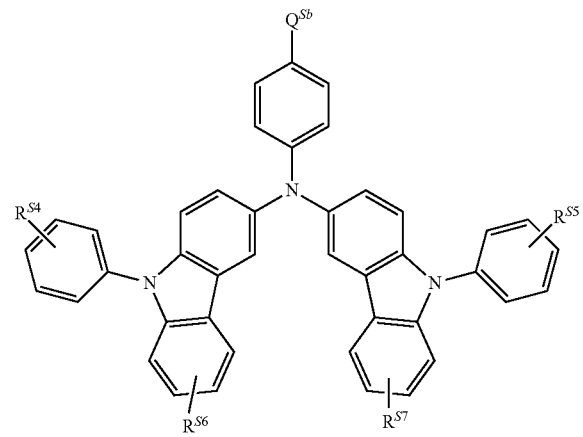

(In the formula, $R^{S4}$, $R^{S5}$, $R^{S6}$, and $R^{S7}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S4}$, $R^{S5}$, $R^{S6}$, and $R^{S7}$ [groups] may bond to each other to faun a saturated or unsaturated carbon ring. $Q^{Sb}$ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group.)

General Formula Sb-2 above will now be described. $R^{S4}$, $R^{S5}$, $R^{S6}$, and $R^{S7}$ are defined the same as those in General Formula Sb-1, and the preferred ranges are also the same. $Q^{Sa}$ [sic][5] represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group. $Q^{Sa}$ [sic] is preferably a hydrogen atom, a cyano group, a fluorine atom, a substituted or unsubstituted $C_1$ to $C_{30}$ alkyl group, and a substituted or unsubstituted $C_6$ to $C_{30}$ aryl group, more preferably a hydrogen atom and a substituted or unsubstituted $C_1$ to $C_{30}$ alkyl group, and even more preferably a hydrogen atom.

[5]Translator's note: apparent error in the original; "$Q^{Sa}$" should be "$Q^{Sb}$" (same below).

General Formula Sc-1 above is preferably a compound expressed by General Formula Sc-2 below:

[Twenty-Seventh Chemical Formula]

General Formula Sc-2

(In the formula, $R^{S8}$ and $R^{S9}$ represent each independently a hydrogen atom, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S10}$ represents a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S11}$ and $R^{S12}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S11}$ and $R^{S12}$ [groups] may bond to each other to form a saturated or unsaturated carbon ring. $Q^{Sc}$ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group.)

General Formula Sc-2 above will now be described. $R^{S8}$, $R^{S9}$, $R^{S10}$, $R^{S11}$, and $R^{S12}$ are defined the same as those in General Formula Sc-1, and the preferred ranges are also the same. $Q^{Sc}$ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group. $Q^{Sc}$ is preferably a hydrogen atom, a cyano group, a fluorine atom, a substituted or unsubstituted $C_1$ to $C_{30}$ alkyl group, or a substituted or unsubstituted $C_6$ to $C_{30}$ aryl group, more preferably a hydrogen atom or a substituted or unsubstituted $C_6$ to $C_{30}$ aryl group, and even more preferably a phenyl group.

Concrete examples of compounds expressed by General Formulas Sa-1, Sb-1, and Sc-1 above are as follows, but the present invention is not limited to or by the following concrete examples:

[Twenty-Eighth Chemical Formula]
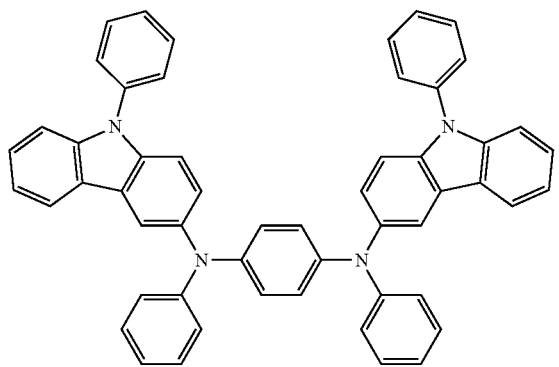
1
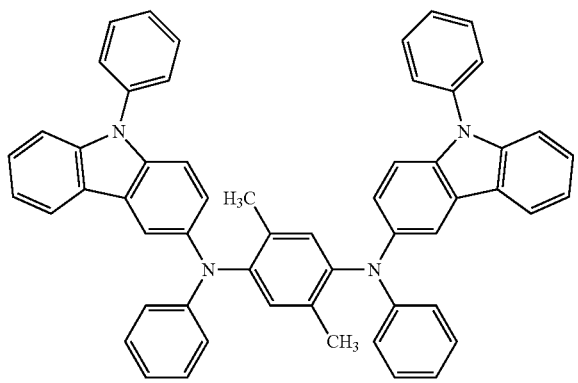
2
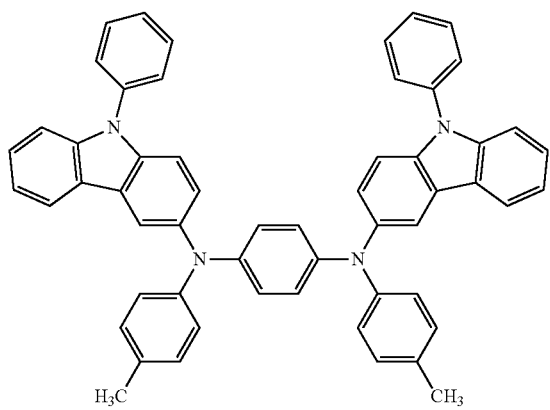
3
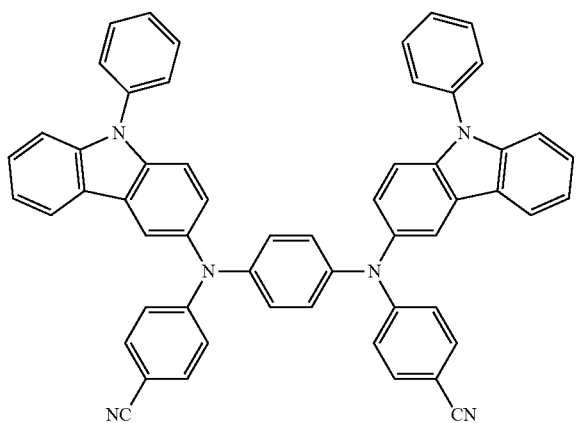
4
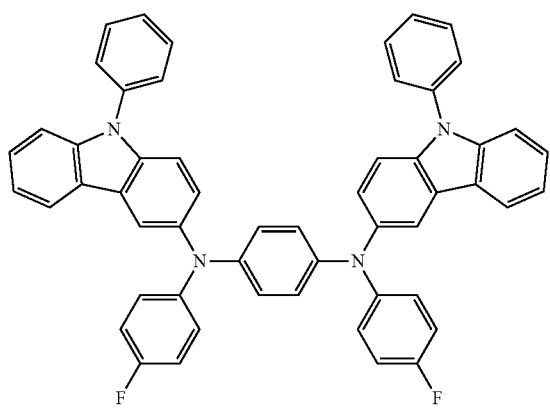
5
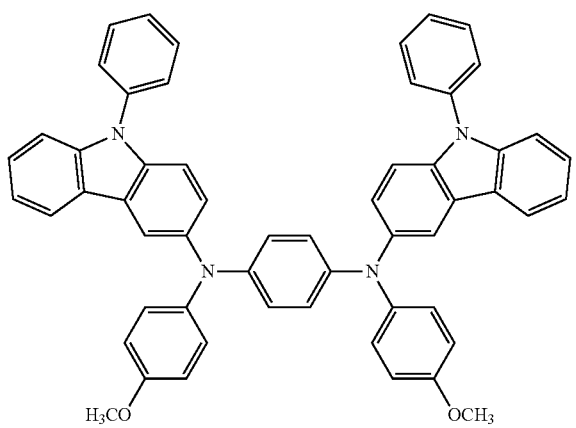
6

-continued
7
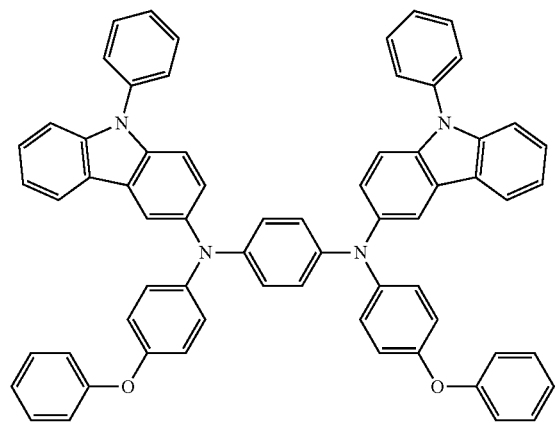
8
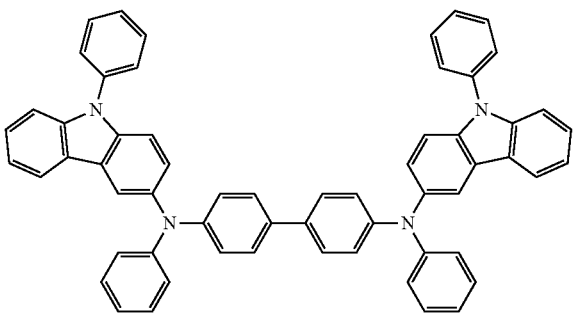
[Twenty-Ninth Chemical Formula]
9
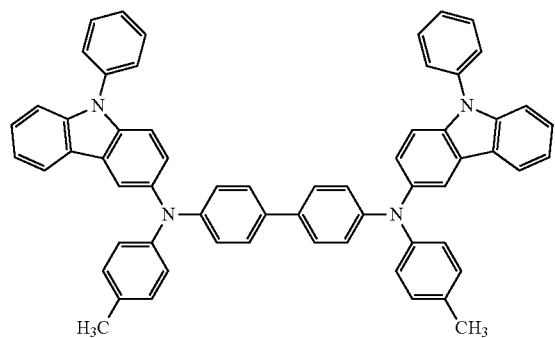
10
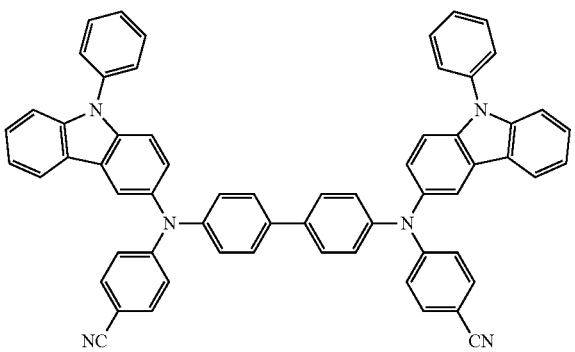
11
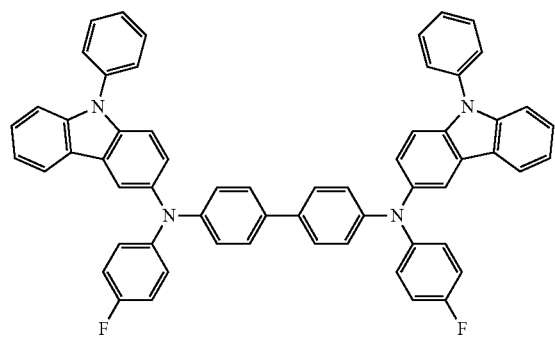
12
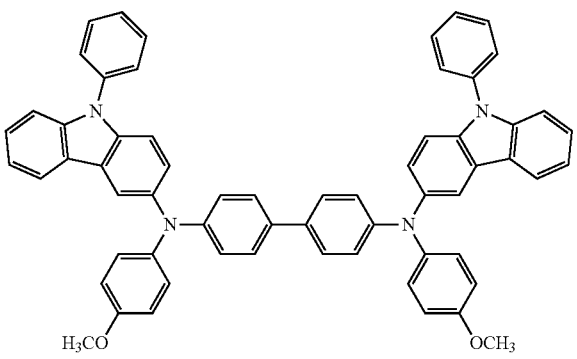
13
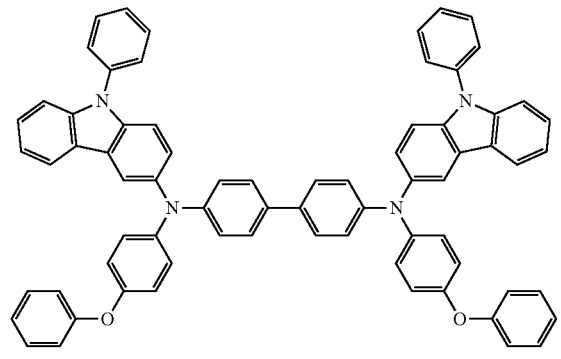
14
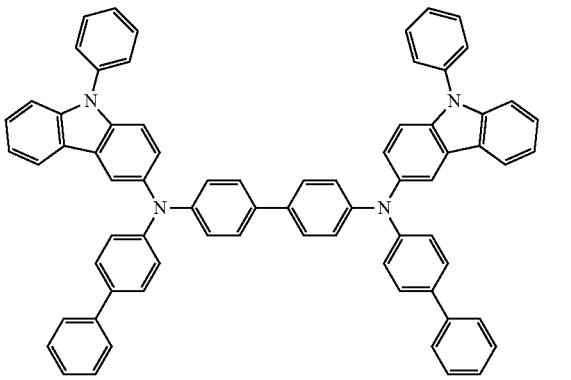

[Thirtieth Chemical Formula]
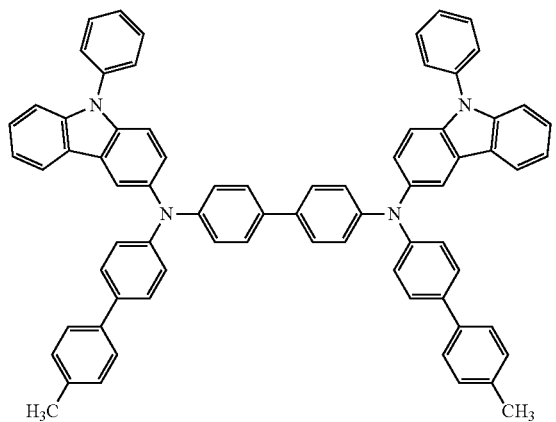
15
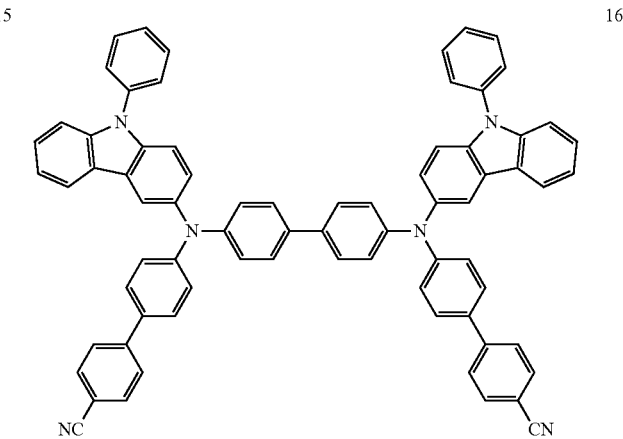
16
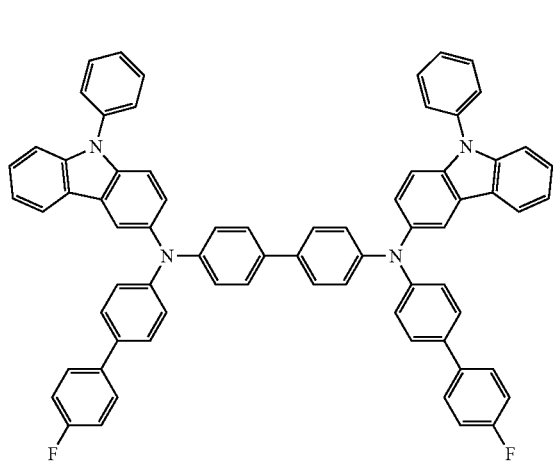
17
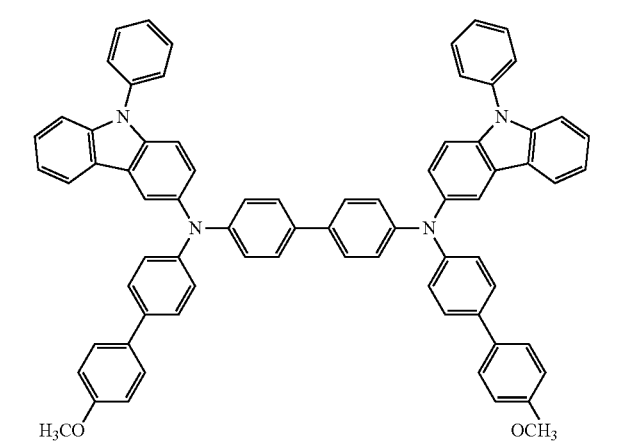
18
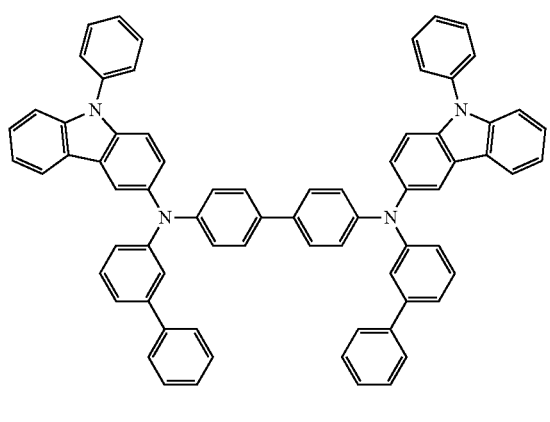
19
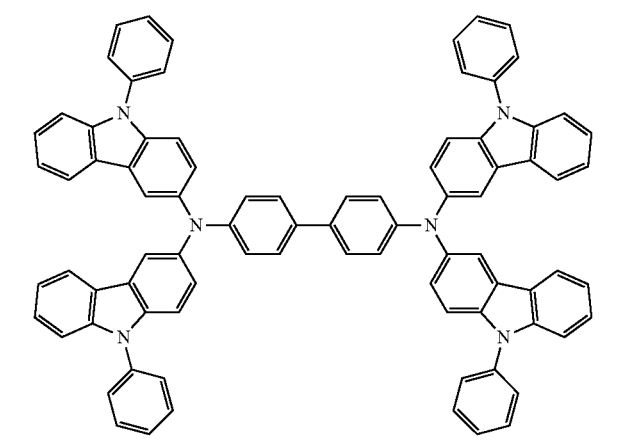
20

[Thirty-First Chemical Formula]
21
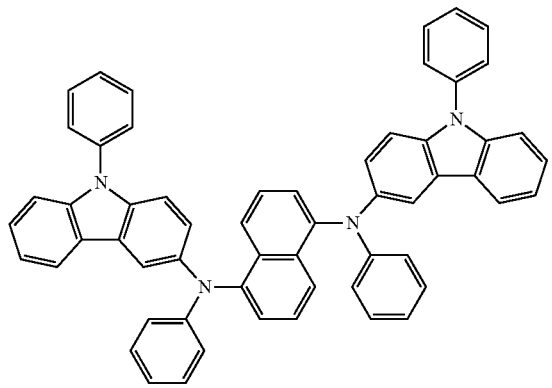
22
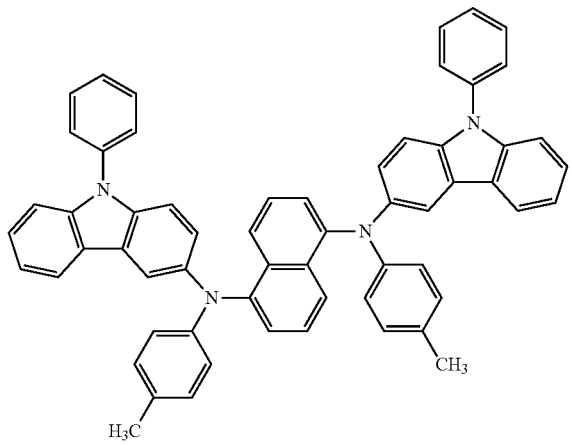
23
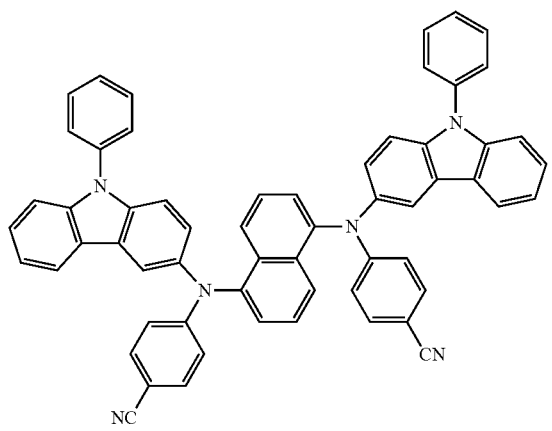
24
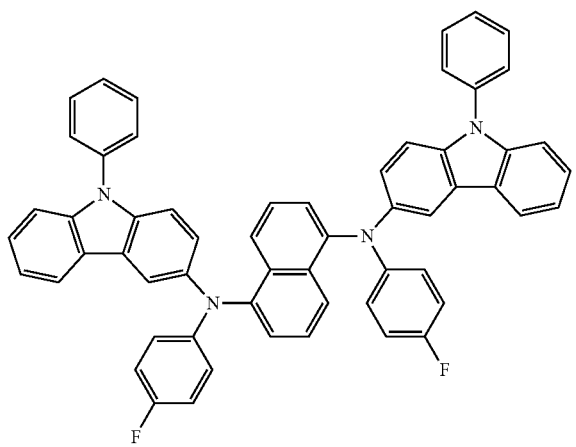
25
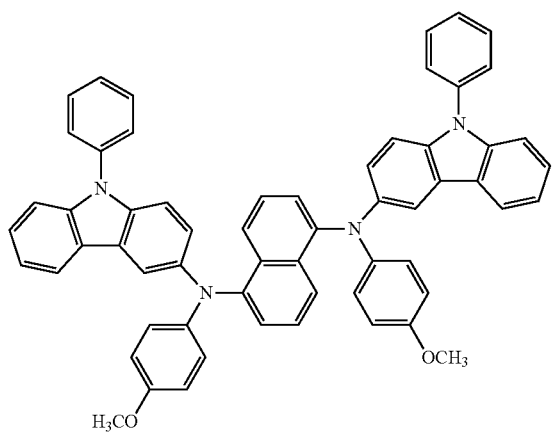
26
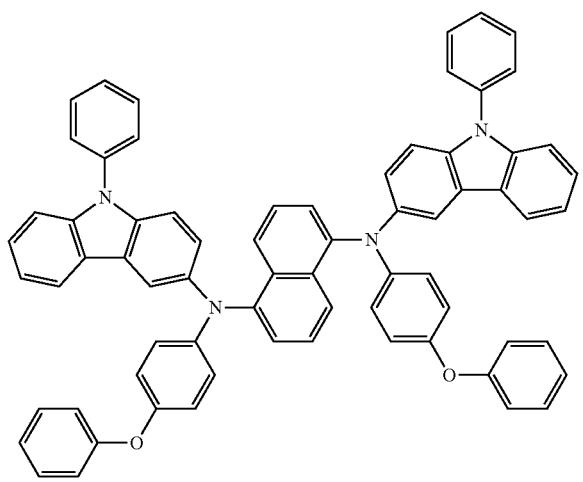

[Thirty-Second Chemical Formula]
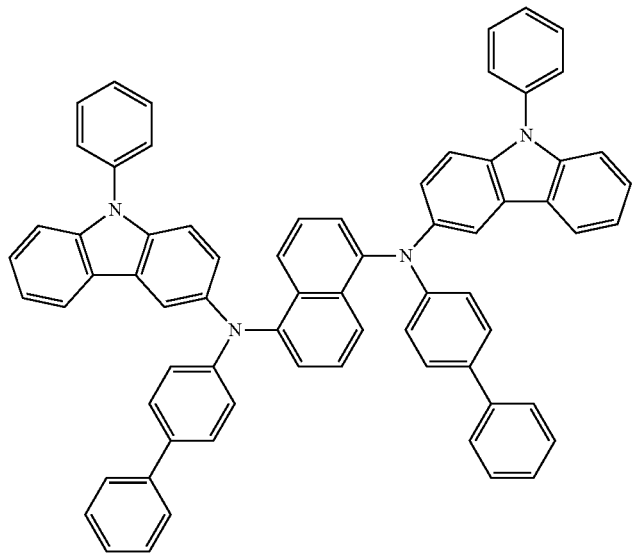
27
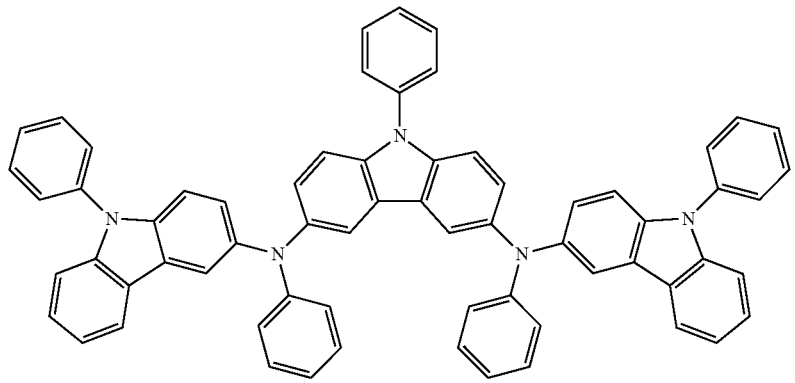
28
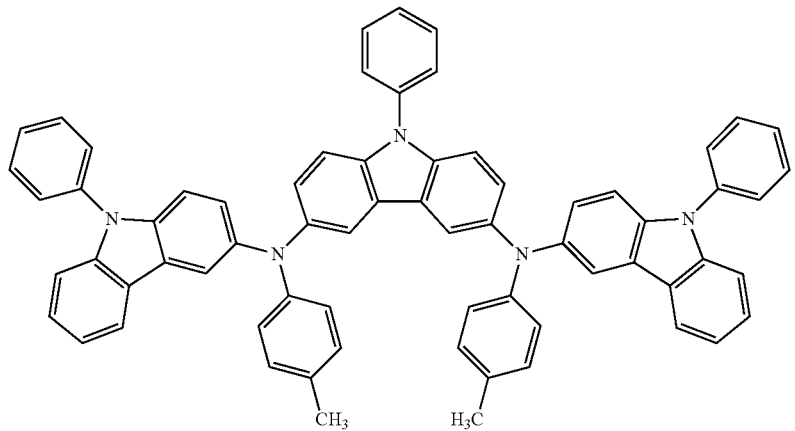
29

30
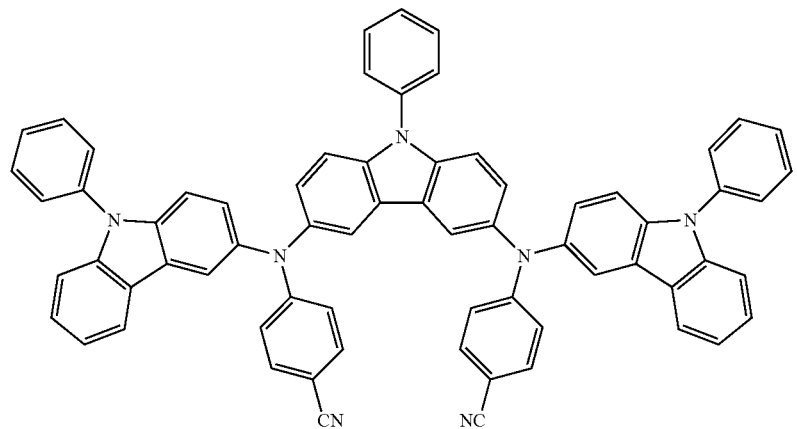
31
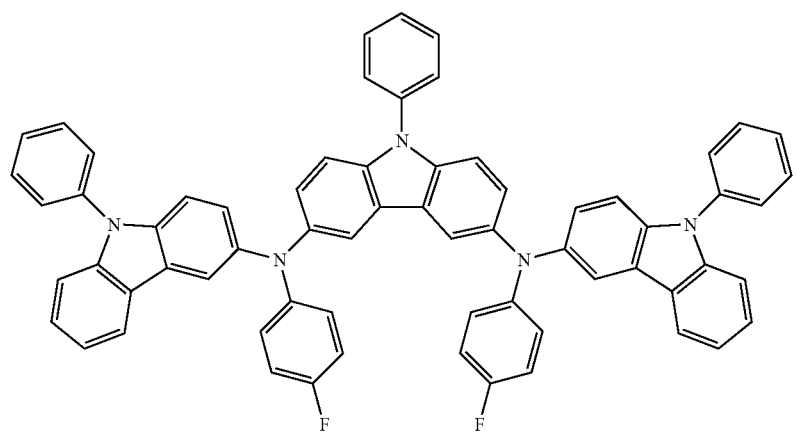
32
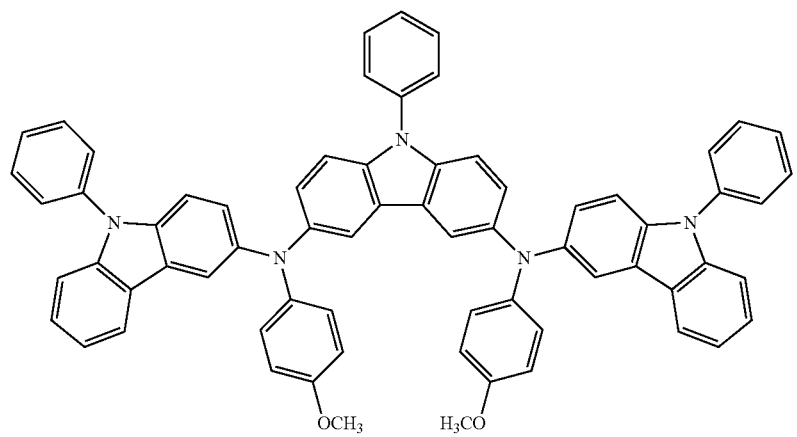

[Thirty-Third Chemical Formula]
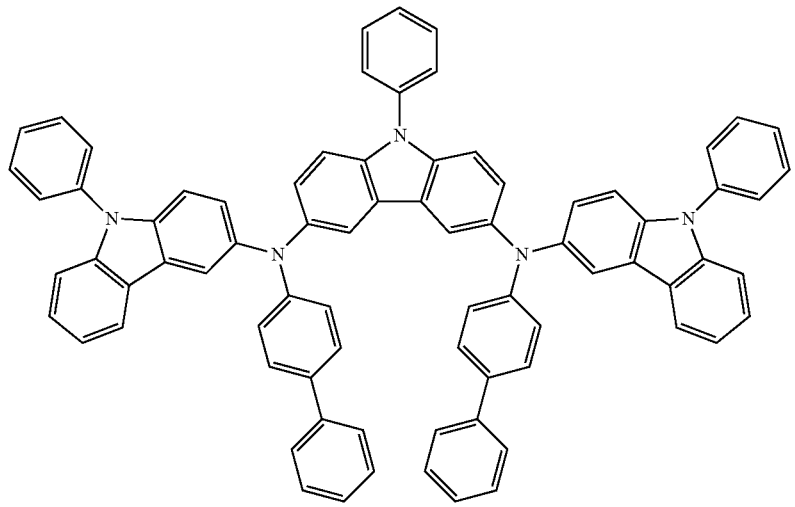
33
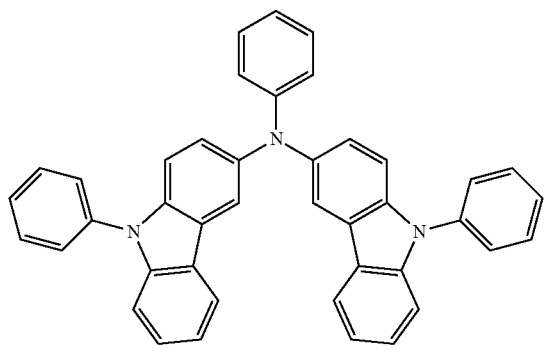
34
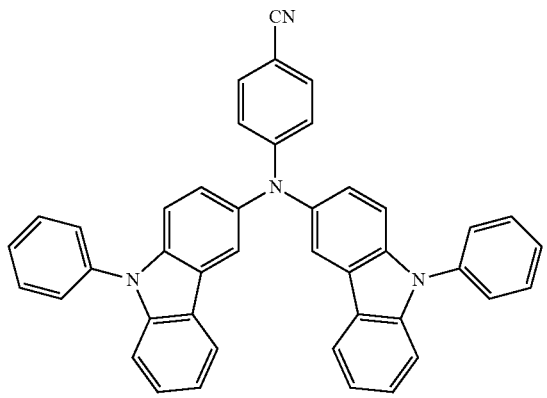
35
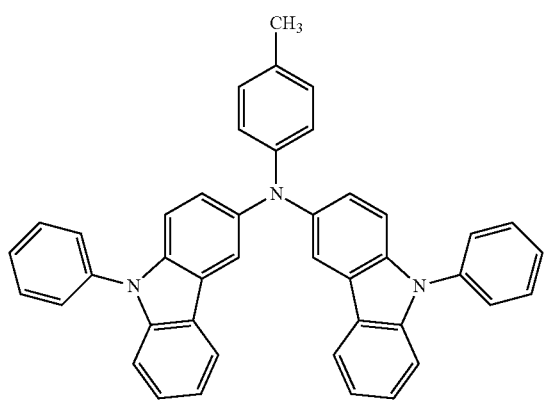
36
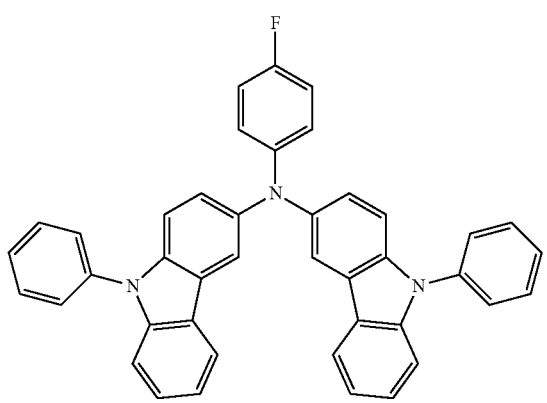
37

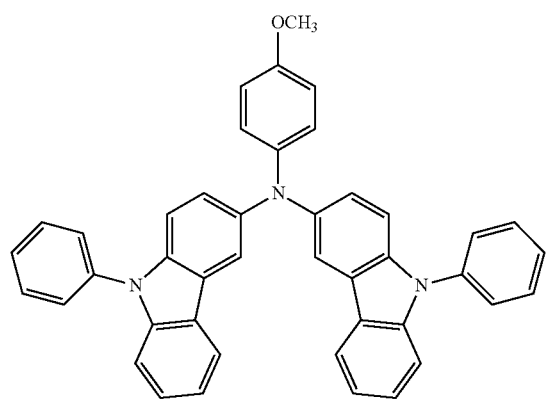
[Thirty-Fourth Chemical Formula]
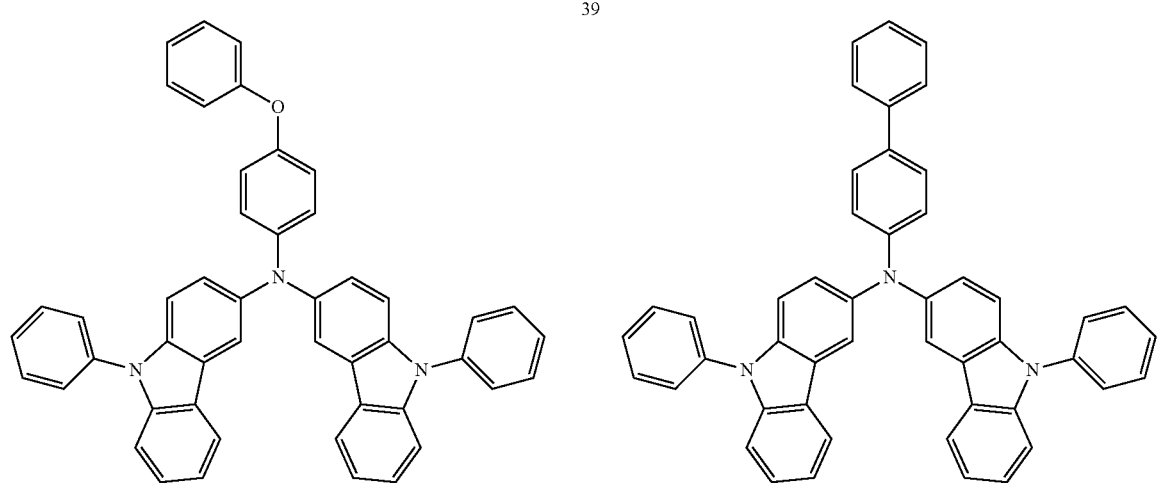
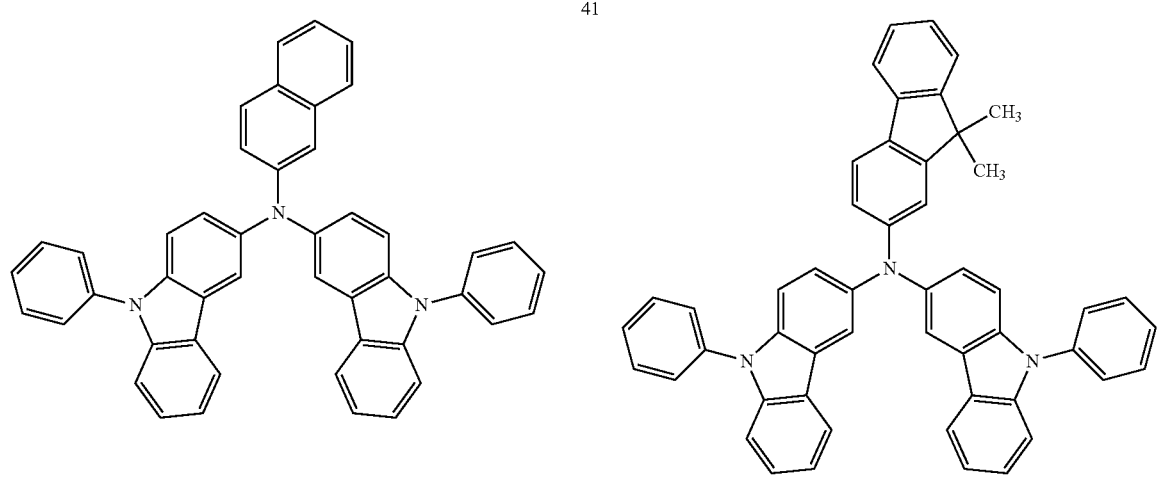

[Thirty-Fifth Chemical Formula]
43
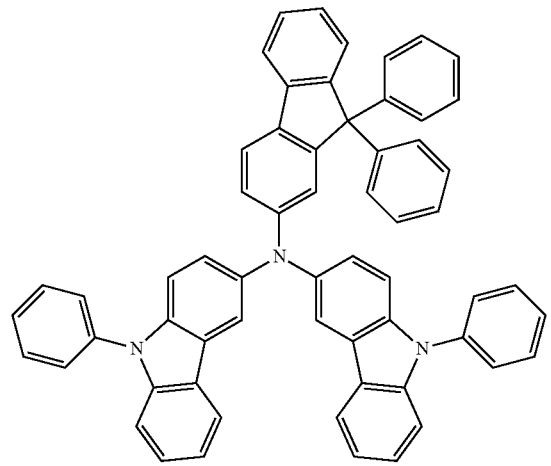
44
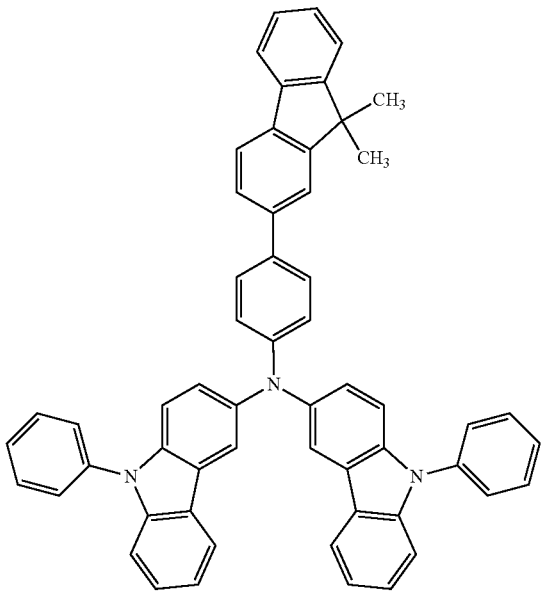
45
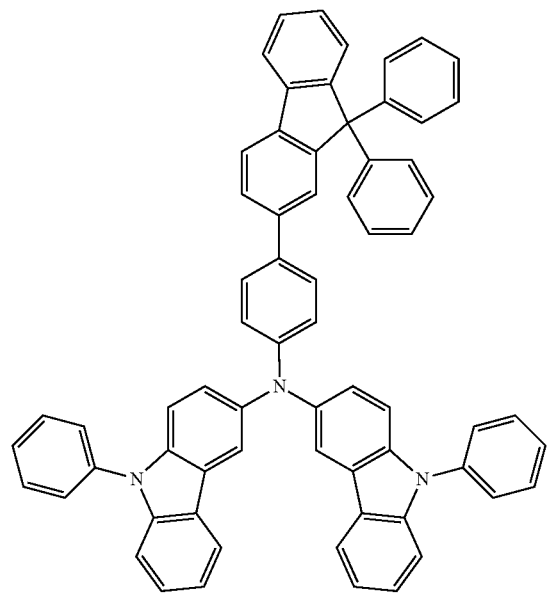
46
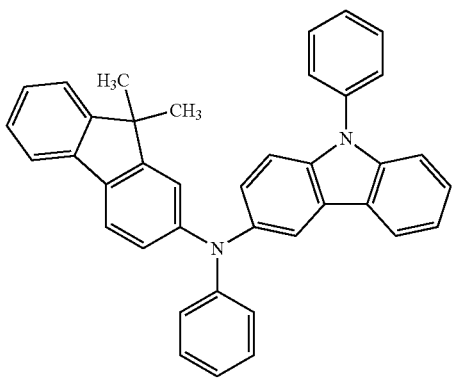

[Thirty-Sixth Chemical Formula]
47
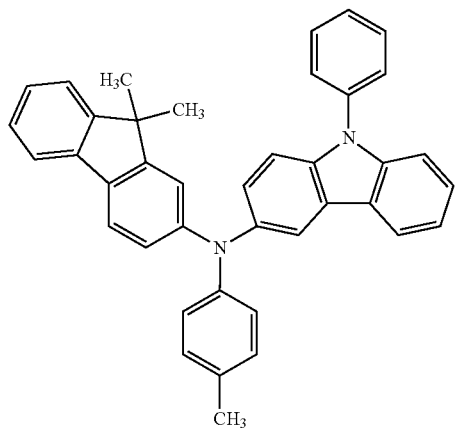
48
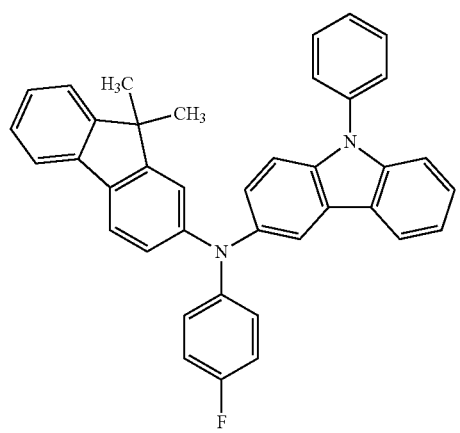
49
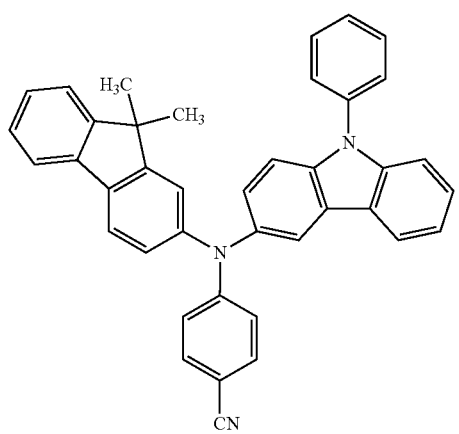
50
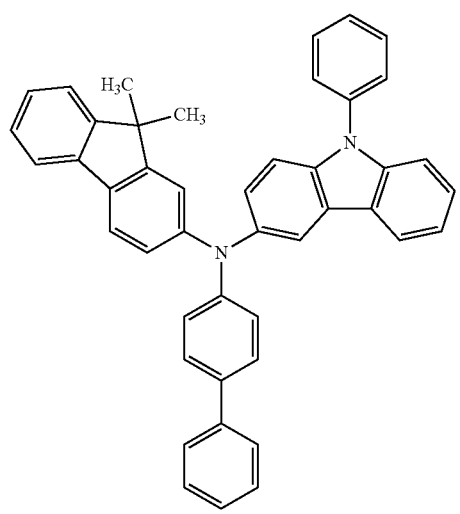
51
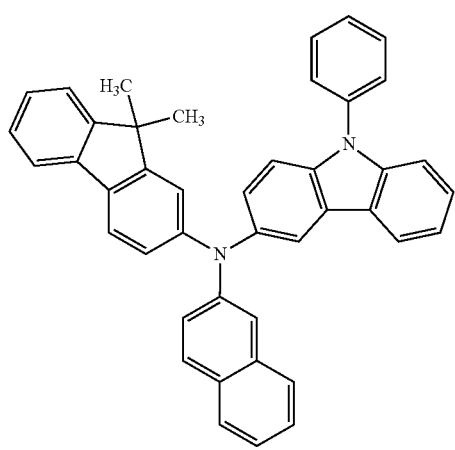
52
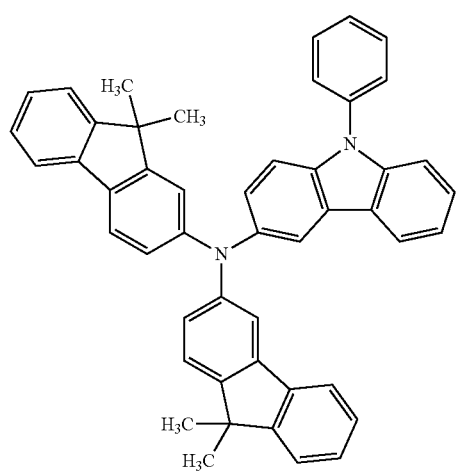

53
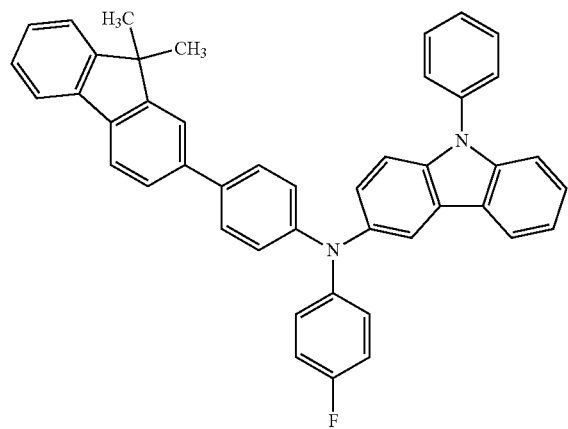
54
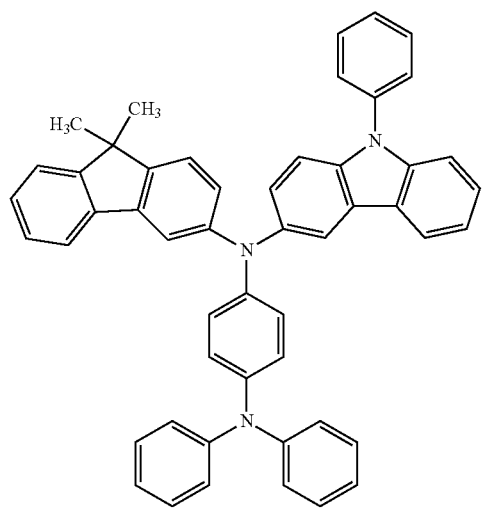
55
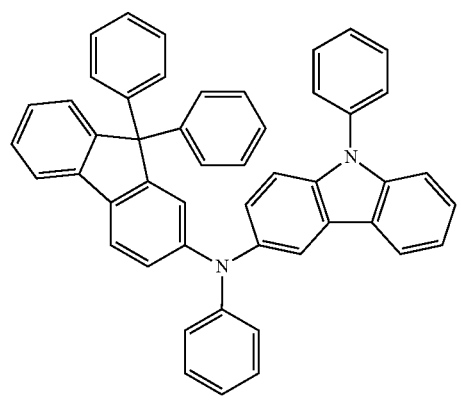
[Thirty-Seventh Chemical Formula]
56
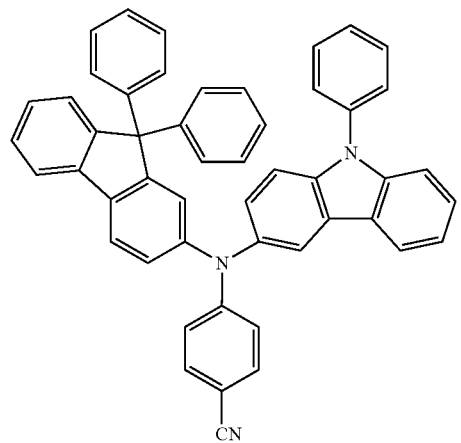
57
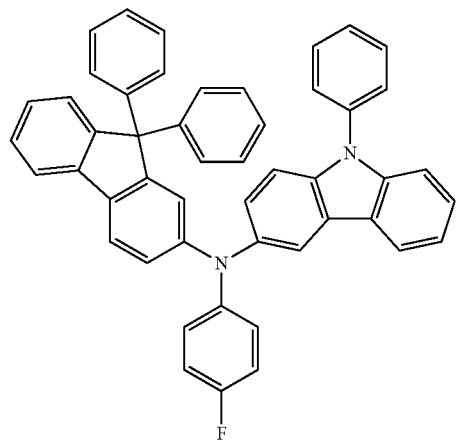

-continued
58
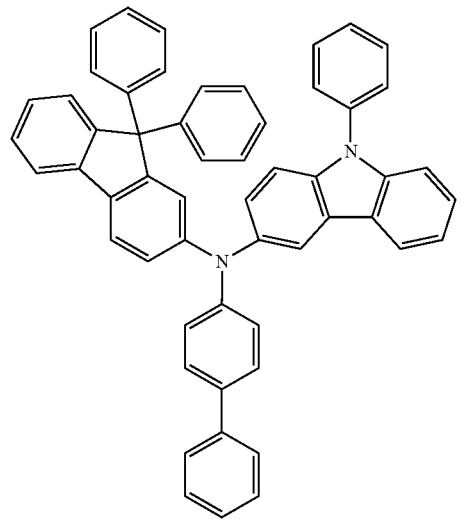
59
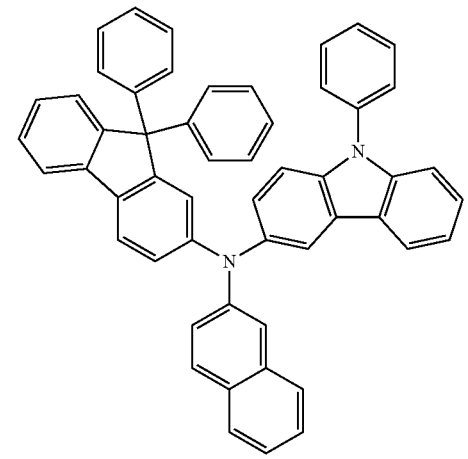
60
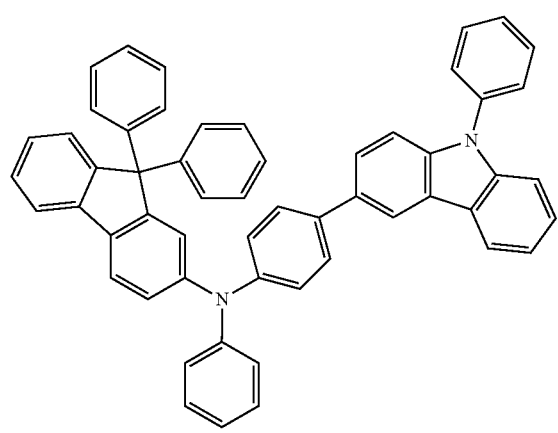
61
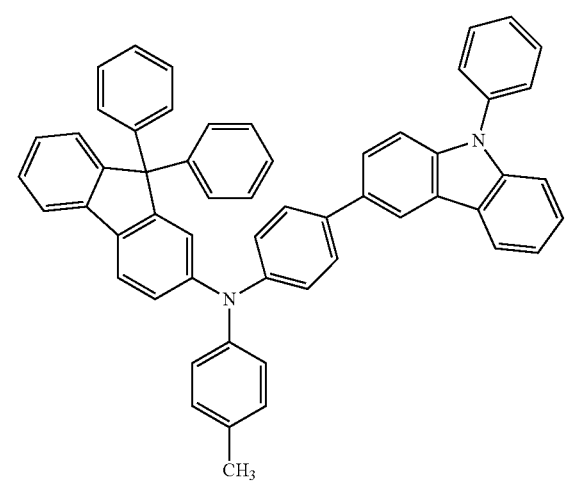
62
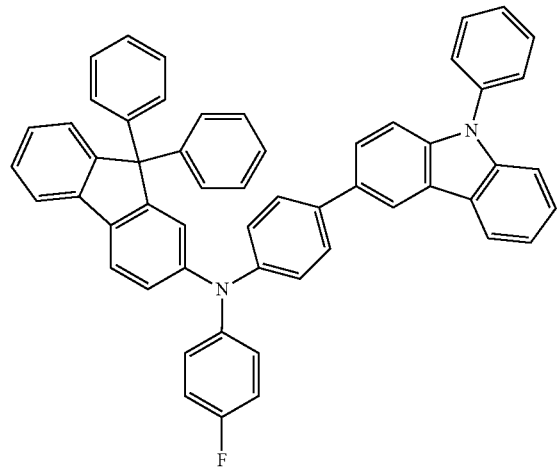
63
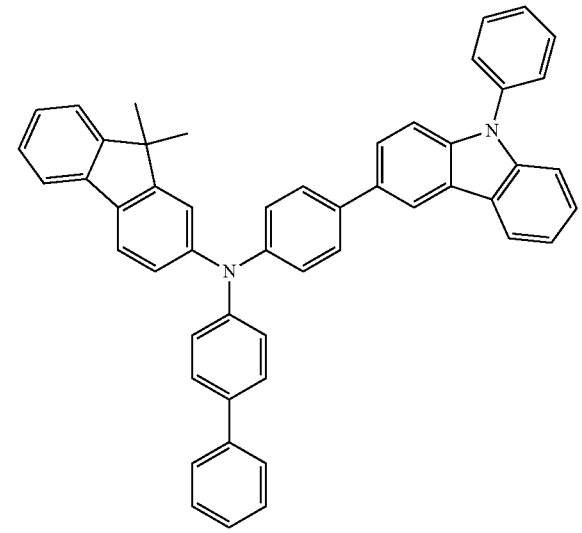
The compounds expressed by General Formula Sa-1, Sb-1, or Sc-1 above can be synthesized by the methods described in Japanese Laid-Open Patent Application 2007-318101. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the light-emitting element of the present invention, the compound expressed by General Formula Sa-1, Sb-1, or Sc-1 above is preferably contained in an organic layer between the aforementioned light-emitting layer and the aforementioned anode, and is more preferably contained in the layer adjacent to the light-emitting layer on the anode side among the [organic layers]. It is especially preferable if it is the hole transport material contained in the hole transport layer.

The compound expressed by General Formula Sa-1, Sb-1, or Sc-1 above is preferably contained in an amount of 70 to 100 wt % and more preferably 85 to 100 wt % with respect to the total weight of the organic layer to which [this compound is] added.

Besides these, regarding the hole injection layer and hole transport layer, what is stated in paragraph numbers [0165] to [0167] of Japanese Laid-Open Patent Application 2008-270736 can also be applied to the present invention.

The aforementioned hole injection layer preferably contains an electron-accepting dopant. The effects of having the hole injection layer contain an electron-accepting dopant are that hole injection is enhanced, drive voltage decreases, efficiency is higher, and so forth. The electron-accepting dopant may be either an organic material or inorganic material as long as it is a material capable of pulling electrons from the doped material and generating radical cations, but examples include TCNQ compounds such as tetracyanoquinodimethane (TCNQ) and tetrafluorotetracyanoquinodimethane ($F_4$-TCNQ), hexaazatriphenylene compounds such as hexacyanohexaazatriphenylene (HAT-CN), and molybdenum oxide.

The electron-accepting dopant in the aforementioned hole injection layer is preferably contained in an amount of 0.01 to 50 wt %, more preferably 0.1 to 40 wt %, and even more preferably 0.2 to 30 wt %, with respect to the weight of all the compounds forming the hole injection layer.

(A-2) Electron Blocking Layer

The electron blocking layer is a layer having the function of preventing the electrons transported from the cathode side to the light-emitting layer from escaping to the anode side. In the present invention, an electron blocking layer can be provided as an organic layer that is adjacent to the light-emitting layer on the anode side.

As examples of organic compounds that constitute an electron blocking layer, those listed above as examples of hole transport materials can be used.

The thickness of the electron blocking layer is preferably 1 to 500 nm, more preferably 3 to 100 nm, and even more preferably 5 to 50 nm.

The electron blocking layer may have a single-layer structure composed of one or more types of the aforementioned materials, or may have a multilayer structure composed of a plurality of layers of the same composition or different compositions.

From the standpoints of color purity, luminous efficiency, and drive durability, the material used in the electron blocking layer preferably has [an $S_1$ energy] higher than the $S_1$ energy of the aforementioned light-emitting material. The $S_1$ in a film state of the material used in the electron blocking layer is preferably at least 0.1 eV higher than the $S_1$ of the light-emitting material, more preferably at least 0.2 eV higher, and even more preferably at least 0.3 eV higher.

(B) Organic Layers Preferably Disposed Between the Cathode and the Aforementioned Light-Emitting Layer Next, (B) organic layers preferably disposed between the aforementioned cathode and the aforementioned light-emitting layer will be described.

(B-1) Electron Injection Layer and Electron Transport Layer

The electron injection layer and the electron transport layer are layers having the function of accepting electrons from the cathode or the cathode side and transporting them to the anode side. The electron injection material and electron transport material used for these layers may be compounds with either a low or a high molecular weight.

The compounds expressed by General Formula 1-1 above, for example, can be used as electron transport materials. Other electron transport materials are preferably selected from among a pyridine derivative, a quinoline derivative, a pyrimidine derivative, a pyrazine derivative, a phthalazine derivative, a phenanthroline derivative, a triazine derivative, a triazole derivative, an oxazole derivative, an oxadiazole derivative, an imidazole derivative, a benzimidazole derivative, an imidazopyridine derivative, a fluorenone derivative, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, an aromatic tetracarboxylic acid anhydride such as naphthalene and perylene, a phthalocyanine derivative, various metal complexes typified by metal complexes of an 8-quinolinol derivative, metal phthalocyanine, and metal complexes having benzoxazole or benzothiazole as a ligand, an organic silane derivative typified by silole, and condensed ring hydrocarbon compounds (such as naphthalene, anthracene, phenanthrene, triphenylene, and pyrene), and the like, with a pyridine derivative, a benzimidazole derivative, an imidazopyridine derivative, a metal complex, or a condensed ring hydrocarbon compound being more preferable.

From the standpoint of lowering the drive voltage, the thickness of the electron injection layer and electron transport layer is preferably no more than 500 nm for each.

The thickness of the electron transport layer is preferably 1 to 500 nm, more preferably 5 to 200 nm, and even more preferably 10 to 100 nm. In addition, the thickness of the electron injection layer is preferably 0.1 to 200 nm, more preferably 0.2 to 100 nm, and even more preferably 0.5 to 50 nm.

The electron injection layer and the electron transport layer may have a single-layer structure composed of one or more types of the aforementioned materials, or a multilayer structure composed of a plurality of layers of the same composition or different compositions.

The electron injection layer preferably contains an electron-donating dopant. The effects of having the electron injection layer contain an electron-donating dopant are that electron injection is enhanced, drive voltage decreases, efficiency is higher, and so forth. The electron-donating dopant may be either an organic material or inorganic material as long as it is a material capable of giving electrons to the doped material and generating radical anions, but examples include tetrathianafulvalene (TTF), tetrathianaphthacene (TTT) [sic][6], bis-[1,3-diethyl-2-methyl-1,2-dihydrobenzimidazolyl] and other such dihydroimidazole compounds, lithium, and cesium.

[6]Translator's note: The abbreviation of "tetrathianaphthacene" should be "TTN," and "TTT" is "tetrathiatetracene," so this abbreviation "TTT" here seems to be an error in the original for "TTN."

The electron-donating dopant in the electron injection layer is preferably contained in an amount of 0.01 to 50 wt %, more preferably 0.1 to 40 wt %, and even more preferably 0.5 to 30 wt %, with respect to the weight of all the compounds forming the electron injection layer.

(B-2) Hole Blocking Layer

The hole blocking layer is a layer having the function of preventing the holes transported from the anode side to the light-emitting layer from escaping to the cathode side. In the present invention, a hole blocking layer can be provided as an organic layer that is adjacent to the light-emitting layer on the cathode side.

The $S_1$ energy in a film state of the organic compound constituting the hole blocking layer is preferably higher than the $S_1$ energy of the light-emitting material for the purpose of preventing energy movement of excitons generated in the light-emitting layer, thus preventing a decrease in luminous efficiency.

The compounds expressed by General Formula 1-1 above can be used as examples of organic compounds that constitute a hole blocking layer.

Examples of other organic compounds that constitute a hole blocking layer other than the compounds expressed by General Formula 1-1 above include aluminum(III) bis(2-methyl-8-quinolinato) 4-phenylphenolate (abbreviated as Balq) and other such aluminum complexes, triazole derivatives, and phenanthroline derivatives such as 2,9-dimethyl-4,7-diphenyl-1,10-phenanthroline (abbreviated as BCP).

The thickness of the hole blocking layer is preferably 1 to 500 nm, more preferably 3 to 100 nm, and even more preferably 5 to 50 nm.

The hole blocking layer may have a single-layer structure composed of one or more types of the aforementioned materials, or may have a multilayer structure composed of a plurality of layers of the same composition or different compositions.

From the standpoints of color purity, luminous efficiency, and drive durability, the material used in the hole blocking layer preferably has [an $S_1$ energy] higher than the $S_1$ energy of the aforementioned light-emitting material. The $S_1$ in a film state of the material used in the hole blocking layer is preferably at least 0.1 eV higher than the $S_1$ of the light-emitting material, more preferably at least 0.2 eV higher, and even more preferably at least 0.3 eV higher.

(B-3) Materials Especially Preferably Used in the Organic Layers Preferably Disposed Between the Cathode and the Aforementioned Light-Emitting Layer In the organic electroluminescent element of the present invention, examples of materials especially preferably used as the materials of (B) the organic layers preferably disposed between the aforementioned cathode and the aforementioned light-emitting layer include a compound expressed by General Formula 1-1 above, a compound expressed by General Formula P-1 below, and a compound expressed by General Formula O-1 below.

Compounds expressed by the aforementioned General Formula O-1 and compounds expressed by the aforementioned General Formula P-1 will be described below.

The organic electroluminescent element of the present invention preferably includes at least one organic layer between the light-emitting layer and the cathode, and from the standpoints of the drive voltage and efficiency of the element, this organic layer preferably contains at least one type of compound expressed by General Formula O-1 below. General Formula O-1 will be described below:

[Thirty-Eight Chemical Formula]

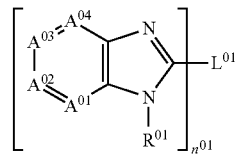

General Formula O-1

(In General Formula O-1, $R^{O1}$ represents an alkyl group, an aryl group, or a heteroaryl group. $A^{O1}$ to $A^{O4}$ represent each independently C—$R^A$ or a nitrogen atom. $R^A$ represents a hydrogen atom, an alkyl group, an aryl group, or a heteroaryl group, and the plurality of $R^A$ [groups] may be the same or different. $L^{O1}$ represents a divalent to hexavalent linking group composed of an aryl ring or a heteroaryl ring. $n^{O1}$ represents an integer from 2 to 6.)

$R^{O1}$ represents an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. $R^{O1}$ is preferably an aryl group or a heteroaryl group and more preferably an aryl group. Substituents that are preferable when the aryl group of $R^1$ has a substituent include an alkyl group, an aryl group, and a cyano group, with an alkyl group or aryl group being more preferable, and an aryl group being even more preferable. If the aryl group of $R^{O1}$ has a plurality of substituents, the plurality of substituents may bond to each other to form a five- or six-membered ring. The aryl group of $R^{O1}$ is preferably a phenyl group that may have a substituent selected from Substituent Group A, more preferably a phenyl group that may be substituted with an alkyl group or an aryl group, and even more preferably an unsubstituted phenyl group or a 2-phenylphenyl group.

$A^{O1}$ to $A^{O4}$ represent each independently C—$R^A$ or a nitrogen atom. It is preferable for zero to two of $A^{O1}$ to $A^{O4}$ to be a nitrogen atom, and it is more preferable for zero or one to be a nitrogen atom. Preferably all of $A^{O1}$ to $A^{O4}$ are C—$R^A$, or $A^{O1}$ is a nitrogen atom and $A^{O2}$ to $A^{O4}$ are C—$R^A$, more preferably $A^{O1}$ is a nitrogen atom and $A^{O2}$ to $A^{O4}$ are C—$R^A$, and even more preferably $A^{O1}$ is a nitrogen atom, $A^{O2}$ to $A^{O4}$ are C—$R^A$, and all of the $R^A$ [groups] are hydrogen atoms.

$R^A$ represents a hydrogen atom, an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. Furthermore, the plurality of $R^A$ [groups] may be the same or different. $R^A$ is preferably a hydrogen atom or an alkyl group and more preferably a hydrogen atom.

$L^{O1}$ represents a divalent to hexavalent linking group composed of an aryl ring (preferably $C_6$ to $C_{30}$) or a heteroaryl ring (preferably $C_4$ to $C_{12}$). $L^{O1}$ is preferably an arylene group, a heteroarylene group, an aryltolyl group, or a heteroaryltolyl group, more preferably a phenylene group, a biphenylene group, or a benzenetriyl group, and even more preferably a biphenylene group or a benzenetriyl group. $L^{O1}$ may have a substituent selected from the aforementioned Substituent Group A, and if there is a substituent, the substituent is preferably an alkyl group, an aryl group, or a cyano group. Concrete examples of $L^{O1}$ are listed below:

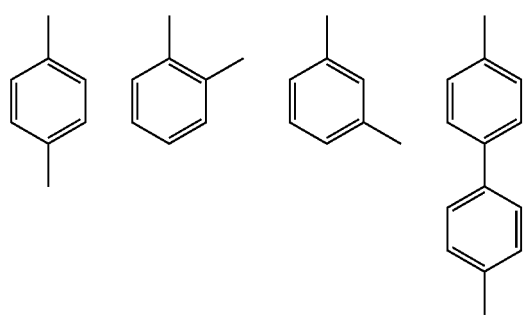
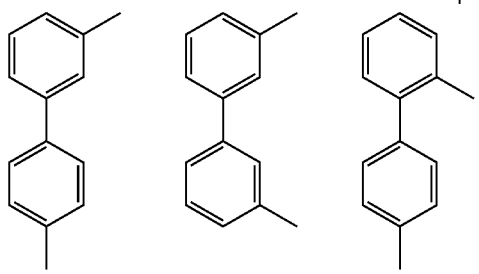
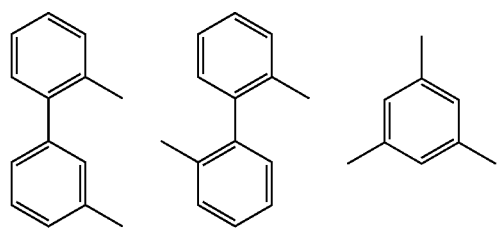
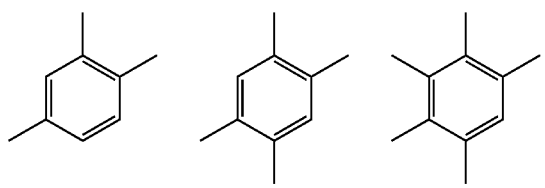
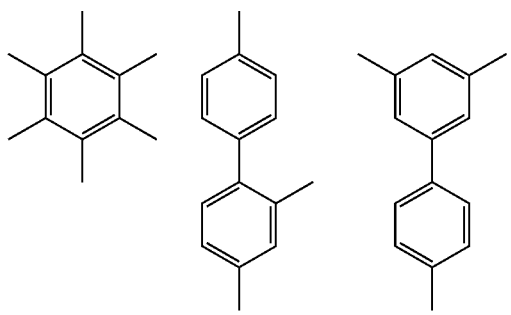
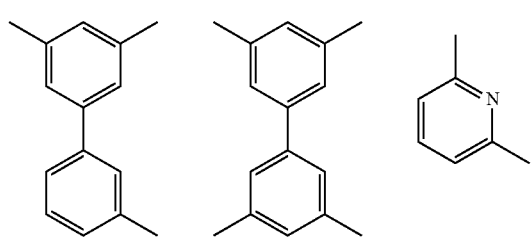

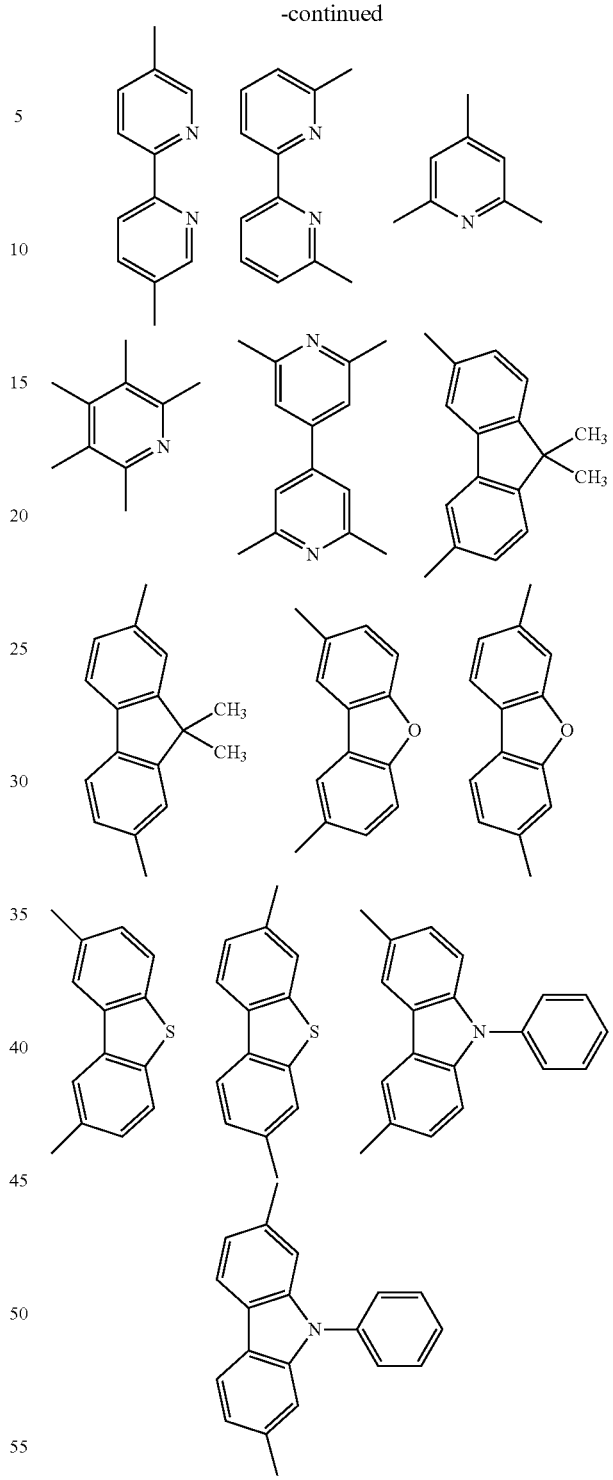

$n^{O1}$ represents an integer from 2 to 6, preferably an integer from 2 to 4, and more preferably 2 or 3. From the standpoint of efficiency of the element, $n^{O1}$ is most preferably 3, and from the standpoint of durability of the element, 2 is most preferable.

From the standpoints of stability during high-temperature storage and stable operation with respect to heat emission during high-temperature drive and during drive [sic], the glass transition temperature (Tg) of the compound expressed by General Formula O-1 above is preferably from 100° C.

to 300° C., more preferably from 120° C. to 300° C., even more preferably from 120° C. to 300° C., and even still more preferably from 140° C. to 300° C.

Concrete examples of the compound expressed by General Formula O-1 will be given below, but it should not be construed that the compounds expressed by General Formula O-1 that can be used in the present invention are limited to or by these concrete examples:

[Fortieth Chemical Formula]

OM-1

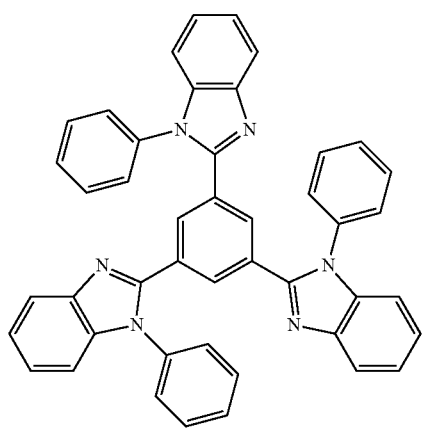

OM-2

OM-3

OM-4

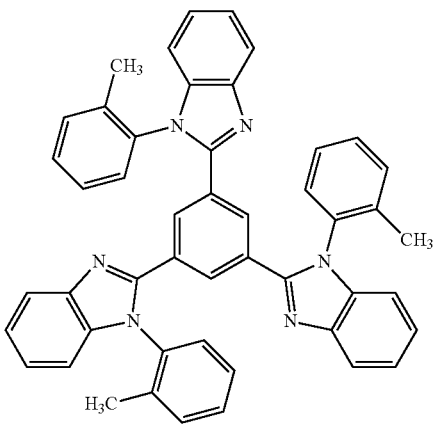

OM-5

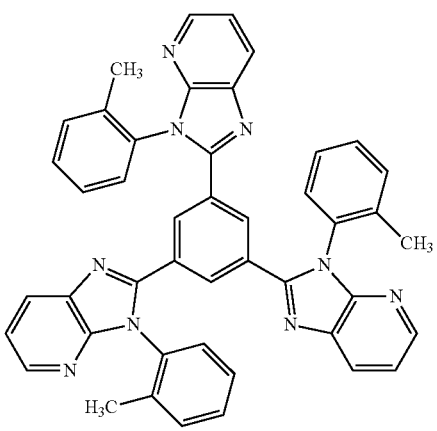

OM-6

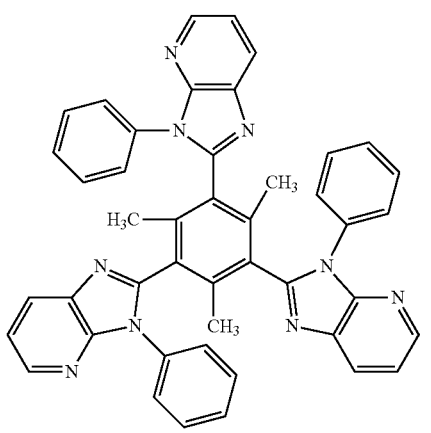

OM-7
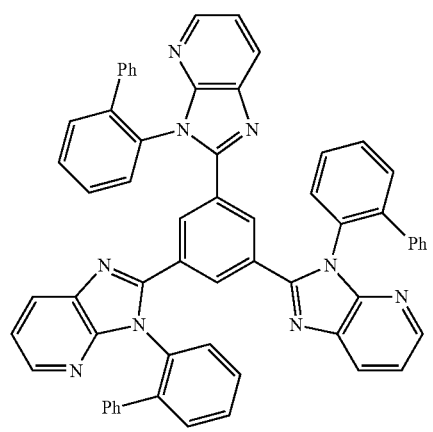
[Forty-First Chemical Formula]
OM-10
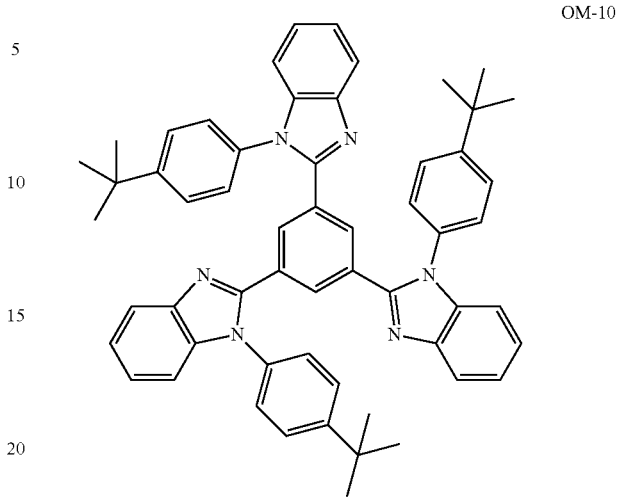
OM-8
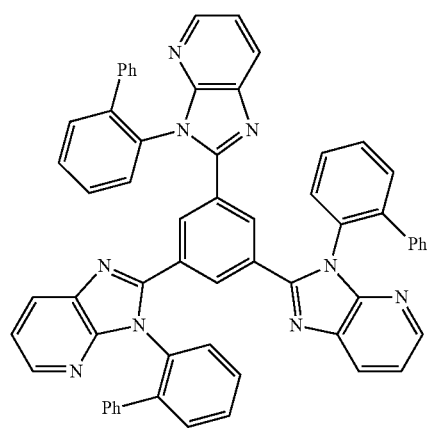
OM-11
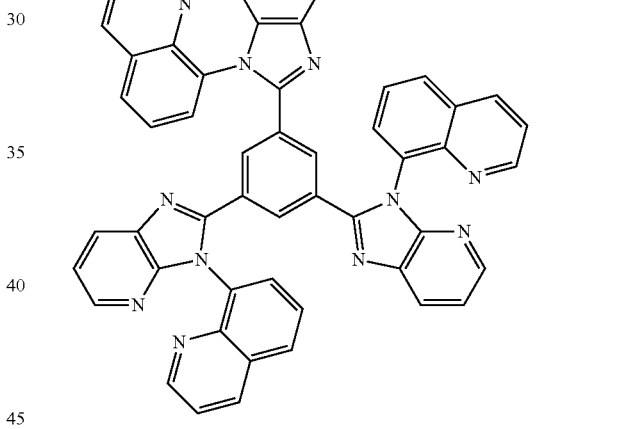
OM-9
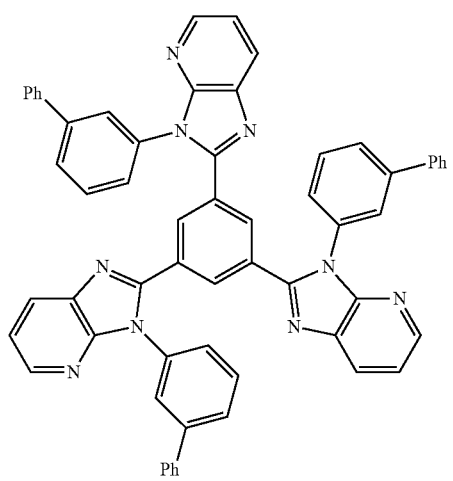
OM-12
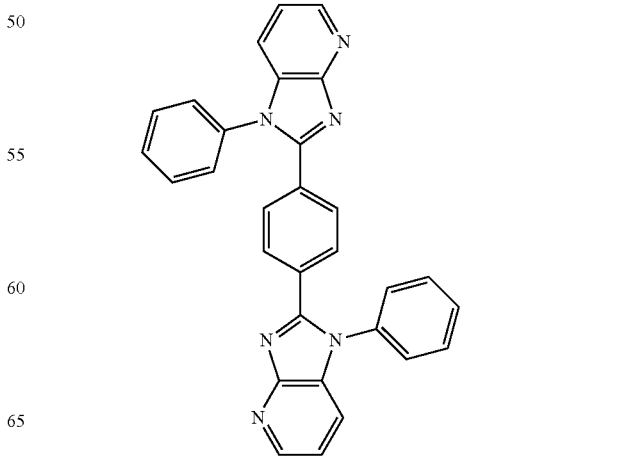

OM-13

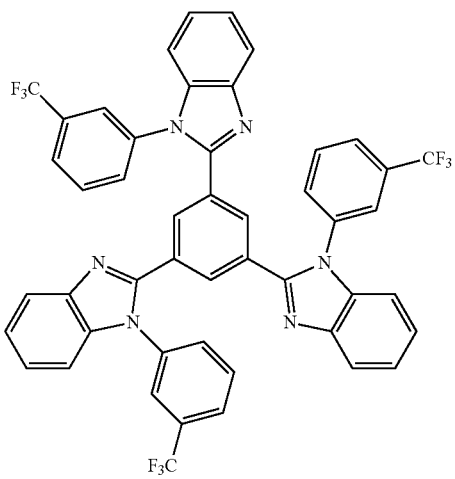

OM-16

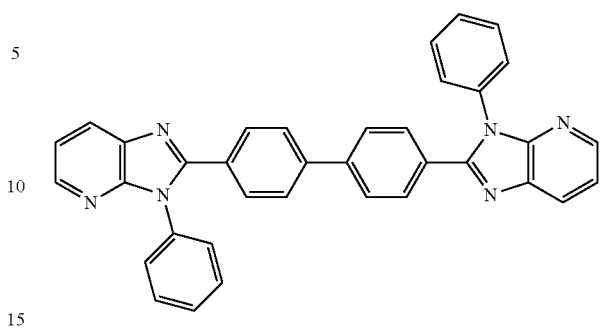

OM-14

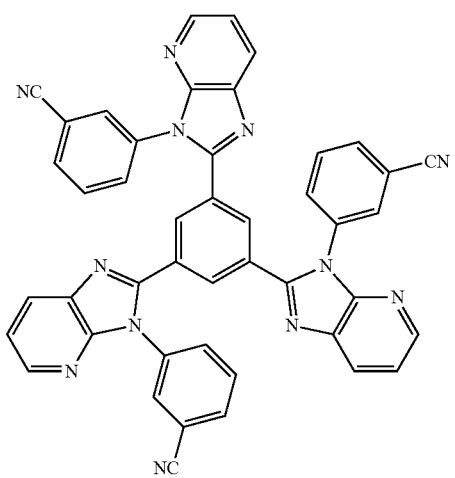

OM-15

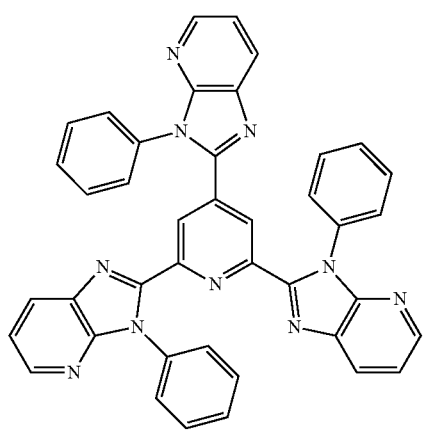

The compounds expressed by General Formula O-1 above can be synthesized by the method described in Japanese Laid-Open Patent Application 2001-335776. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the organic electroluminescent element of the present invention, a compound expressed by General Formula O-1 is preferably contained in an organic layer between the light-emitting layer and the cathode, but it is more preferably contained in the layer adjacent to the light-emitting layer on the cathode side.

The compound expressed by General Formula O-1 is preferably contained in an amount of 70 to 100 wt % and more preferably 85 to 100 wt % with respect to the total weight of the organic layer to which [this compound is] added.

The organic electroluminescent element of the present invention preferably includes at least one organic layer between the light-emitting layer and the cathode, and from the standpoints of the drive voltage and efficiency of the element, this organic layer preferably contains at least one type of compound expressed by General Formula P below. General Formula P will be described below:

[Forty-Second Chemical Formula]

General Formula P

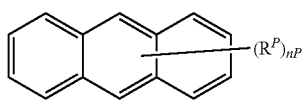

In General Formula P, $R^P$ represents an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. nP represents an integer from 1 to 10, and if there are a plurality of $R^P$ [groups], these may be the same or different. At least one $R^P$ is a substituent expressed by General Formulas P-1 to P-3 below:

[Forty-Third Chemical Formula]

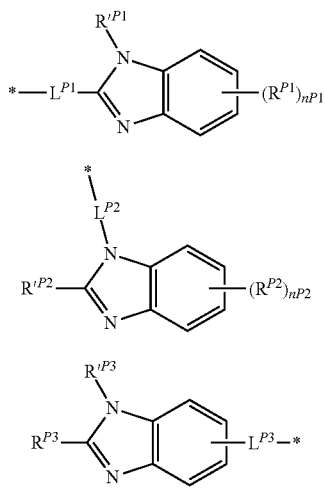

General Formula P-1

General Formula P-2

General Formula P-3

(In General Formulas P-1 to P-3, $R^{P1}$ to $R^{P3}$ and $R'^{P1}$ to $R'^{P3}$ each represent an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. $n^{P1}$ and $n^{P2}$ represent an integer from 0 to 4, and if there are a plurality of $R^{P1}$ to $R^{P3}$ and $R'^{P1}$ to $R'^{P3}$ [groups], these may be the same or different. $L^{P1}$ to $L^{P3}$ represent either a single bond or a divalent linking group composed of an aryl ring or a heteroaryl ring. The asterisk indicates the bonding position with an anthracene ring in General Formula P.)

A substituent favorable as $R^P$ other than the substituents expressed by P-1 to P-3 is an aryl group, and more preferably a phenyl group, a biphenyl group, a terphenyl group, or a naphthyl group, with a naphthyl group being even more preferable.

$R^{P1}$ to $R^{P3}$ and $R'^{P1}$ to $R'^{P3}$ are preferably either an aryl group or a heteroaryl group, more preferably an aryl group, and even more preferably a phenyl group, a biphenyl group, a terphenyl group, or a naphthyl group, with a phenyl group being most preferable.

$L^{P1}$ to $L^{P3}$ are preferably either a single bond or a divalent linking group composed of an aryl ring, more preferably a single bond, phenylene, biphenylene, terphenylene, or naphthylene, and even more preferably a single bond, phenylene, or naphthylene.

Concrete examples of the compounds expressed by General Formula P are given below, but it should not be construed that the compounds expressed by General Formula P that can be used in the present invention are limited to or by these concrete examples:

[Forty-Fourth Chemical Formula]

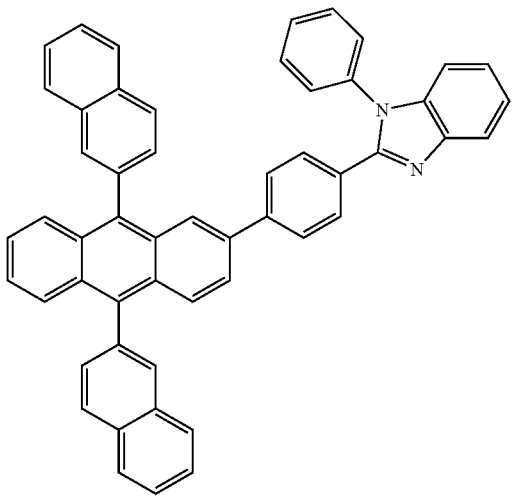

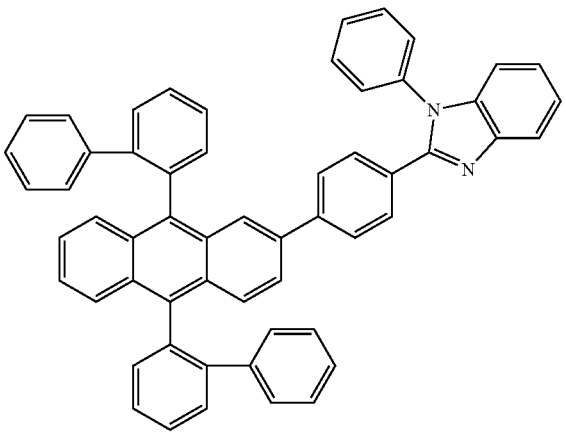

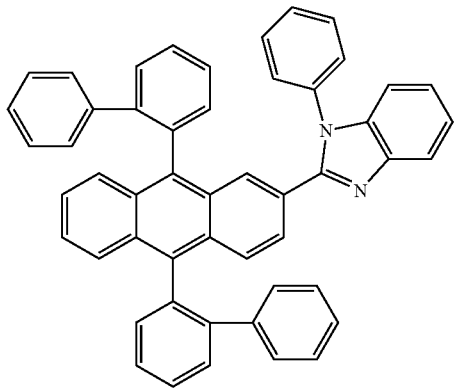

-continued
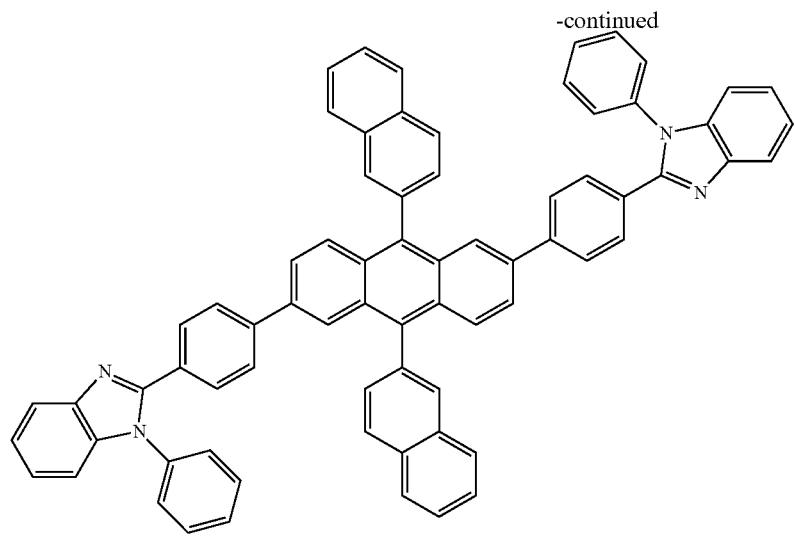
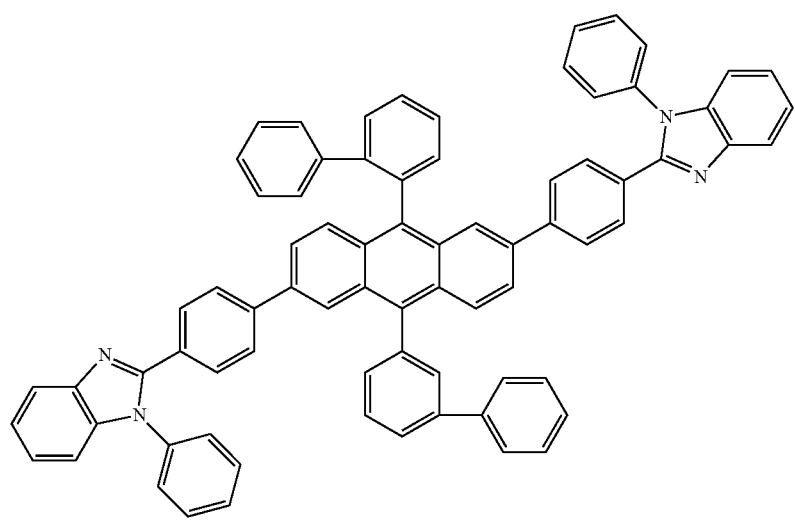
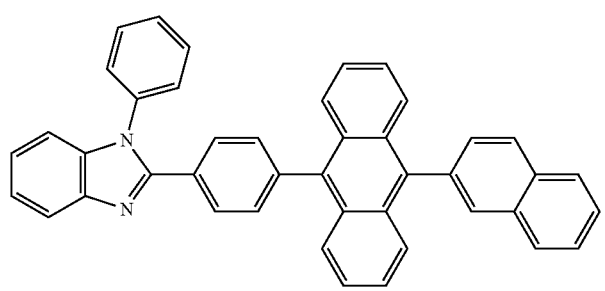
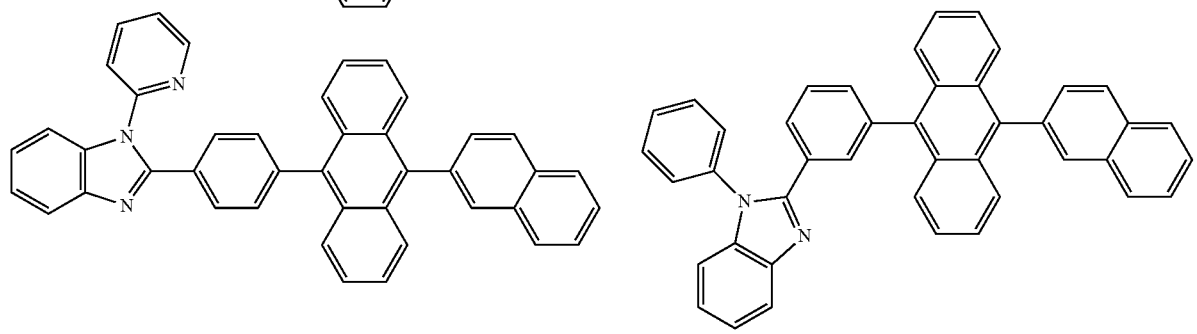

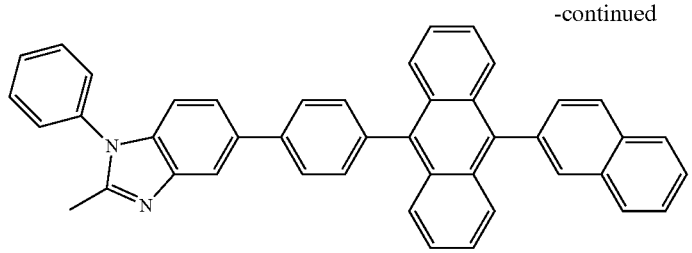

[Forty-Fifth Chemical Formula]

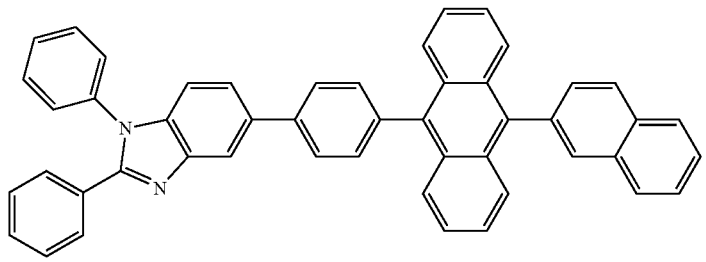

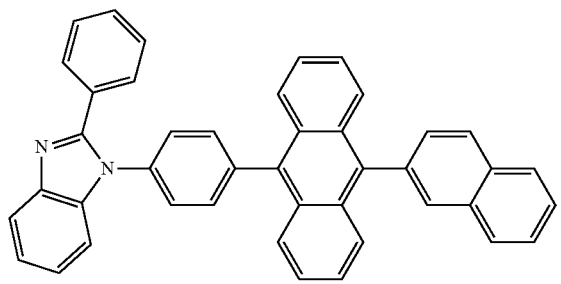 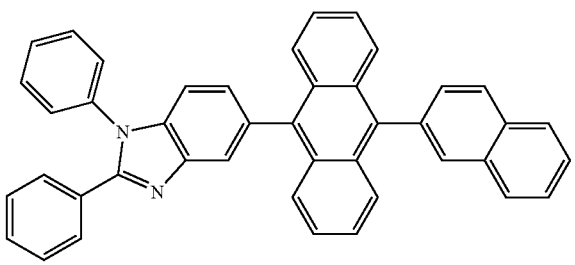

The compounds expressed by General Formula P above can be synthesized by the methods described in WO 2003/060956, WO 2004/080975, and the like. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the organic electroluminescent element of the present invention, the compound expressed by General Formula P is preferably contained in an organic layer between the light-emitting layer and the cathode, but it is more preferably contained in the layer adjacent to the cathode.

The compound expressed by General Formula P is preferably contained in an amount of 70 to 100 wt % and more preferably 85 to 100 wt % with respect to the total weight of the organic layer to which [this compound is] added.

<Protective Layer>

In the present invention, the entire organic electroluminescent element may be protected by a protective layer.

Regarding the protective layer, what is stated in paragraph numbers [0169] and [0170] in Japanese Laid-Open Patent Application 2008-270736 can be applied to the present invention. Note that the material of the protective layer may be either an inorganic material or organic material.

<Sealing Container>

The organic electroluminescent element of the present invention may be entirely sealed by using a sealing container.

Regarding the sealing container, what is stated in paragraph number [0171] in Japanese Laid-Open Patent Application 2008-270736 can be applied to the present invention.

<Drive Method>

The organic electroluminescent element of the present invention can emit light by applying direct current (may include an alternating current component as needed) voltage (usually 2 to 15 volts) or DC current between the anode and the cathode.

For the method for driving the organic electroluminescent element of the present invention, it is possible to apply the drive methods described in the respective Specifications or the like of Japanese Laid-Open Patent Applications H2-148687, H6-301355, H5-29080, H7-134558, H8-234685, and H8-241047, Japanese Patent 2,784,615, and U.S. Pat. Nos. 5,828,429 and 6,023,308.

The external quantum efficiency of the organic electroluminescent element of the present invention is preferably at least 5%, more preferably at least 6%, and even more preferably at least 7%. The numerical value of the external quantum efficiency that can be used is the maximum value for external quantum efficiency when the element is driven at 20° C., or the value for external quantum efficiency near 300 to 400 cd/m$^2$ when the element is driven at 20° C.

The internal quantum efficiency of the organic electroluminescent element of the present invention is preferably at least 30%, more preferably at least 50%, and even more preferably at least 70%. The internal quantum efficiency of the element is calculated by dividing the external quantum efficiency by the light extraction efficiency. The light extraction efficiency is approximately 20% with an ordinary organic EL element, but the light extraction efficiency can be raised to over 20% by modifying the shape of the substrate, the shape of the electrodes, the thickness of the organic layers, the thickness of the inorganic layers, the refractive index of the organic layers, the refractive index of the inorganic layers, and so forth.

<Emission Wavelength>

There are no particular restrictions on the emission wavelength of the organic electroluminescent element of the present invention, but it is preferably used for emission of blue light or white light. Of these, with the organic electroluminescent element of the present invention, it is preferable to use a compound expressed by General Formula 1-1 above as the light-emitting material to cause emission of light, and it is especially preferable to cause emission of blue light.

<Applications of the Organic Electroluminescent Element of the Present Invention>

The organic electroluminescent element of the present invention can be utilized favorably in display elements, displays, backlights, electronic photography, illumination light sources, recording light sources, exposure light sources, reading light sources, road signs, trade signs, interior decorating, optical communications, and so forth. [This element] can be especially favorably used in devices that are driven in areas of high light emission brightness, such as in light-emitting devices, lighting devices, and display devices.

Light-Emitting Device

The light-emitting device of the present invention is characterized by including the organic electroluminescent element of the present invention.

Next, the light-emitting device of the present invention will be described with reference to FIG. 2.

The light-emitting device of the present invention makes use of the aforementioned organic electroluminescent element.

Figure 2:
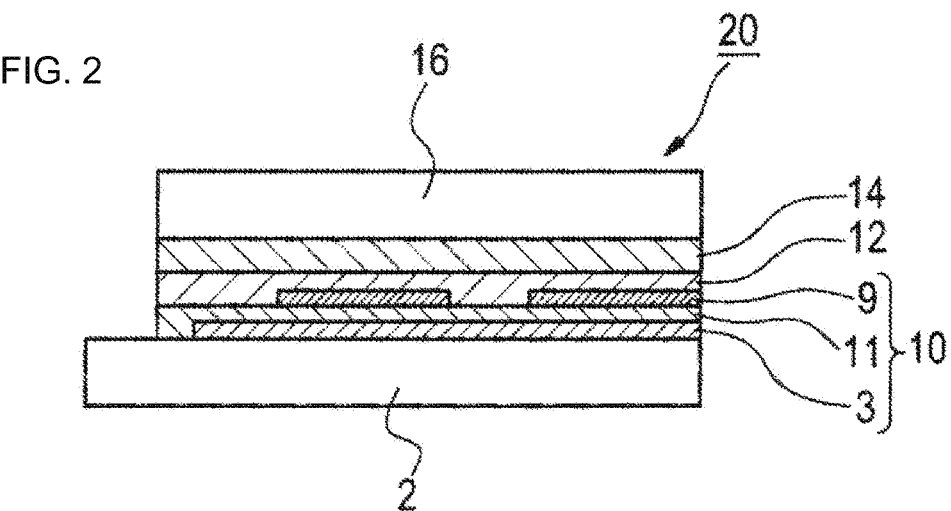
FIG. 2 is a schematic diagram illustrating one example of the light-emitting device according to the present invention.

FIG. 2 is a sectional view schematically showing one example of the light-emitting device of the present invention. The light-emitting device 20 in FIG. 2 is made up of a transparent substrate (support substrate) 2, an organic electroluminescent element 10, a sealing container 16, and the like.

The organic electroluminescent element 10 is configured such that an anode (first electrode) 3, an organic layer 11, and a cathode (second electrode) 9 are sequentially laminated over the substrate 2. Furthermore, a protective layer 12 is laminated over the cathode 9, and in addition, the sealing container 16 is provided on the protective layer 12 via an adhesive layer 14. Note that parts of the electrodes 3 and 9, partitions, insulating layers, and so forth are not depicted.

Here, an epoxy resin or other such photosetting adhesive or thermosetting adhesive can be used as the adhesive layer 14. For example, a thermosetting adhesive sheet can also be used.

There are no particular restrictions on the applications of the light-emitting device of the present invention, but examples other than lighting devices include television sets, personal computers, portable telephones, electronic paper, and other such display devices.

Lighting Device

The lighting device of the present invention is characterized by including the organic electroluminescent element of the present invention.

Next, the lighting device of the present invention will be described with reference to FIG. 3.

Figure 3:
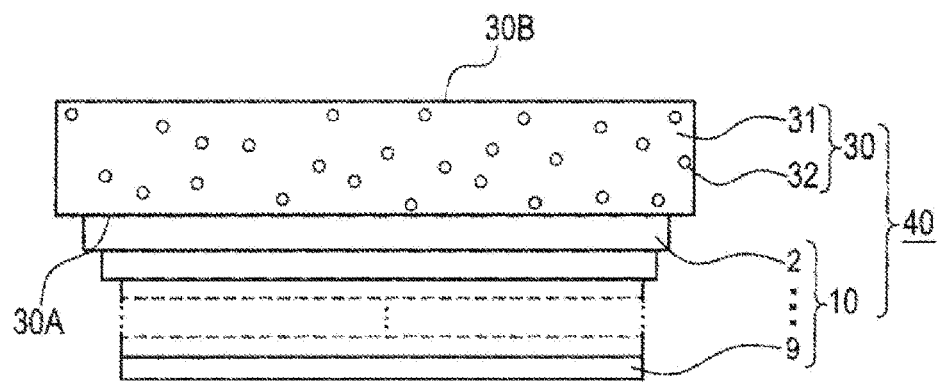
FIG. 3 is a schematic diagram illustrating one example of the lighting device according to the present invention.

FIG. 3 is a sectional view schematically showing one example of the lighting device of the present invention. As is shown in FIG. 3, the lighting device 40 of the present invention comprises the aforementioned organic EL element 10 and a light-scattering member 30. In more concrete terms, the lighting device 40 is configured such that the substrate 2 of the organic EL element 10 is in contact with the light-scattering member 30.

There are no particular restrictions on the light-scattering member 30 as long as it is capable of scattering light, but in FIG. 3, it is a member in which microparticles 32 are dispersed in a transparent substrate 31. A glass substrate, for example, can be used favorably as the transparent substrate 31. Transparent resin microparticles can be used favorably as the microparticles 32. The glass substrate and the transparent resin microparticles can both be from prior art. This type of lighting device 40 is devised such that when light emitted from the organic electroluminescent element 10 is incident on a light incidence face 30A of the light-scattering member 30, the incident light is scattered by the light-scattering member 30, and the scattered light exits a light emission face 30B as illuminating light.

Display Device

The display device of the present invention is characterized by including the organic electroluminescent element of the present invention.

Examples of the display device of the present invention include television sets, personal computers, portable telephones, electronic paper, and other such display devices.

WORKING EXAMPLES

The characteristic features of the present invention will be described below in more concrete terms by giving working examples and comparative examples. The materials, usage amounts, proportions, processing details, processing procedures, and so forth mentioned in the following working examples can be suitably modified as long as there is no departure from the gist of the present invention. Therefore, it should not be construed that the scope of the present invention is limited to or by the concrete examples given below.

The structural formulas of the compounds used in the working examples and comparative examples are shown altogether below:

Compounds of Working Examples
[Forty-Sixth Chemical Formula (1)]
compound 1
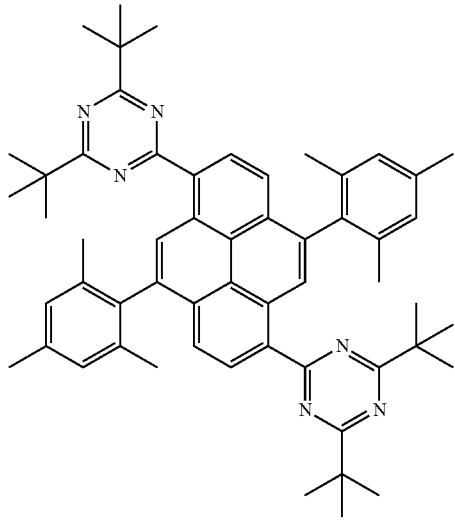
compound 2
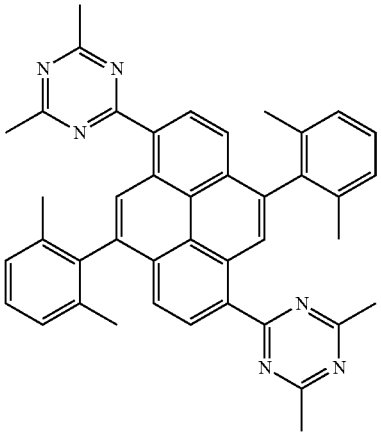
compound 3
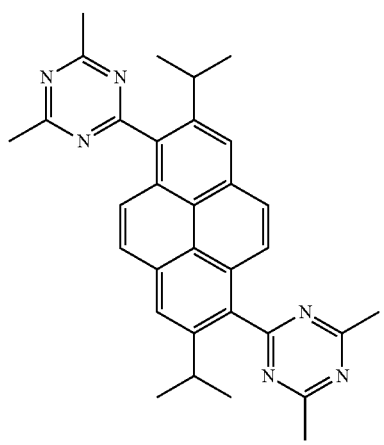
compound 4
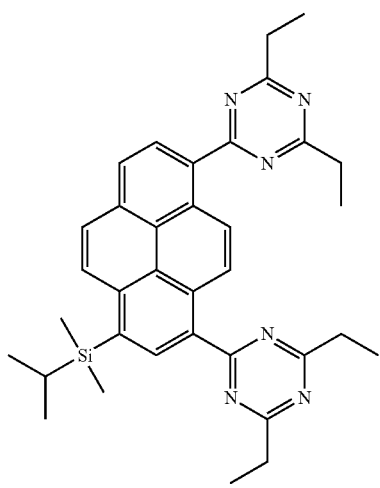
compound 5
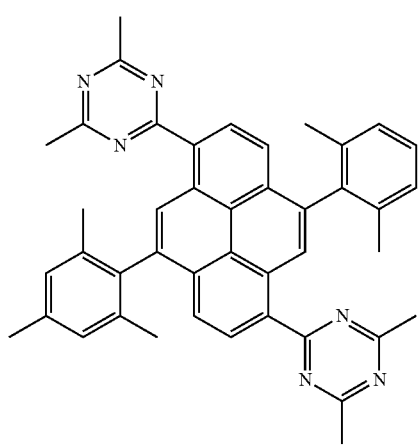
compound 6
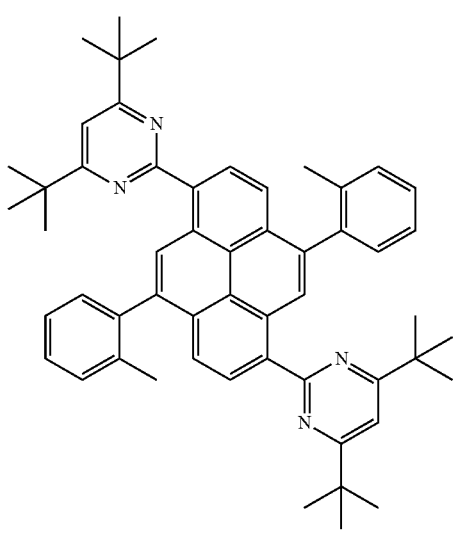

-continued
compound 7
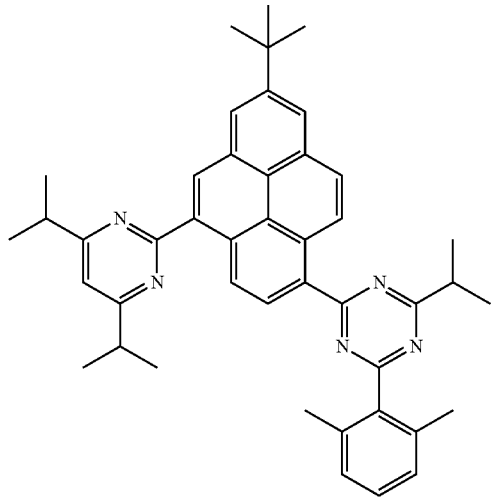
compound 8
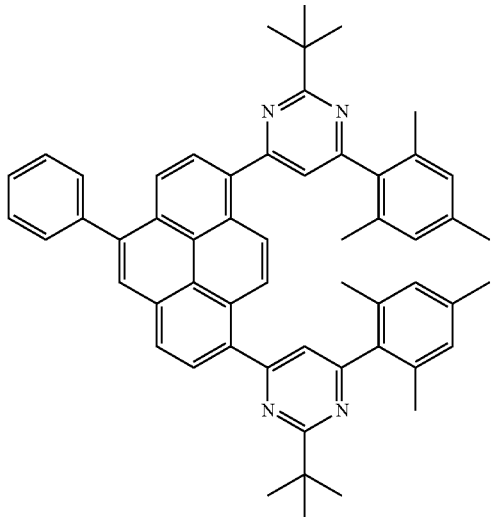
compound 9
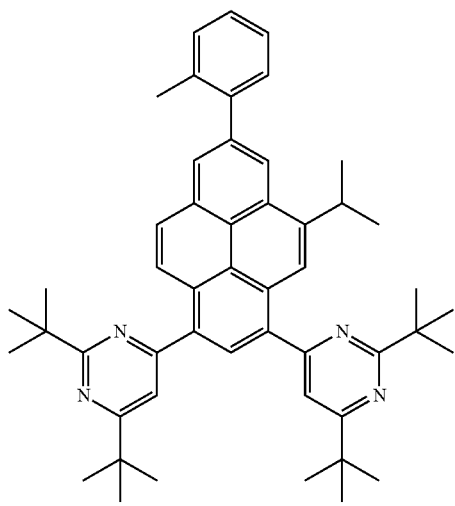
compound 10
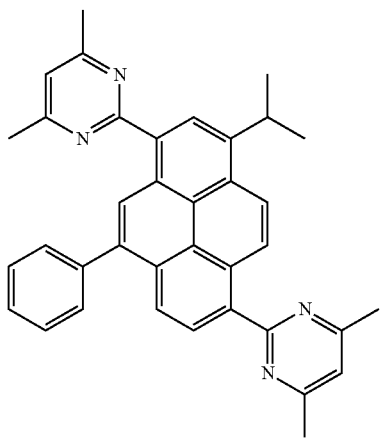
compound 11
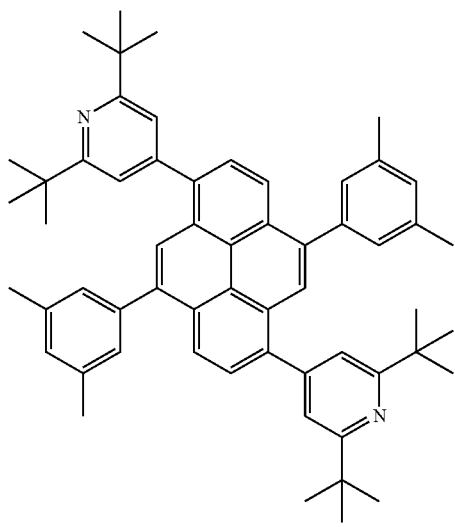
compound 12
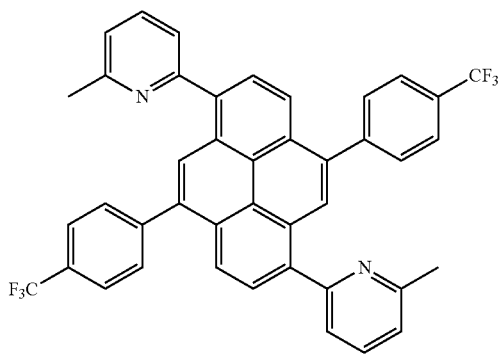

-continued
compound 13
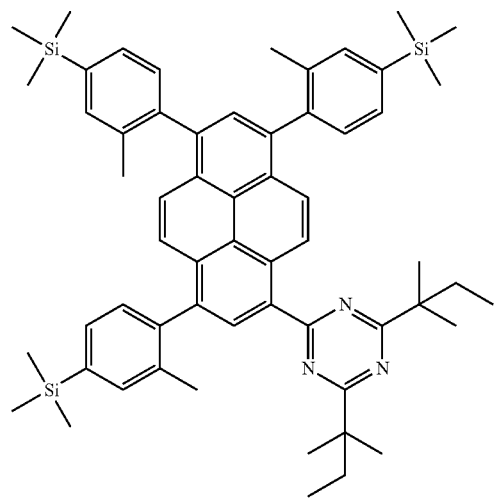
compound 14
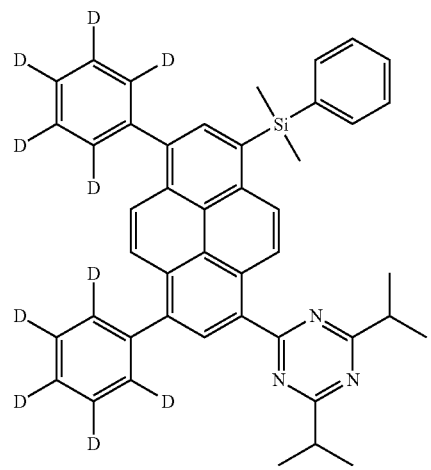
compound 15
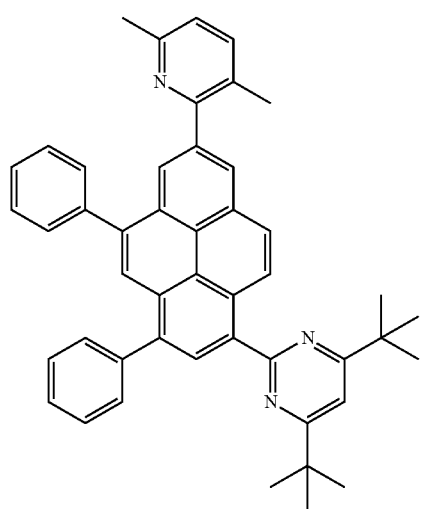
compound 16
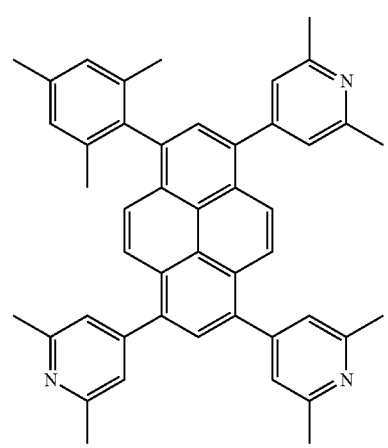
compound 17
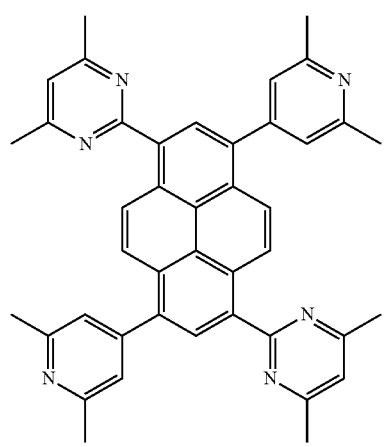

-continued
Compounds of Working Examples
Comparative compound 1
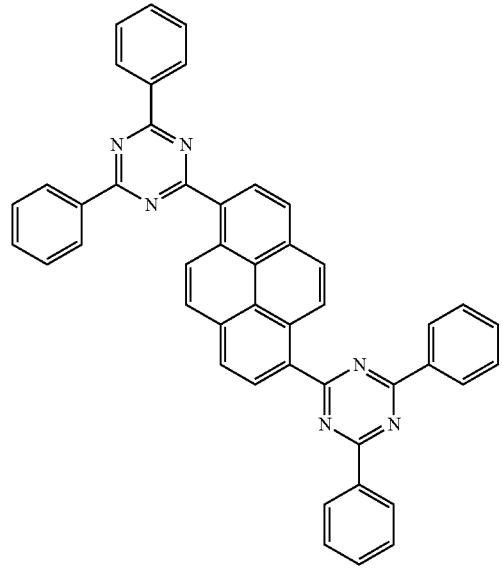
JP-A-2010-138121
Comparative compound 2
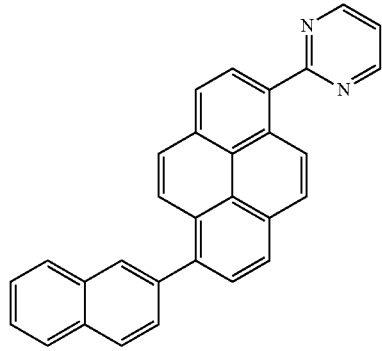
JP-A-2011-14886
Comparative compound 3
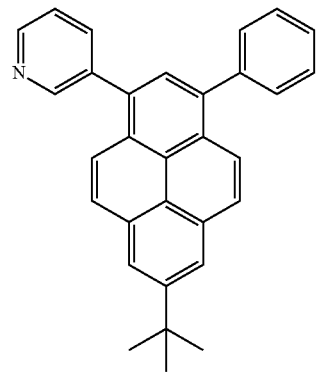
WO 2010-113743
Comparative compound 4
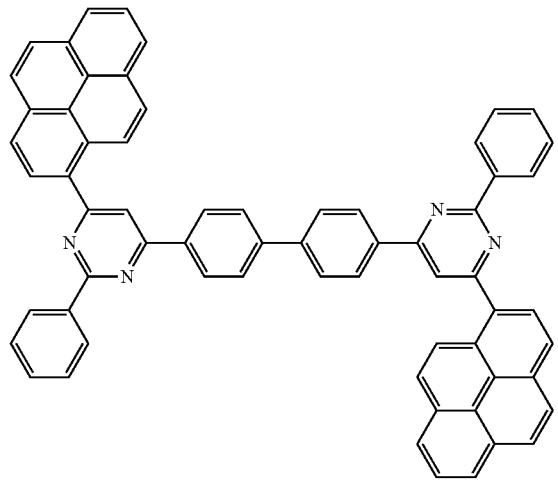
WO 2011-005060

-continued
Comparative compound 5
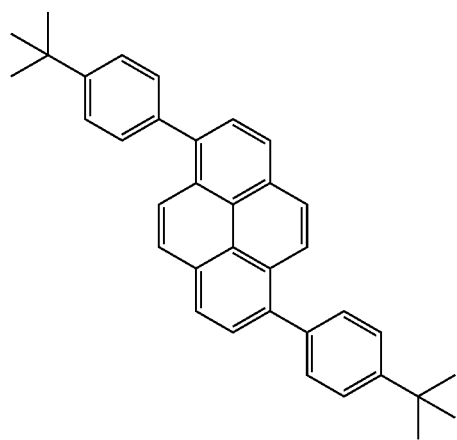
EP 1437395
Comparative compound 6
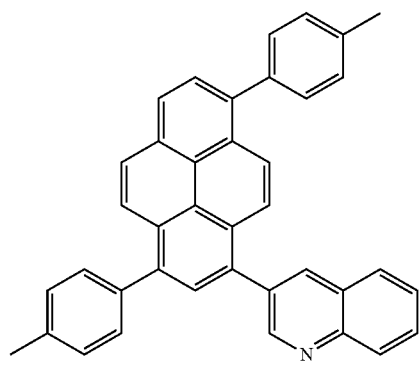
JP-A-2007-131723
Comparative compound 7
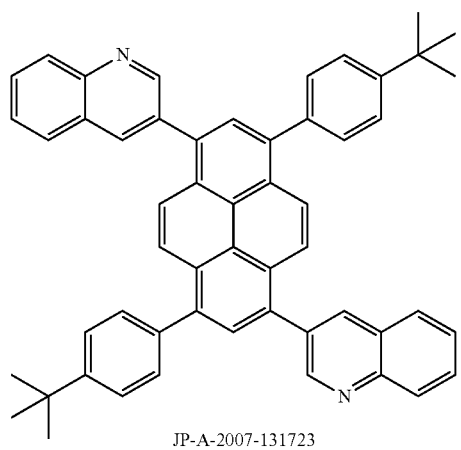
JP-A-2007-131723
[Forty-Sixth Chemical Formula (2)]
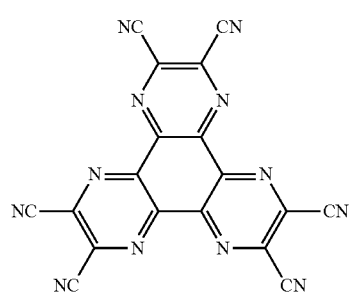
HAT-CN HI-1
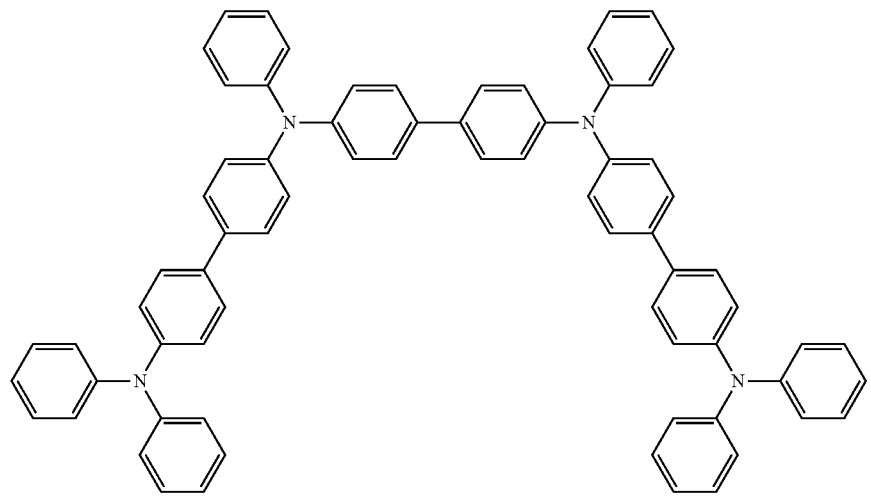
HI-2
HT-1
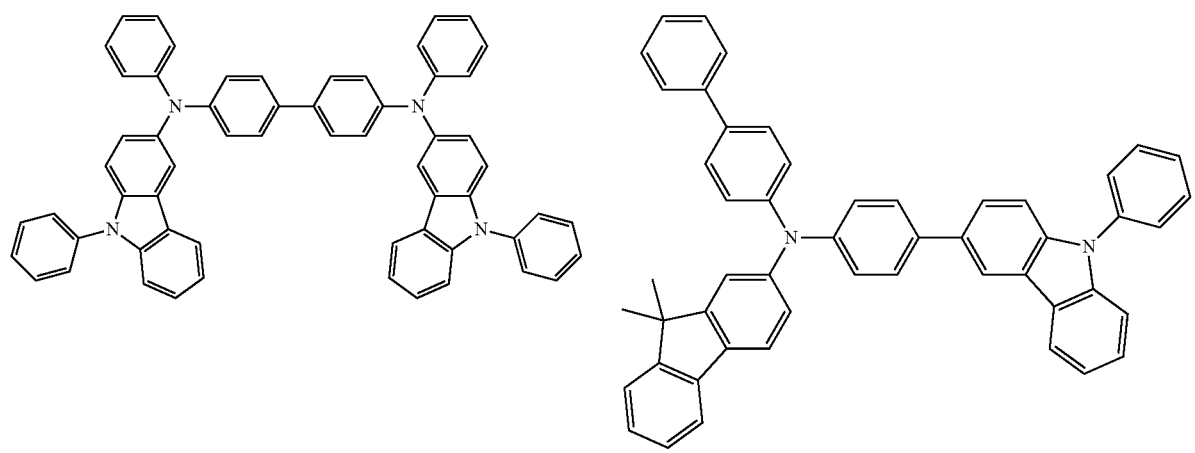
HT-2
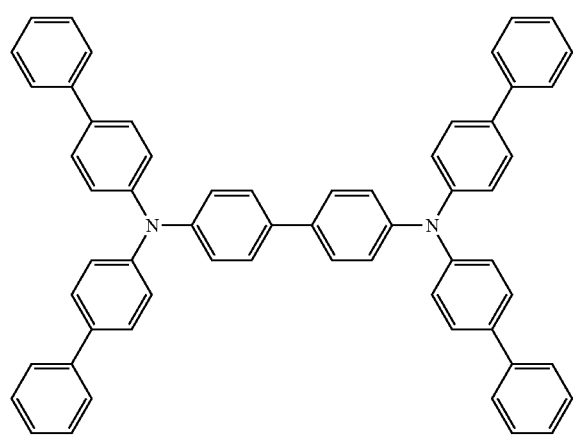

-continued
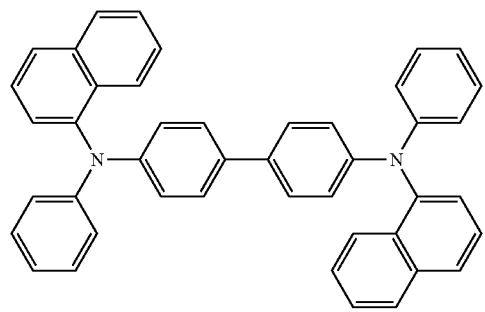
NPD
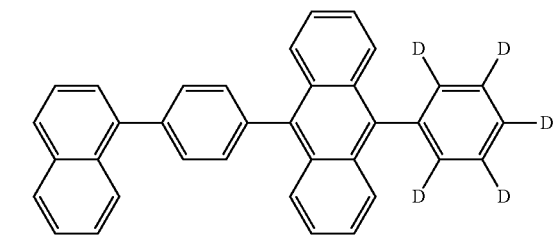
H-2
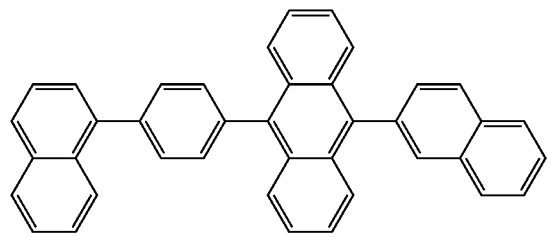
H-3
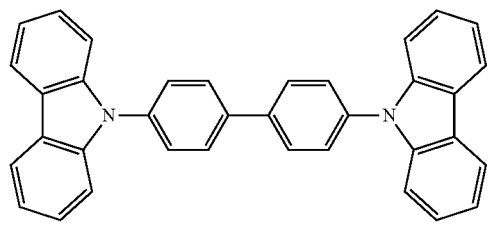
CBP
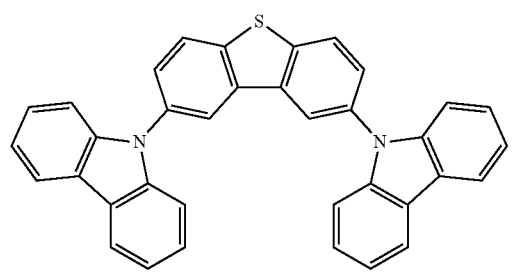
H-4
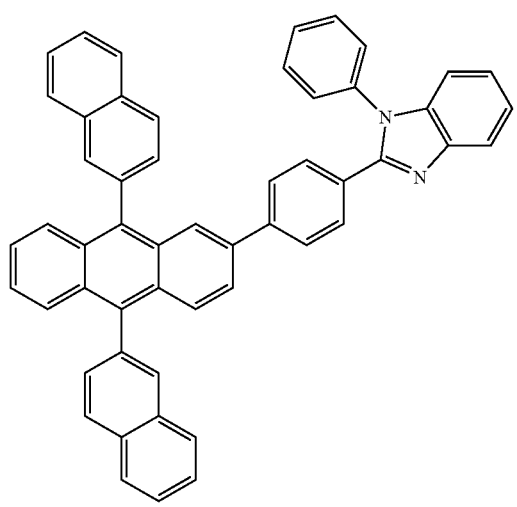
ET-1
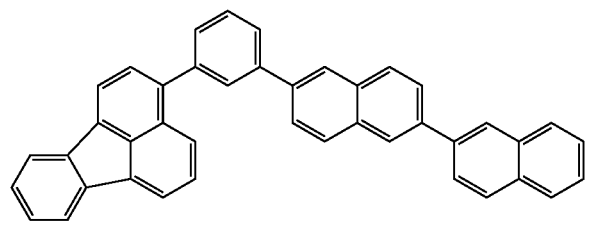
ET-2
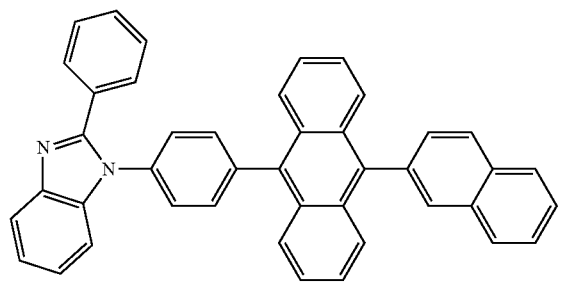
ET-3

ET-4

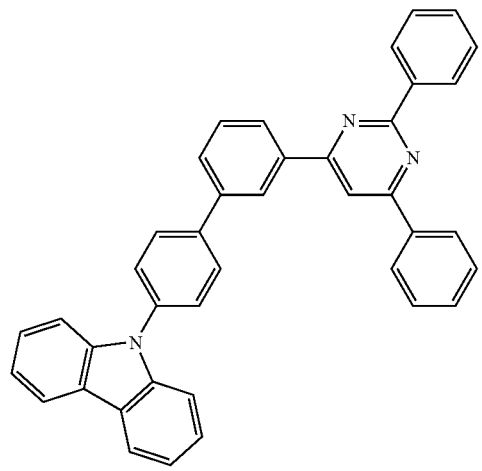

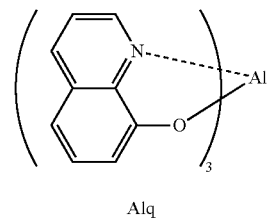

Alq

ET-5

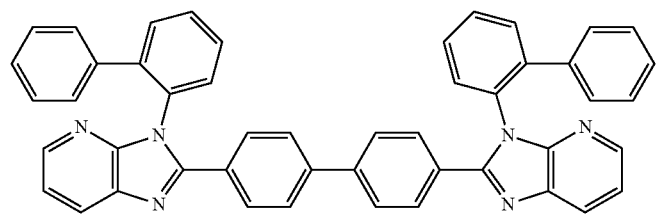

30

1. Synthesis Example

The compounds expressed by General Formula 1-1 above can be synthesized by the methods described in this Specification or by a combination of other publicly known reactions. Typical examples of concrete procedures for synthesizing the compounds expressed by General Formula 1-1 above will be described below:

(Synthesis Example 1) Synthesis of Compound 1

[Forty-Seventh Chemical Formula]

-continued

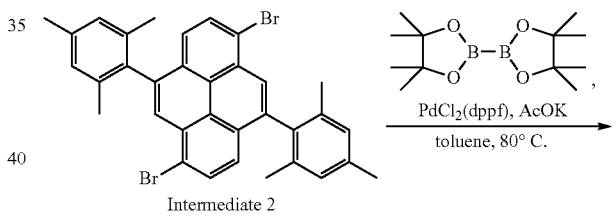

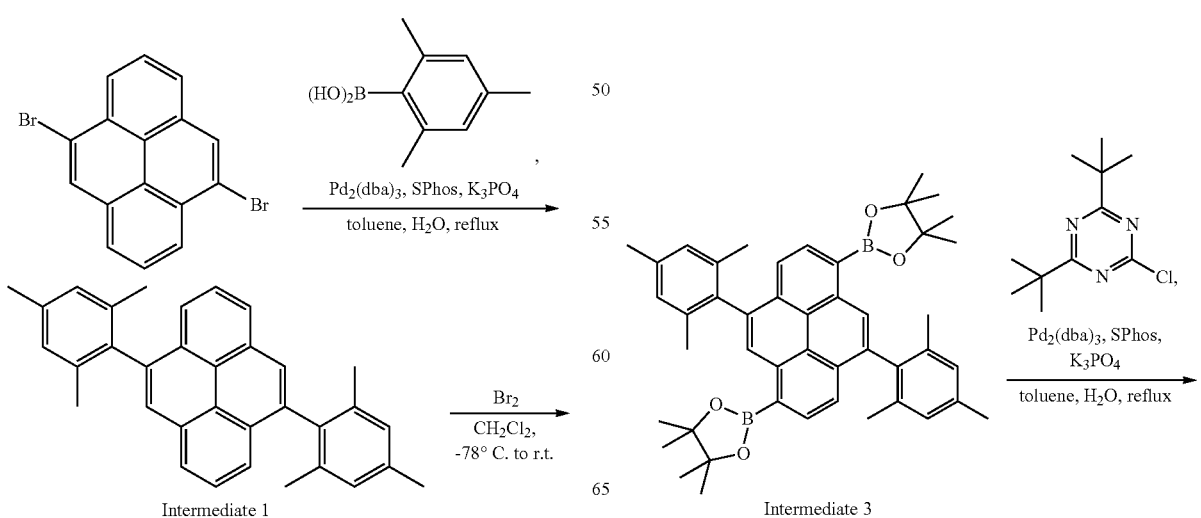

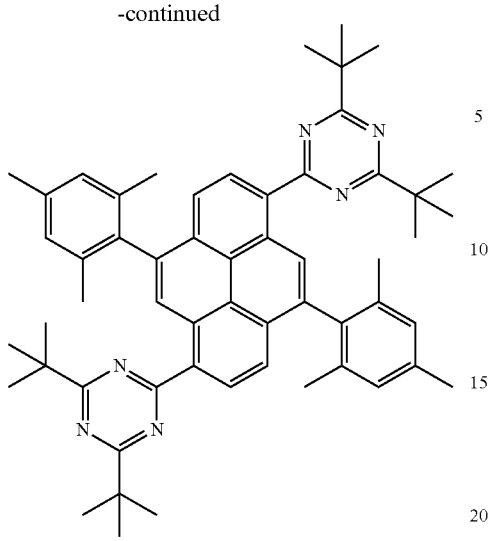

Compound 1

Intermediate 3 was synthesized by means of the synthesis scheme above with reference to publicly known literature. The 5,10-dibromopyrene was synthesized by the method recited in Synthesis, 1989, pp. 356-359, while the 2-chloro-4,6-di-t-butyl-1,3,5-triazine was synthesized by the method recited in Angew. Chem. Int. Ed. 2008, 47, pp. 8246-8250.

1.49 g (2.50 mmol) of intermediate 2, 1.20 g (5.25 mmol) of 2-chloro-4,6,-di-t-butyl-1,3,5-triazine, 137 mg (0.15 mmol) of tris(dibenzylideneacetone)dipalladium ($Pd_2(dba)_3$), 246 mg (0.60 mmol) of 2-dicyclohexylphosphino-2',6'-dimethoxybiphenyl (SPhos), and 2.12 g (10.00 mmol) of potassium phosphate were mixed, and [the mixture] was heated to reflux for 2 hours under a nitrogen atmosphere. After the reaction solution was returned to room temperature, ethyl acetate and pure water were added, and the organic layer was extracted. The organic layer was dried with sodium sulfate and subjected to vacuum concentration, and after purification by silica gel column chromatography (developing solvent: toluene/hexane=1:4), this was further washed with methanol/ethanol (1:1), which gave 0.67 g of compound 1 (yield 33%).

$^1$H NMR (400 MHz, in $CDCl_3$); δ (ppm)=9.12 (s, 2H), 8.67 (d, 2H), 7.88 (d, 2H), 7.05 (s, 4H), 2.42 (s, 6H), 2.03 (s, 12H), 1.43 (s, 36H) ppm. MS (MALDI-TOF): m/z=820.6 ([M+H]$^+$).

The aforementioned compounds 2 to 17 used in the working examples were also synthesized by methods similar to the one used for the compound 1. Comparative compounds 1 to 5 were synthesized by referring to publicly known documents in which the respective compounds are recited.

2. Evaluations of Material Properties (a) Evaluation of the Emission Wavelength A thin film was formed in a thickness of 50 nm by a vacuum vapor deposition method over a quartz glass substrate measuring 2.5 cm$^2$ and 0.7 mm thick such that the weight ratio of H-1 below and the various light-emitting materials is 99:1, and aluminum (100 nm) was vapor-deposited over this. The film thus obtained was irradiated with UV light of 350 nm, and the emission spectrum at the time of light emission was measured using a spectrofluorometer (FP-6300 made by JASCO).

[Forty-Eighth Chemical Formula]

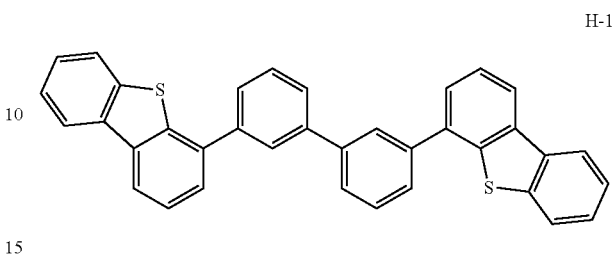

H-1

The maximum emission wavelength was evaluated in three levels on the following basis:

○: at least 440 nm and less than 455 nm

Δ: less than 440 nm x: at least 455 nm

Figure 4:
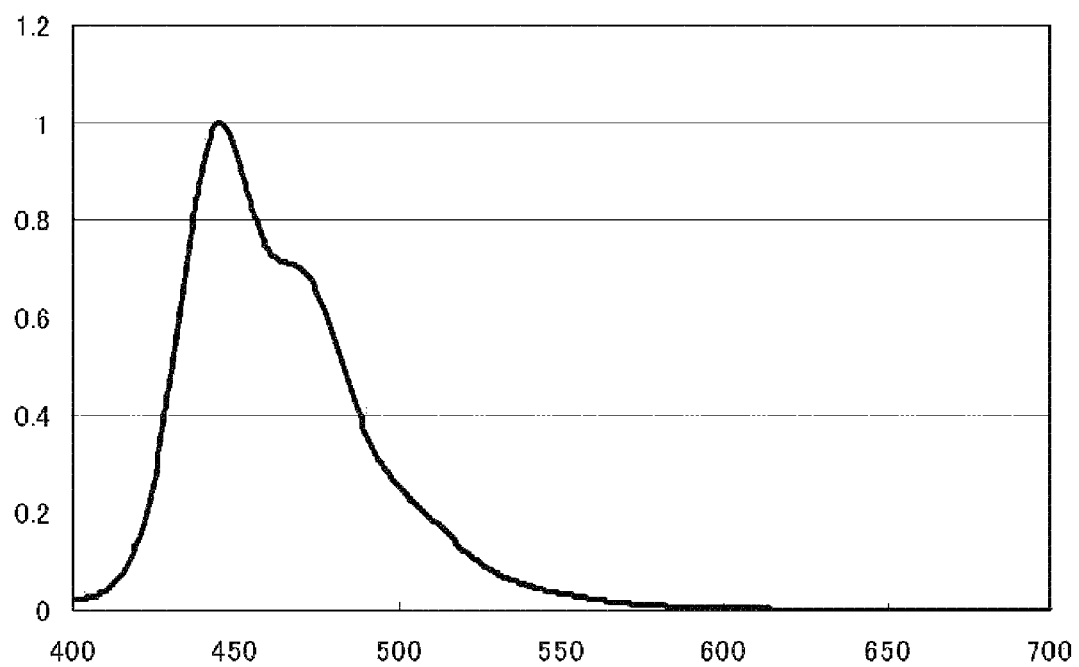
FIG. 4 is a schematic diagram illustrating one example of the emission spectrum of the material for an organic electroluminescent element according to the present invention.

Furthermore, the emission spectrum of the compound 1 is shown in FIG. 4 as an example. In FIG. 4, the horizontal axis indicates the emission wavelength (unit: nm). Moreover, the vertical axis indicates the emission intensity, representing a relative intensity when the emission intensity at the maximum emission wavelength is 1.0.

(b) Evaluation of the Spectral Full Width at Half Maximum

The spectral full width at half maximum FWHM (1%) (energy conversion) in the aforementioned emission spectrum was evaluated in three levels on the following basis:

○: less than 0.30 eV

Δ: at least 0.30 eV and less than 0.33 eV x: at least 0.33 eV (c) Evaluation of Suppression of Aggregation Auxiliary Light Emission Other than changing the weight ratio of the aforementioned compound H-1 and the various light-emitting materials to 93:7, the spectral full width at half maximum (FWHM) (7%) was measured in the same manner as in (b) Evaluation of the Spectral Full Width at Half Maximum in films produced in the same manner as in (a) Evaluation of the Emission Wavelength. The ratio of spectral full width at half maximum of the 7%-doped film and the 1%-doped film of each light-emitting material (FWHM (7%)/FWHM (1%)) was evaluated in three levels on the following basis:

○: less than 1.1

Δ: at least 1.1 and less than 1.2 x: at least 1.2

(d) Evaluation of Suitability to Vapor Deposition 20 mg of each compound was used to perform vacuum TG/DTA measurement (rate of temperature rise: 2° C./minute; degree of vacuum: approximately 10$^{-2}$ Pa), and the temperature at decrease of 10 wt % was evaluated in two levels on the following basis:

○: lower than 300° C.

x: 300° C. or higher

The results obtained in the aforementioned evaluations of material properties (a) to (d) are given in Table 1 below:

TABLE 1

| Compound | Emission wavelength | Spectral full width at half maximum | Suppression of aggregation auxiliary light emission | Suitability to vapor deposition |
|---|---|---|---|---|
| Compound 1 | ○ | ○ | ○ | ○ |
| Compound 2 | ○ | ○ | ○ | ○ |
| Compound 3 | ○ | ○ | ○ | ○ |
| Compound 4 | ○ | ○ | ○ | ○ |
| Compound 5 | ○ | ○ | ○ | ○ |
| Compound 6 | ○ | ○ | ○ | ○ |
| Compound 7 | ○ | ○ | ○ | ○ |
| Compound 8 | ○ | ○ | Δ | ○ |
| Compound 9 | ○ | ○ | ○ | ○ |
| Compound 10 | ○ | ○ | ○ | ○ |
| Compound 11 | ○ | ○ | ○ | ○ |
| Compound 12 | ○ | ○ | ○ | ○ |
| Compound 13 | ○ | ○ | ○ | ○ |
| Compound 14 | ○ | ○ | Δ | ○ |
| Compound 15 | ○ | ○ | Δ | ○ |
| Compound 16 | ○ | ○ | ○ | ○ |
| Compound 17 | ○ | ○ | ○ | ○ |
| Comparative compound 1 | x | Δ | x | x |
| Comparative compound 2 | Δ | x | x | ○ |
| Comparative compound 3 | Δ | x | x | ○ |
| Comparative compound 4 | Δ | x | x | x |
| Comparative compound 5 | Δ | x | x | ○ |
| Comparative compound 6 | ○ | x | x | ○ |
| Comparative compound 7 | x | x | x | x |

3. Production and Evaluation of Organic Electroluminescent Elements

All the materials used in the production of the organic electroluminescent elements were subjected to sublimation purification, and it was confirmed by high-performance liquid chromatography (Tosoh TSK gel ODS-100Z) that the purity (absorption intensity surface area ratio at 254 nm) was 99.9% or higher.

Working Example 1

A glass substrate (made by Geomatec Co., surface resistance of 10 ohms/square) having an ITO film measuring 2.5 cm$^2$ and 0.5 mm thick was put into a washing vessel and ultrasonically washed in 2-propanol, upon which it was subjected to treatment with UV-ozone for 30 minutes. The following organic compound layers were sequentially deposited onto this transparent anode (ITO film) by a vacuum vapor deposition method:

First layer: HAT-CN; film thickness of 10 nm
Second layer: HT-1; film thickness of 30 nm
Third layer: H-2 and the light-emitting material listed in Table 2 (weight ratio of 97:3); film thickness of 30 nm
Fourth layer: ET-1; film thickness of 30 nm Over this, lithium fluoride (1 nm) and metallic aluminum (100 nm) were vapor-deposited in this order to form a cathode.

Without being allowed to come into contact with the air, the laminate thus obtained was placed in a glove box that had been replaced with nitrogen gas, and was sealed using a glass sealing jar and a UV-setting adhesive (XNR5516HV, made by Nagase Chiba[7]), which gave organic electroluminescent elements 1-1 to 1-10 and comparative organic electroluminescent elements 1-1 to 1-5, in which the emission portion measured 2 mm square. The various organic electroluminescent elements thus obtained were tested as follows. The evaluation results from the standpoints of luminous efficiency, color purity, and changes in chromaticity after driving are given in Table 2 below:

[7]Translator's note: "Nagase Chiba" is now called "Nagase ChemteX."

(a) Luminous Efficiency

Using a source measurement unit 2400 made by Toyo Technica, DC voltage was applied to each element to cause it to emit light, and the brightness thereof was measured using a brightness meter (BM-8 made by Topcon). The emission wavelength and the emission spectrum were measured using a PMA-11 spectrum analyzer made by Hamamatsu Photonics. Based on these [results], the external quantum efficiency ($\eta$) when the brightness was close to 1000 cd/m$^2$ was calculated by a brightness conversion method. This was expressed in Table 2 below as a relative value, with the value of the external quantum efficiency of comparative element 1-1 being set at 1.0. Larger numbers indicate higher efficiency and are therefore preferable.

(b) Color Purity

The chromaticity (x, y) (in the CIE 1931 color space) was found from the emission spectrum when each organic electroluminescent element was caused to emit light such that the brightness would be 1000 cd/m$^2$. The y value at this time was evaluated in four levels on the following basis:

◎: lower than 0.09
○: 0.09 or higher and lower than 0.12
Δ: 0.12 or higher and lower than 0.15
x: 0.15 or higher (c) Changes in Chromaticity after Driving DC voltage was applied to make each organic electroluminescent element emit light continuously such that the brightness would be 1000 cd/m$^2$, and the chromaticity (x', y') (in the CIE 1931 color space) at the point when the brightness decreased to 500 cd/m$^2$ was found from the emission spectrum. The change in the y value $\Delta y$ ($=|y'-\Delta y|$) [sic][8] before and after drive deterioration was evaluated in four levels on the following basis:

◎: less than 0.01
○: 0.01 or more and less than 0.02
Δ: 0.02 or more and less than 0.03
x: 0.03 or more

[8]Translator's note: The change in y ($\Delta y$) cannot be expressed in terms of $\Delta y$ (this is circular logic). There must be an error in this formula "$\Delta y$ ($=|y'-\Delta y|$)" in the original. Probably it should be "$\Delta y$ ($=|y'-y|$)" [just delete the second $\Delta$].

TABLE 2

| Element number | Light-emitting material | Emission color | Color purity | Luminous efficiency (relative value) | Change in chromaticity after driving |
|---|---|---|---|---|---|
| Element 1-1 | Compound 1 | blue | ◎ | 1.4 | ◎ |
| Element 1-2 | Compound 3 | blue | ◎ | 1.3 | ◎ |
| Element 1-3 | Compound 5 | blue | ◎ | 1.4 | ◎ |
| Element 1-4 | Compound 6 | blue | ◎ | 1.3 | ◎ |
| Element 1-5 | Compound 7 | blue | ○ | 1.3 | ◎ |
| Element 1-6 | Compound 12 | blue | ○ | 1.3 | ◎ |
| Element 1-7 | Compound 13 | blue | ○ | 1.3 | ◎ |
| Element 1-8 | Compound 15 | blue | ○ | 1.3 | ○ |
| Element 1-9 | Compound 16 | blue | ○ | 1.3 | ◎ |
| Element 1-10 | Compound 17 | blue | ◎ | 1.4 | ◎ |
| Comparative | Comparative | blue | x | 1.0 | x |

TABLE 2-continued

| Element number | Light-emitting material | Emission color | Color purity | Luminous efficiency (relative value) | Change in chromaticity after driving |
|---|---|---|---|---|---|
| element 1-1 | compound 1 | green | | | |
| Comparative element 1-2 | Comparative compound 2 | blue | Δ | 0.53 | × |
| Comparative element 1-3 | Comparative compound 3 | blue | Δ | 0.38 | × |
| Comparative element 1-4 | Comparative compound 4 | blue | Δ | 0.33 | × |
| Comparative element 1-5 | Comparative compound 5 | blue | Δ | 0.45 | × |
| Comparative element 1-6 | Comparative compound 6 | blue | × | 0.81 | × |
| Comparative element 1-7 | Comparative compound 7 | blue green | × | 0.94 | × |

Working Example 2

Other than changing the layer configuration as shown below, organic electroluminescent elements were produced in the same manner as in Working Example 1, and the same evaluations as in Working Example 1 were made. The results are shown in Table 3 below. Note that the luminous efficiency in Table 3 below is expressed as a relative value, with the external quantum efficiency of comparative element 2-1 being set at 1.0.

First layer: HI-2; film thickness of 50 nm
Second layer: HT-2; film thickness of 45 nm
Third layer: H-3 and the light-emitting material listed in Table 3 (weight ratio of 97:3); film thickness of 25 nm
Fourth layer: ET-2; film thickness of 5 nm
Fifth layer: ET-3; film thickness of 20 nm

TABLE 3

| Element number | Light-emitting material | Emission color | Color purity | Luminous efficiency (relative value) | Change in chromaticity after driving |
|---|---|---|---|---|---|
| Element 2-1 | Compound 2 | blue | ◎ | 1.4 | ◎ |
| Element 2-2 | Compound 5 | blue | ◎ | 1.4 | ◎ |
| Element 2-3 | Compound 6 | blue | ◎ | 1.4 | ◎ |
| Element 2-4 | Compound 7 | blue | ○ | 1.3 | ◎ |
| Element 2-5 | Compound 8 | blue | ○ | 1.3 | ○ |
| Element 2-6 | Compound 9 | blue | ◎ | 1.3 | ◎ |
| Element 2-7 | Compound 10 | blue | ○ | 1.3 | ○ |
| Element 2-8 | Compound 14 | blue | ○ | 1.3 | ○ |
| Comparative element 2-1 | Comparative compound 1 | blue green | × | 1.0 | × |
| Comparative element 2-2 | Comparative compound 2 | blue | Δ | 0.59 | × |
| Comparative element 2-3 | Comparative compound 3 | blue | Δ | 0.44 | × |
| Comparative element 2-4 | Comparative compound 4 | blue | Δ | 0.47 | × |
| Comparative element 2-5 | Comparative compound 5 | blue | Δ | 0.52 | × |
| Comparative element 2-6 | Comparative compound 6 | blue | × | 0.78 | × |
| Comparative element 2-7 | Comparative compound 7 | blue green | × | 0.96 | × |

Working Example 3

Other than changing the layer configuration as shown below, organic electroluminescent elements were produced in the same manner as in Working Example 1, and the same evaluations as in Working Example 1 were made. The results are shown in Table 4 below. Note that the luminous efficiency in Table 4 below is expressed as a relative value, with the external quantum efficiency of comparative organic electroluminescent element 3-1 being set at 1.0.

First layer: HI-2; film thickness of 10 nm
Second layer: NPD; film thickness of 30 nm
Third layer: host material listed in Table 4 and light-emitting material (97:3); film thickness of 30 nm
Fourth layer: ET-4; film thickness of 10 nm
Fifth layer: electron transport material listed in Table 4; film thickness of 20 nm

TABLE 4

| Element number | Host material | Light-emitting material | Electron transport material | Emission color | Color purity | Luminous efficiency (relative value) | Change in chromaticity after driving |
|---|---|---|---|---|---|---|---|
| Element 3-1 | H-4 | Compound 1 | Alq | blue | ◎ | 1.2 | ◎ |
| Element 3-2 | CBP | Compound 4 | Alq | blue | ◎ | 1.2 | ◎ |
| Element 3-3 | H-4 | Compound 6 | Alq | blue | ○ | 1.2 | ◎ |
| Element 3-4 | CBP | Compound 8 | ET-5 | blue | ○ | 1.2 | ○ |
| Element 3-5 | H-4 | Compound 10 | ET-5 | blue | ○ | 1.1 | ◎ |
| Element 3-6 | H-4 | Compound 11 | Alq | blue | ○ | 1.2 | ◎ |
| Element 3-7 | CBP | Compound 17 | ET-5 | blue | ◎ | 1.2 | ◎ |
| Comparative element 3-1 | CBP | Comparative compound 1 | Alq | blue green | × | 1.0 | × |
| Comparative element 3-2 | H-4 | Comparative compound 2 | Alq | blue | Δ | 0.73 | × |
| Comparative element 3-3 | H-4 | Comparative compound 3 | ET-5 | blue | Δ | 0.65 | × |
| Comparative element 3-4 | H-4 | Comparative compound 4 | ET-5 | blue green | × | 0.47 | × |
| Comparative element 3-5 | CBP | Comparative compound 5 | Alq | blue | Δ | 0.63 | × |
| Comparative element 3-6 | CBP | Comparative compound 6 | Alq | blue | × | 0.89 | × |
| Comparative element 3-7 | CBP | Comparative compound 7 | Alq | blue green | × | 0.94 | × |

DESCRIPTION OF SYMBOLS 2 substrate
3 anode
4 hole injection layer
5 hole transport layer
6 light-emitting layer
7 hole blocking layer
8 electron transport layer
9 cathode
10 organic electroluminescent element
11 organic layer
12 protective layer
14 adhesive layer
16 sealing container
20 light-emitting device
30 light-scattering member
31 transparent substrate
30A light incidence face
30B light emission face
32 microparticles
40 lighting device

The invention claimed is:

1. A material for an organic electroluminescent element composed of a compound expressed by General Formula 1-1 below:

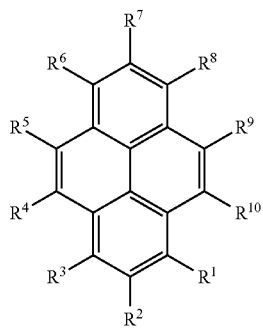

General Formula 1-1

$R^1$ to $R^{10}$ each independently represents a hydrogen atom or a substituent, wherein R to $R^{10}$ in General Formula 1-1 do not jointly form a ring; wherein exactly two of $R^1$ to $R^{10}$ are a substituent expressed by General Formula 1-2 below; however, a pyrene skeleton is never contained in R to $R^{10}$;

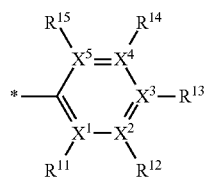

General Formula 1-2 wherein the asterisk indicates a bonding position with a pyrene ring; $X^1$ to $X^5$ each independently represents a carbon atom or a nitrogen atom, and at least three of $X^1$ to $X^5$ is a nitrogen atom;
$R^{11}$ to $R^{15}$ each independently represents a hydrogen atom or a substituent, wherein exactly one of $R^{11}$ to $R^{15}$ in each substituent expressed by General Formula 1-2 represents a silyl group; however, if $X^1$ to $X^5$ represent nitrogen atoms, there is no $R^{11}$ to $R^{15}$ bonded on these nitrogen atoms.

2. The material for an organic electroluminescent element according to claim 1, wherein the compound expressed by General Formula 1-1 is expressed by General Formula 2 below;

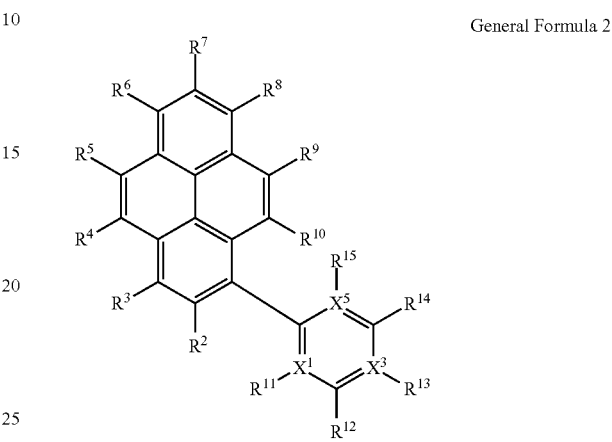

General Formula 2

$R^2$ to $R^{10}$ each independently represents a hydrogen atom or a substituent; provided that exactly one of $R^2$ to $R^{10}$ is a substituent expressed by General Formula 1-2; $X^1$, $X^3$, and $X^5$ each independently represents a nitrogen atom; $R^{12}$ and $R^{14}$ each independently represents a hydrogen atom or a substituent, exactly one of $R^{12}$ and $R^{14}$ in each substituent expressed by General Formula 1-2 represents a silyl group; $R^{11}$, $R^{13}$, and $R^{15}$ are not present; however, a pyrene skeleton is never contained in $R^2$ to $R^{10}$.

3. The material for an organic electroluminescent element according to claim 1, wherein each $R^{12}$ in General Formula 1-1 is a silyl group.

4. The material for an organic electroluminescent element according to claim 1, wherein the compound expressed by General Formula 1-1 is expressed by any of General Formulas 3-1 to 3-3 below;

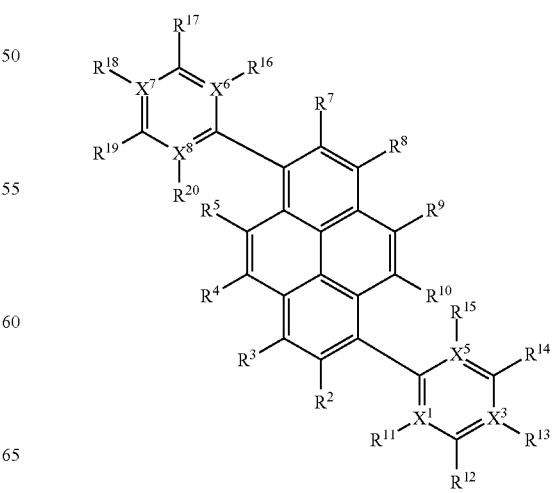

General Formula 3-1

-continued

General Formula 3-2

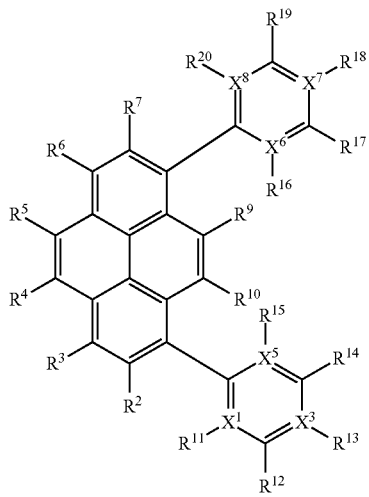

General Formula 3-3

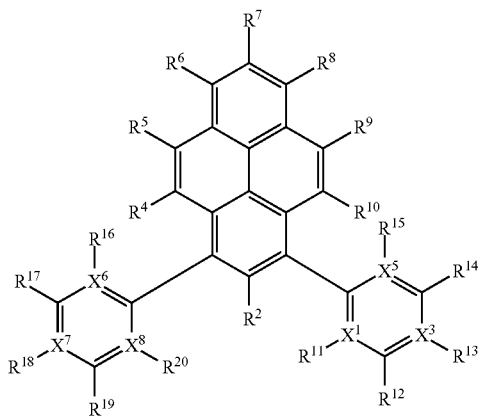

$R^2$ to $R^{10}$ each independently represents a hydrogen atom or a substituent; wherein none of $R^2$ to $R^{10}$ represents a group of General Formula 1-2; $X^1$, $X^3$, $X^5$, $X^6$, $X^7$, and X each represents a nitrogen atom; $R^{12}$, $R^{14}$, $R^{17}$, and $R^{19}$ each independently represents a hydrogen atom or a substituent, and exactly one of $R^{12}$ and $R^{14}$ and exactly one of $R^{17}$ and $R^{18}$ represents a silyl group; $R^{11}$, $R^{13}$, $R^{15}$, $R^{16}$, $R^{18}$, and $R^{20}$ are not present; however, a pyrene skeleton is never contained in $R^2$ to $R^{10}$.

5. The material for an organic electroluminescent element according to claim 4, wherein $R^{12}$, $R^{14}$, $R^{17}$, and $R^{18}$ in General Formulas 3-1 to 3-3 each independently represents a hydrogen atom, an alkyl group, or a silyl group.

6. The material for an organic electroluminescent element according to claim 1, wherein at least one of $R^2$, $R^3$, $R^4$, $R^5$, $R^7$, $R^9$, and $R^{10}$ in General Formula 1-1 is a substituent.

7. The material for an organic electroluminescent element according to claim 1, wherein at least one of $R^2$, $R^3$, $R^4$, $R^5$, $R^7$, $R^9$, and $R^{10}$ in General Formula 1-1 is a substituent selected from the group consisting of an alkyl group, a silyl group, an amino group, and a fluorine group.

8. The material for an organic electroluminescent element according to claim 1, wherein at least one of $R^2$ to $R^{10}$ in General Formula 1-1 is an ortho-alkyl-substituted phenyl group.

9. The material for an organic electroluminescent element according to claim 8, wherein said ortho-alkyl-substituted phenyl group is an o-tolyl group, a 2,6-xylyl group, or a mesityl group.

10. The material for an organic electroluminescent element according to claim 1, wherein $R^2$, $R^3$, $R^4$, $R^5$, $R^7$, $R^9$, and $R^{10}$ in General Formula 1-1 are each an alkyl group, a silyl group, an amino group, a fluorine atom, a phenyl group or pyridyl group, wherein the pyridyl group has been substituted with at least one alkyl group, silyl group, amino group, fluorine atom, or phenyl group, or a hydrogen atom.

11. The material for an organic electroluminescent element according to claim 1, wherein the molecular weight of the compound expressed by General Formula 1-1 is no greater than 1000.

12. The material for an organic electroluminescent element according to claim 1, wherein the compound expressed by General Formula 1-1 is a light-emitting material.

13. An organic electroluminescent element having
a substrate,
a pair of electrodes disposed on this substrate and composed of an anode and a cathode, and
at least one organic layer disposed between these electrodes and including a light-emitting layer, wherein
a compound expressed by General Formula 1-1 below is contained in at least one layer of said light-emitting layer:

General Formula 1-1

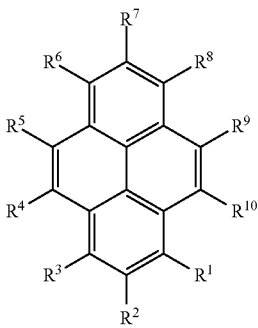

$R^1$ to $R^{10}$ each independently represents a hydrogen atom or a substituent, wherein $R^1$ to $R^{10}$ in General Formula 1-1 do not jointly form a ring; wherein exactly two of $R^1$ to $R^{10}$ are a substituent expressed by General Formula 1-2 below; however, a pyrene skeleton is never contained in $R^1$ to $R^{10}$;

General Formula 1-2

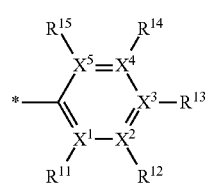

wherein the asterisk indicates a bonding position with a pyrene ring; $X^1$ to $X^5$ each independently represents a carbon atom or a nitrogen atom, and at least three of $X^1$ to $X^5$ is a nitrogen atom;
$R^{11}$ to $R^{15}$ each independently represents a hydrogen atom or a substituent, wherein exactly one of $R^{11}$ to $R^{15}$ in each substituent expressed by General Formula 1-2 represents a silyl group; however, if $X^1$ to $X^5$ represent nitrogen atoms, there is no $R^{11}$ to $R^{15}$ bonded on these nitrogen atoms.

14. The organic electroluminescent element according to claim 13, wherein said light-emitting layer includes an anthracene-based host material.

15. A light-emitting device, display device, or lighting device comprising the organic electroluminescent element according to claim 13.

16. The material for an organic electroluminescent element according to claim 1, wherein at least one of $R^1$ to $R^{10}$ represents a silyl group.

* * * * *